(12) United States Patent  
Schwartz et al.

(10) Patent No.: US 6,869,938 B1  
(45) Date of Patent: Mar. 22, 2005

(54) COMPOSITIONS OF POLYACIDS AND POLYETHERS AND METHODS FOR THEIR USE IN REDUCING ADHESIONS

(75) Inventors: Herbert E. Schwartz, Redwood City, CA (US); John M. Blackmore, Redwood City, CA (US); Stephanie M. Cortese, Atascadero, CA (US); William G. Oppelt, Arroyo Grande, CA (US)

(73) Assignee: FzioMed, Inc., San Luis Obispo, CA (US)

( * ) Notice: Subject to any disclaimer, the term of this patent is extended or adjusted under 35 U.S.C. 154(b) by 0 days.

(21) Appl. No.: 09/472,110

(22) Filed: Dec. 27, 1999

Related U.S. Application Data

(60) Continuation-in-part of application No. 09/023,097, filed on Feb. 13, 1998, now Pat. No. 6,034,140, which is a division of application No. 08/877,649, filed on Jun. 17, 1997, now Pat. No. 5,906,997.
(60) Provisional application No. 60/127,571, filed on Apr. 2, 1999.

(51) Int. Cl.[7] .......................... A61K 31/715; C07H 1/00
(52) U.S. Cl. .......................... 514/57; 514/42; 514/781; 514/912; 514/915; 536/3; 536/4; 536/51; 536/56; 536/112; 536/123.1
(58) Field of Search .......................... 514/42, 57, 781, 514/912, 915; 536/3, 4, 51, 56, 112, 123.1

(56) References Cited

U.S. PATENT DOCUMENTS

| | | | |
|---|---|---|---|
| 3,064,313 A | 11/1962 | Butler | 18/57 |
| 3,328,259 A | 6/1967 | Anderson | 167/84 |
| 3,387,061 A | 6/1968 | Smith et al. | 260/874 |
| 4,024,073 A | 5/1977 | Shimizu et al. | 252/316 |
| 4,141,973 A | 2/1979 | Balazs | 424/180 |
| 4,181,718 A | 1/1980 | Mason et al. | 424/180 |
| 4,442,258 A | 4/1984 | Sumakawa et al. | 524/767 |
| 4,610,863 A | 9/1986 | Tewari et al. | 423/338 |
| 4,616,644 A | 10/1986 | Saferstein et al. | 128/156 |
| 4,684,558 A | 8/1987 | Keusch et al. | 428/40 |
| 4,713,243 A | 12/1987 | Schiraldi et al. | 424/676 |
| 4,768,523 A | 9/1988 | Cahalan et al. | 128/785 |
| 4,772,419 A | 9/1988 | Malson et al. | 252/315.1 |
| 4,853,374 A | 8/1989 | Allen | 514/57 |
| 4,937,254 A | 6/1990 | Sheffield et al. | 514/420 |
| 4,937,270 A | 6/1990 | Hamilton et al. | 514/777 |
| 4,983,585 A | 1/1991 | Pennell et al. | 514/57 |
| 5,017,229 A | 5/1991 | Burns et al. | 106/162 |
| 5,066,709 A | 11/1991 | Chaudhuri et al. | 524/516 |
| 5,068,225 A | 11/1991 | Pennell et al. | 514/57 |
| 5,080,893 A | 1/1992 | Goldberg et al. | 514/57 |
| 5,093,319 A | 3/1992 | Higham et al. | 514/55 |
| 5,140,016 A | 8/1992 | Goldberg et al. | 514/57 |
| 5,156,839 A | 10/1992 | Pennell et al. | 424/78 |
| 5,266,326 A | 11/1993 | Barry et al. | 424/423 |
| 5,298,488 A | 3/1994 | Kojima et al. | 514/8 |
| 5,354,790 A | 10/1994 | Keusch et al. | 523/300 |
| 5,356,883 A | 10/1994 | Kuo et al. | 514/54 |
| 5,462,749 A | 10/1995 | Rencher | 424/484 |
| 5,502,081 A | 3/1996 | Kuo et al. | 514/777 |
| 5,532,221 A | 7/1996 | Huang et al. | 514/53 |
| 5,550,178 A | 8/1996 | Desair et al. | 524/56 |
| 5,621,093 A | 4/1997 | Swann et al. | 536/55.2 |
| 5,681,873 A | 10/1997 | Norton et al. | 523/115 |
| 5,709,854 A | 1/1998 | Griffith-Cima et al. | 424/93.7 |
| 5,711,958 A | 1/1998 | Cohn et al. | 424/423 |
| 5,800,832 A * | 9/1998 | Tapolsky et al. | 424/449 |
| 5,874,417 A | 2/1999 | Prestwich et al. | 514/54 |
| 5,906,997 A | 5/1999 | Schwartz et al. | 514/781 |

(List continued on next page.)

FOREIGN PATENT DOCUMENTS

| | | | |
|---|---|---|---|
| EP | 0 138 572 A2 | 4/1985 | C08B/37/08 |
| EP | 0 189 553 A2 | 6/1986 | |
| EP | 0 193 510 A1 | 9/1986 | C08B/37/08 |
| EP | 0 265 561 A1 | 10/1986 | C08B/37/08 |
| EP | 0 581 581 A2 | 2/1994 | |
| JP | 40-9241973 A | 9/1997 | |
| WO | WO 84/03302 | 8/1984 | C12P/19/04 |
| WO | WO 86/00912 | 2/1986 | C08B/37/00 |
| WO | WO 89/02445 | 3/1989 | C08B/37/08 |
| WO | WO 90/10020 | 9/1990 | C08B/37/08 |
| WO | 97/01345 * | 6/1996 | |
| WO | WO 98/58011 | 12/1998 | |

OTHER PUBLICATIONS

Kofinas, et al., "Development of Methods for Quantitative Characterization of Network Morphology in Pharmaceutical Hydrogels," *Elsevier Science Limited*, 1997, pp. 1361–1369.

(List continued on next page.)

*Primary Examiner*—James O. Wilson
*Assistant Examiner*—Howard V. Owens
(74) *Attorney, Agent, or Firm*—Fliesler Meyer LLP

(57) ABSTRACT

The present invention relates to improved methods for making and using bioadhesive, bioresorbable, anti-adhesion compositions made of intermacromolecular complexes of carboxyl-containing polysaccharides, polyethers, polyacids, polyalkylene oxides, multivalent cations and/or polycations. The polymers are associated with each other, and are then either dried into membranes or sponges, or are used as fluids or microspheres. Bioresorbable, bioadhesive, anti-adhesion compositions are useful in surgery to prevent the formation and reformation of post-surgical adhesions. The compositions are designed to breakdown in-vivo, and thus be removed from the body. Membranes are inserted during surgery either dry or optionally after conditioning in aqueous solutions. The anti-adhesion, bioadhesive, bioresorptive, antithrombogenic and physical properties of such membranes and gels can be varied as needed by carefully adjusting the pH and/or cation content of the polymer casting solutions, polyacid composition, the polyalkylene oxide composition, or by conditioning the membranes prior to surgical use. Multi-layered membranes can be made and used to provide further control over the physical and biological properties of antiadhesion membranes. Membranes and gels can be used concurrently. Antiadhesion compositions may also be used to lubricate tissues and/or medical instruments, and/or deliver drugs to the surgical site and release them locally.

42 Claims, 31 Drawing Sheets

U.S. PATENT DOCUMENTS

| | | | |
|---|---|---|---|
| 5,942,253 A | * 8/1999 | Gombotz et al. | 424/501 |
| 5,955,096 A | 9/1999 | Santos et al. | 424/434 |
| 5,968,500 A | 10/1999 | Robinson | 424/78.08 |
| 5,985,312 A | * 11/1999 | Jacob et al. | 424/434 |
| 6,017,301 A | 1/2000 | Schwartz et al. | 547/781 |

OTHER PUBLICATIONS

Anseth, et al., "Mechanical Properties of Hydrogels and their Experimental Determination," *Elsevier Science Limited, Biomaterials 17 (1996) 1647–1657*, pp. 1647–1657.

Agrawal, et al., Technique to Control pH in Vicinity of Biodegrading PLA–PGA Implants, *John Wiley & Sons, Inc.*, 1997, pp. 105–114.

Hunt, et al., "Silica Aerogel, A Transparent High Performance Insulator," *Proceedings of the International Solar Energy Society World Congress*, Sep. 13–18, 1987, Hamburg, West Germany, pp. 1–5.

Tewari, et al., "Microstructural Studies of Transparent Silica Gels and Aerogels," *Proceedings of the 1986 Spring Meeting of the Materials Research Society*, Apr. 15–19, 1986, Palo Alto, CA., pp. 1–11.

Hunt, et al., "Process Considerations in Monolithic Aerogels," *Materials Research Society*, 1988, Materials Research Society Symposium, vol. 121, pp. 679–684.

Lenaerts, Ph.D., et al., "Bioadhesive Drug Delivery Systems," *CRC Press, Inc.*, 1990, pp. 25–168.

Lofftus, et al., "Colloidal and Kinetic Principles of Sol–Gel Processing," *Advanced Materials '90*, Mar., 1990.

* cited by examiner

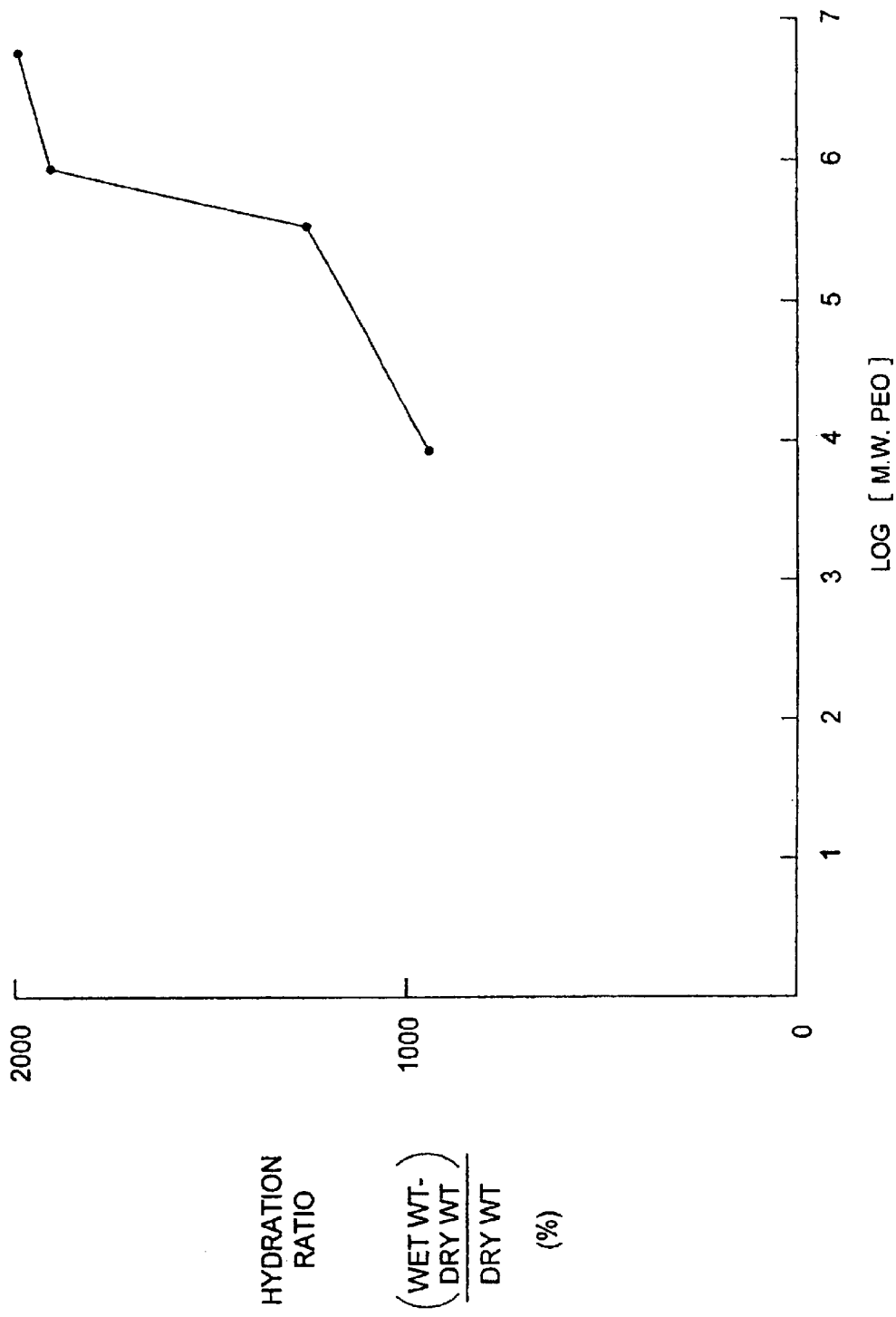

US 6,869,938 B1

COMPOSITIONS OF POLYACIDS AND POLYETHERS AND METHODS FOR THEIR USE IN REDUCING ADHESIONS

RELATED CASES

This Application is a Continuation-In-Part of U.S. patent application Ser. No. 09/023,097, filed Feb. 13, 1998, now U.S. Pat. No. 6,034,140 which is a Division of U.S. patent application Ser. No. 08/877,649, filed Jun. 17, 1997, now U.S. Pat. No. 5,906,997, issued May 25, 1999, which claims priority to U.S. Provisional Patent Application Ser. No. 60/127,571, filed Apr. 2, 1999, now abandoned. Each of these patents and patent applications is herein incorporated fully by reference.

FIELD OF THE INVENTION

This invention relates generally to the manufacture and use of membranes comprising carboxypolysaccharide/polyether intermacromolecular complexes, cross-linked gels comprising polyacids, polyalkylene oxides and multivalent ions and the use of those membranes and gels to inhibit the formation of adhesions between tissues after surgery, after trauma, and/or after disease processes. The properties of the compositions can be tailored to achieve desired degrees of adhesion prevention, bioresorbability, bioadhesiveness, and antithrombogenic effects.

BACKGROUND OF THE INVENTION

Adhesions are unwanted tissue growths occurring between layers of adjacent bodily tissue or between tissues and internal organs. Adhesions commonly form during the healing which follows surgical procedures, and when present, adhesions can prevent the normal motions of those tissues and organs with respect to their neighboring structures.

The medical and scientific communities have studied ways of reducing the formation of post-surgical adhesions by the use of high molecular weight carboxyl-containing biopolymers. These biopolymers can form hydrated gels which act as physical barriers to separate tissues from each other during healing, so that adhesions between normally adjacent structures do not form. After healing has substantially completed, the barrier is no longer needed, and should be eliminated from the body to permit more normal function of the affected tissues.

Several different types of biopolymers have been used for this purpose. For example, Balazs et al., U.S. Pat. No. 4,141,973 discloses the use of a hyaluronic acid (HA) fraction for the prevention of adhesions. However, because HA is relatively soluble and readily degraded in vivo, it has a relatively short half-life in vivo of 1 to 3 days, which limits its efficacy as an adhesion preventative.

Methyl cellulose and methyl cellulose derivatives are also known to reduce the formation of adhesions and scarring that may develop following surgery. (Thomas E. Elkins, et al., *Adhesion Prevention by Solutions of Sodium Carboxymethylcellulose in the Rat, Part I, Fertility and Sterility, Vol. 41. No. 6, June 1984*; Thomas E. Elkins, M. D. et al., *Adhesion Prevention by Solutions of Sodium Carboxymethylcellulose in the Rat, Part II, Fertility and Sterility. Vol. 41. No. 6 Jun. 1984*. However, these solutions are rapidly reabsorbed by the body and disappear from the surgical site.

Additionally, solutions of polyethers can also decrease the incidence of post-surgical adhesions. Pennell et al., U.S. Pat. No. 4,993,585 describes the use of polyethylene oxide in solutions of up to 15% to decrease formation of post-surgical adhesions. Pennell et al., U.S. Pat. No. 5,156,839 describes the use of mixtures of carboxymethylcellulose up to about 2.5% by weight, and polyethylene oxide, in concentrations of up to about 0.5% by weight in physiologically acceptable, pH neutral mixtures. Because of the neutral pH, these materials do not form association complexes, and thus, being soluble, are cleared from the body within a short period of time.

The above-described solutions can have disadvantages in that they can have short biological residence times and therefore may not remain at the site of repair for sufficiently long times to have the desired anti-adhesion effects. Therefore, antiadhesion membranes using certain polymers have been made.

Although certain carboxypolysaccharide-containing membranes have been described, prior membranes can have disadvantages for use to prevent adhesions under certain conditions. Butler, U.S. Pat. No. 3,064,313 describes the manufacture of films made of 100% carboxymethylcellulose (CMC) with a degree of substitution of 0.5 and below, made insoluble by acidifying the solution to pH of between 3 and 5, and then drying the mixture at 70° C. to create a film. These films were not designed to be used as anti-adhesion barriers.

Anderson, U.S. Pat. No. 3,328,259 describes making films of 100% carboxymethylcellulose and polyethylene oxide, alkali metal salts, and a plasticizing agent for use as external bandages. These materials are rapidly soluble in plasma and water and thus would have a very short residence time as an intact film. Therefore, these compositions are not suitable for alleviating surgical adhesions.

Smith et al., U.S. Pat. No. 3,387,061 describes insoluble association complexes of carboxymethylcellulose and polyethylene oxide made by lowering the pH to below 3.5 and preferably below 3.0, and then drying and baking the resulting precipitate (see Example XXXVIII). These membranes were not designed for surgical use to alleviate adhesions. Such membranes are too insoluble, too stiff, and swell to little to be ideal for preventing post-surgical adhesions.

Burns et al., U.S. Pat. No. 5,017,229 describes water insoluble films made of hyaluronic acid, carboxymethyl cellulose, and a chemical cross-linking agent. Because of the covalent cross-linking with a carbodiimide, these films need extensive cleaning procedures to get rid of the excess cross-linking agent; and because they are made without a plasticizer, they are too stiff and brittle to be ideally suited for preventing adhesions they do not readily conform to the shapes of tissues and organs of the body.

Thus, there is a need for antiadhesion membranes and gels that can be used under a variety of different circumstances. D. Wiseman reviews the state of the art of the field in *Polymers for the Prevention of Surgical Adhesions, In: Polymeric Site-specific Pharmacotherapy*, A. J. Domb, Ed., Wiley & Sons, (1994). A currently available antiadhesion gel is made of ionically cross-linked hyaluronic acid. (Huang et al., U.S. Pat. No. 5,532,221, incorporated herein fully by reference).

Ionic cross-linking of polysaccharides is well documented in the chemical and patent literature (Morris and Norton, *Polysaccharide Aggregation in Solutions and Gels*, Ch. 19, in Aggregation Processes in Solution, Wyn-Jones, E. and Gormally, J, Eds., Elsevier Sci. Publ. Co. NY (1983)). Each type of metal ion can be used to form gels of different polymers under specific conditions of pH, ionic strength, ion concentration and concentrations of polymeric components.

For example, alginate (a linear 1,4-linked beta-D-mannuronic acid, alpha-L-glucuronic acid polysaccharide) can form association structures between polyglucuronate sequences in which divalent calcium ions can bind, leading to ordered structures and gel formation. Similar calcium binding ability is also demonstrated by pectin which has a poly-D-galacturonate sequence. The order of selectivity of cations for pectins is $Ba^{2+}>Sr^{2+}>Ca^{2+}$. CMC also can bind to monovalent and divalent cations, and CMC solutions can gel with the addition of certain trivalent cations (*Cellulose Gum*, Hercules, Inc., page 23 (1984)).

Sayce et al. (U.S. Pat. No. 3,969,290) discloses an air freshener gel comprising CMC and trivalent cations such as chromium or aluminum.

Smith (U.S. Pat. No. 3,757,786) describes synthetic surgical sutures made from water-insoluble metal salts of cellulose ethers.

Shimizu et al. (U.S. Pt. No. 4,024,073) describe hydrogels consisting of water-soluble polymers such as dextran and starch chelated with cystine or lysine through polyvalent cations.

Mason et al. (U.S. Pat. No. 4,121,719) disclose CMC- and gum arabic-aluminum hydrogels used as phosphate binding agents in the treatment of hyperphosphatemia.

U.S. Pat. No. 5,266,326 describes alginate gels made insoluble by calcium chloride.

An antiadhesion gel is made of ionically cross-lied hyaluronic acid (Huang et al., U.S. Pat. No. 5,532,221). Cross-linking is created by the inclusion of polyvalent cations, such as ferric, aluminum or chromium salts. Hyaluronic acid (either from natural sources or bio-engineered) is quite expensive.

Therefore, the prior art discloses no membranes or gels which are ideally suited to the variety of surgical uses of the instant invention.

Pennell et al (U.S. Pat. No. 5,156,839) describes CMC solutions containing small amounts of high molecular weight PEO. In one embodiment, Pennell describes covalently cross-linking gels using dimethylolurea.

Thus, there are several objects of the instant invention.

A first object is to provide compositions and methods which reduce the incidence of adhesion formation during and after surgery. This includes the prevention of de novo adhesion formation in primary or secondary surgery.

An additional object is to prevent reformation of adhesions after a secondary procedure intended to eliminate the de novo adhesions which had formed after a primary procedure.

Another object is to provide inexpensive antiadhesion compositions which remain at the surgical site during the initial stages of critical wound healing.

Yet another object of the invention is to provide an antiadhesion membrane which can hydrate quickly in a controlled fashion to form an intact hydrogel.

An additional object of the invention is to provide an antiadhesion membrane which has controlled degrees of bioresorbability.

A further object of the invention is to provide an antiadhesion membrane which has good handling characteristics during a surgical procedure, is conformable to a tissue, pliable, strong, and easy to mold to tissue surfaces, and possesses sufficient bioadhesiveness to ensure secure placement at the surgical site until the likelihood of adhesion formation is minimized.

Yet another objective of the invention is to provide an antiadhesion membrane with desired properties with drugs incorporated into the membrane, so that the drug can be delivered locally over a period of time to the surgical site.

Another object of the invention is to provide gel compositions having improved viscoelastic, antiadhesion, coatability, tissue adherence, anti-thrombogenicity or bioresorbability.

A further object is to provide combined membrane/gel compositions with improved antiadhesion properties.

To achieve these objectives, in certain embodiments of the instant invention one can carefully control the properties of antiadhesion membranes by closely regulating the pH, amounts of carboxyl residues and polyether within the carboxypolysaccharide/polyether association complex, to closely control the degree of association between the polymers. By carefully controlling the degree of intermolecular binding and amount of polyether, we can closely vary the physical properties of the membranes and therefore can optimize the antiadhesion, bioadhesive, bioresorptive, and antithrombogenic properties of the membranes to achieve the desired therapeutic results.

In other embodiments of the invention, multivalent cations including $Fe^{3+}$, $Al^{3+}$, and $Ca^{2+}$, and/or polycations including polylysine, polyarginine and others, can be used to provide intermolecular attraction, thereby providing gels having increased viscosity.

Too much hydration can result in an irreversible transformation of the membrane to a "loose gel" which will not stay in place or can disintegrate. In addition, too much swelling can create too much hydrostatic pressure which could adversely affect tissue and organ function. The membrane must be physiologically acceptable, be soft, have the desired degree of bioresorbability, have the desired degree of antithrombogenicity, and must be biologically inert.

SUMMARY OF THE INVENTION

One aspect of the invention is a composition comprising an intermacromolecular association of a carboxypolysaccharide (CPS) and a polyether (PE), for example, a polyethylene glycol ("PEG") which are useful for inhibiting post-surgical adhesions.

Another aspect of the invention comprises methods of manufacturing complexes of CPS and PE which can exhibit desired physical and biological properties.

Creation of complexes in the form of membranes with desired properties is accomplished by varying the degree of bonding between the polymers. This variation in properties is accomplished by varying the pH of the casting solution (hereafter referred to as "the membrane pH"), the molecular weights of the polymers, the percentage composition of the polymer mixture, and/or the degree of substitution (d.s.) by carboxyl residues within the CPS, and the presence and concentration(s) of multivalent cations and/or polycations. Additional variation in membrane properties is accomplished by conditioning membranes after their initial manufacture. Multi-layered membranes are also an aspect of the invention, with different layers selected to exhibit different properties.

To address the problems of the prior art antiadhesion compositions, we have discovered new antiadhesion gels based on association complexation between ionically associated polyacids ("PA") and hydrophilic polyalkylene oxides ("PO"). The PA of this invention can be made with polyacrylic acid, carboxypolysaccharides such as CMC, and other polyacids known in the art. Ionically cross-linked gels of this invention can be made by mixing polyacid and polyether together, either in dry form or in aqueous solution, and then adding a solution containing cations to provide cross-linking between the PA, the PO and the cations. In certain embodiments, the pH of the mixture can be adjusted to provide a degree complexation directly between the PA and the PO, thus resulting in a composition that can be associated by both hydrogen bonds and by ionic bonds. Subsequently, the pH and/or osmolality of the composition can be adjusted to be physiologically acceptable. The gels can then be sterilized and stored before use.

The membranes and gels of this invention can be used to inhibit post-surgical adhesions, to decrease the consequences of arthritis, and/or to provide a lubricant for numerous medical and/or veterinary uses.

Additionally, in accordance with some aspects of the invention, drugs can be included in the membranes or gels to deliver pharmacological compounds directly to the tissues.

In certain embodiments, the compositions can be sterilized using thermal methods, gamma irradiation, and ion beams which can alter the physical and other properties of the components. Alternatively, in other embodiments of this invention, the materials can be filter sterilized.

The materials are biocompatible, and are cleared from the body within a desired period of time, which can be controlled.

Unlike the prior art, anti-adhesion compositions can be made having desired properties. Furthermore, conditioning of anti-adhesion membranes after their manufacture can result in unexpected properties, which have certain desirable advantages.

By using both gel compositions and membrane compositions together in the same treatment procedure, improved anti-adhesion properties can be achieved.

BRIEF DESCRIPTION OF THE FIGURES

FIG. 7 shows the effect of changing the molecular weight of PEO on hydration or swelling of CMC/PEO membranes.

FIG. 11a shows the results from a pH of from about 1.3 to about 4.2.

FIG. 11b shows the results of the same study as in FIG. 11a but from a pH of 1.3 to about 3.

FIG. 25a depicts the effects of γ-irradiation on CMC/PEO membranes.

FIG. 25b depicts the effects of γ-irradiation on CMC and PEO standards.

FIG. 25c depicts the effects of γ-irradiation and autoclaving on CMC and PEO a casting solutions.

DETAILED DESCRIPTION

Definitions

Figure 1:
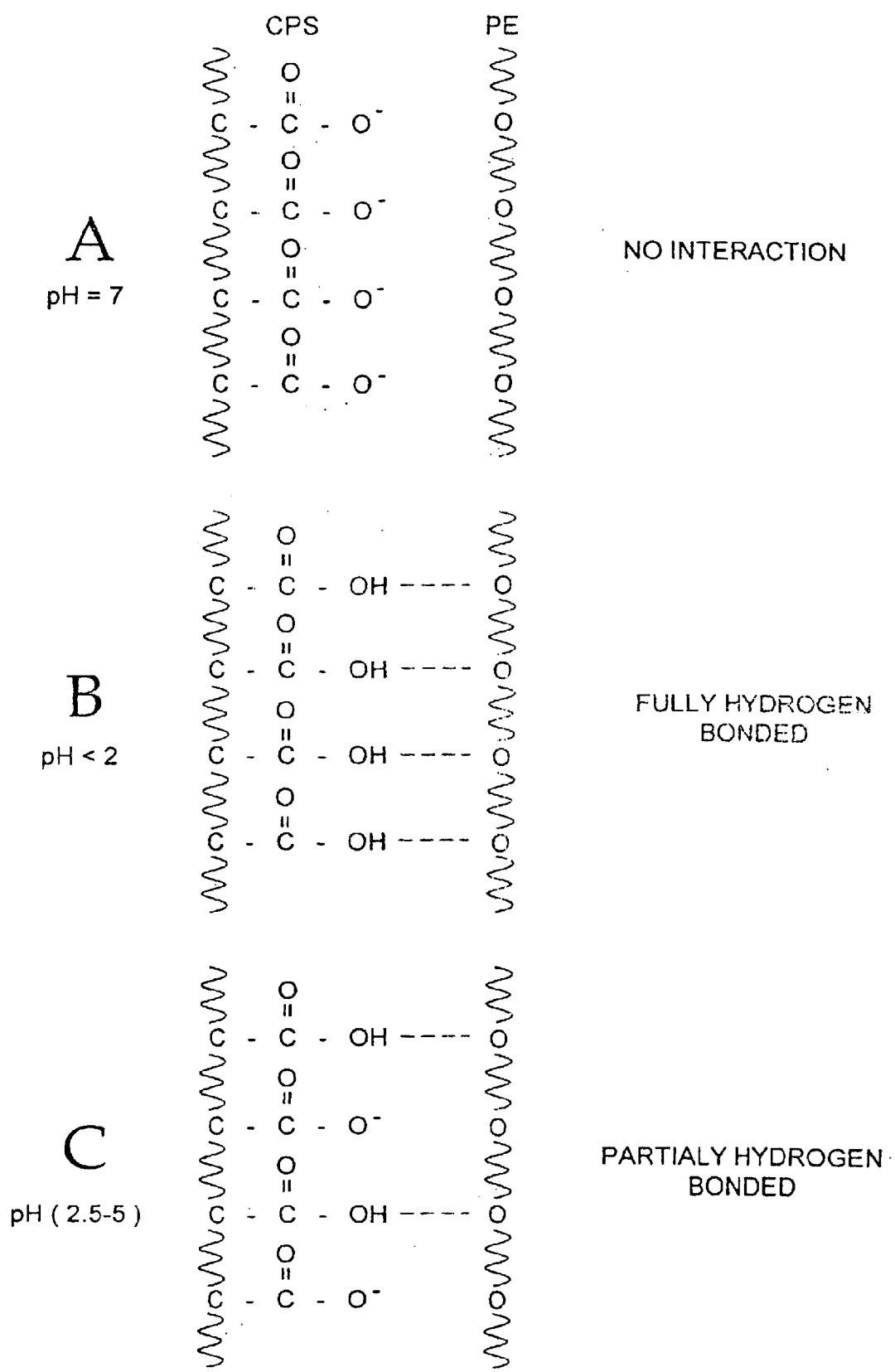
FIG. 1 is a schematic representation of a theory of formation of association complexes between carboxypolysaccharides and polyethers resulting from hydrogen bonding at different pHs.

Before describing the invention in detail, the following terms are defined as used herein.

The term "adhesion" means abnormal attachments between tissues and organs that form after an inflammatory stimulus such as surgical trauma.

The terms "adhesion prevention" and "anti-adhesion" means preventing or inhibiting the formation of post-surgical scar and fibrous bands between traumatized tissues, and between traumatized and nontraumatized tissues.

The term "association complex" or "intermacromolecular complex" means the molecular network formed between polymers containing CPS, polyacids, PE, polyalkylene oxide and/or multivalent ions, wherein the network is cross-linked through hydrogen and/or ionic bonds.

The term "bioadhesive" means being capable of adhering to living tissue.

The term "bioresorbable" means being capable of being reabsorbed and eliminated from the body.

The term "biocompatible" means being physiologically acceptable to a living tissue and organism.

The term "carboxymethylcellulose" ("CMC") means a polymer composed of repeating carboxylated cellobiose units, further composed of two anhydroglucose units (β-glucopyranose residues), joined by 1,4 glucosidic linkages. The cellobiose units are variably carboxylated.

The term "carboxypolysaccharide" ("CPS") means a polymer composed of repeating units of one or more monosaccharides, and wherein at least one of the monosaccharide units has a hydroxyl residue substituted with a carboxyl residue.

The term "chemical gel" means a gel network comprised of covalently cross-linked polymers.

The term "degree of substitution" ("d.s.") means the average number of carboxyl or other anionic residues present per mole of cellobiose or other polymer.

The term "discectomy" means a surgical operation whereby a ruptured vertebral disc is removed.

The term "endoscope" means a fiber optic device for close observation of tissues within the body, such as a laparoscope or arthroscope.

The term "fibrous tissue" means a scar or adhesions.

The term "gel pH" means the pH of the gel or the pH of the casting solution from which the gel or a partially dried form of the gel is formed.

The term "hyaluronic acid" ("HA") means an anionic polysaccharide composed of repeat disaccharide units of N-acetylglucosamine and glucuronic acid. HA is a natural component of the extracellular matrix in connective tissue.

The term "hydration" (also "swelling") means the process of taking up solvent by a polymer solution.

The term "hydration ratio" (also "swelling ratio") means the wet weight of a hydrated membrane, sponge or microsphere less the dry weight divided by the dry weight×100%.

The term "hydrogel" means a three-dimensional network of hydrophilic polymers in which a large amount of water is present.

The term "laminectomy" means a surgical procedure wherein one or more vertebral lamina are removed.

The term "laparoscope" means a small diameter scope inserted through a puncture wound in the abdomen, used for visualization during minimally invasive surgical procedures.

The term "membrane pH" means the pH of the casting solution from which the membrane is made.

The term "mesothelium" means the epithelium lining the pleural, pericardial and peritoneal cavities.

The term "peritoneum" means the serous membrane lining the abdominal cavity and surrounding the viscera.

The terms "physical gel," "physical network" and "pseudo gel" mean non-covalently cross-linked polymer networks wherein the association of polymers in these gels is characterized by relatively weak and potentially reversible chain-chain interactions, which can be comprised of hydrogen bonding, ionic association, ionic bonding, hydrophobic interaction, cross-linking by crystalline segments, and/or solvent complexation.

The term "polyacid" means molecules comprising subunits having dissociable acidic groups.

The term "polyalkylene oxide" ("PO") means non-ionic polymers comprising alkylene oxide monomers. Examples of polyalkylene oxides include polyethylene oxide (PEO), polypropylene oxide (PPO) and polyethylene glycol (PEG), or block copolymers comprising PO and/or PPO.

The term "polycation" means a polymer containing multiple positively charged moieties. Examples of polycations include polylysine, polyarginine, and chitosan.

The term "polyethylene glycol" ("PEG") means a non-ionic polyether polymer being composed of ethylene oxide monomers, and having a molecular weight in the range of about 200 daltons ("d") to about 5000 daltons.

The term "polyethylene oxide" ("PEO") means the non-ionic polyether polymer composed of ethylene oxide monomers. The molecular weight of PEO as used herein is between 5,000 d and 8,000 kilodaltons ("kd").

The term "solids" used with reference to polymer compositions means the total polymer content as a weight percentage of the total weight of the composition.

The term "solids ratio" means the percentage of the total dry polymer contents as a weight percentage of the total solids content.

The term "tissue ischemia" means deprivation of blood flow to living tissues.

Detailed Description of the Invention

Certain embodiments of the present invention are directed to compositions and methods of reducing the formation of adhesions during and following surgery and/or wound healing comprising the step of delivering to a wound or a tissue, an implantable, bioresorbable association complex of carboxypolysaccharides (CPS), a polyacid (PA), a polyalkylene oxide (PO), a polyether (PE), a polyethylene glycol (PEG), and or multivalent ions and/or polycations. Complexes in membrane form can generally made by mixing appropriate amounts and compositions of CPS and PE together in solution, then, optionally acidifying the solution to a desired pH to form an acidified association complex, and then if desired, by pouring the solution into a suitable flat surface and permitting the mixture to dry to form a membrane at either reduced (>0.01 Torr) or normal (about 760 Torr) atmospheric pressure. The association complex is placed between tissues which, during wound healing, would otherwise tend to form adhesions between them. The complex remains at the site for different periods of time, depending upon its composition, method of manufacture, and upon post-manufacture conditioning. When the tissues have substantially healed, the complex then degrades and/or dissolves and is cleared from the body.

I. Membranes

Membranes in accordance with the invention can be made with desired degrees of stiffness, different rates of bioresorbability, different degrees of bioadhesion, different degrees of anti-adhesion effectiveness and different degrees of antithrombogenic properties.

A. Association Complexation

Although the exact mechanism of association complex formation between a CPS and a PE is not completely known, one theory is that hydrogen bonding can occur between the carboxyl residues of the polysaccharide and the ether oxygen atoms of the polyether. See Dieckman et al., Industrial and Engineering Chemistry 45(10):2287–2290 (1953). FIG. 1 illustrates this theory. The pH of the polymer solution from which the membrane is cast (the "casting solution") is carefully titrated to an acidic pH by means of a suitable acid. The initially neutral, anionic polysaccharide carboxyl groups are converted into protonated, free carboxylic acid groups by the addition of the acid (e.g. hydrochloric acid) to the mixed polymer casting solution. The protonated carboxyl residues can subsequently bond electrostatically to the ether oxygen atoms of the polyether, thereby forming hydrogen bonds, a type of dipole-dipole interaction.

Decreasing the pH of the casting solution increases the number of protonated carboxyl residues, which increases the number of possible hydrogen bonds with the polyether. This strengthens the polymer network, and results in a stronger, more durable, less soluble and less bioresorbable membrane. On the other hand, if the casting solution is near neutral pH, the carboxyl groups on the carboxypolysaccharide are more negatively charged and thus repel both each other and the ether oxygen atoms of the PE, resulting in a weakly hydrogen-bonded gel with little or no structural integrity.

Figure 2:
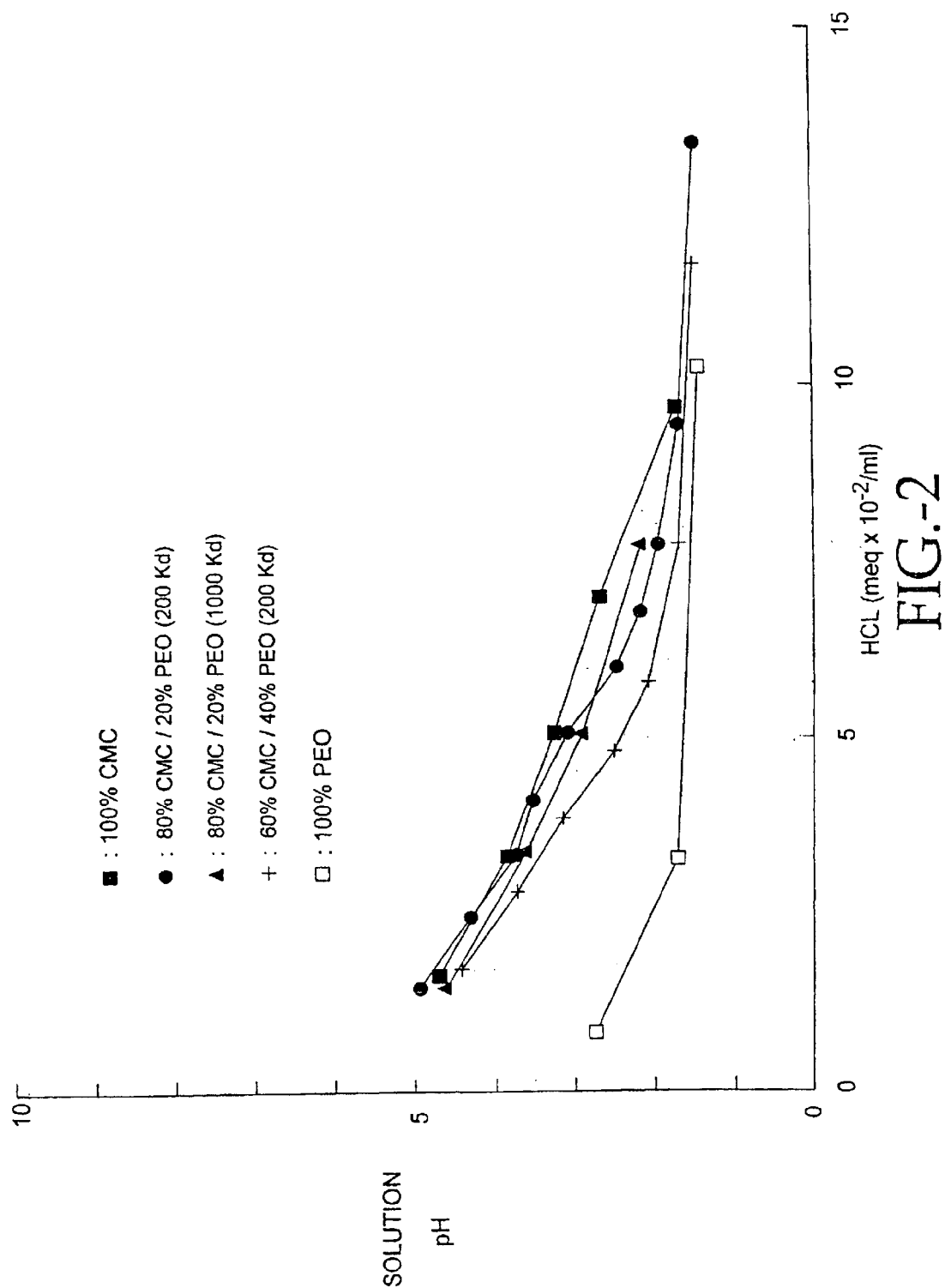
FIG. 2 shows the results of studies of pH titrations of the solutions made for casting CMC- and polyethylene oxide (PEO)-containing membranes.

For the purpose of illustration, three cases of such interactions can be distinguished as shown in FIG. 1. The figure shows a schematic representation of the possible intermolecular complexation in which four carboxymethyl groups from a carboxypolysaccharide (CPS) chain are aligned opposite to four ether oxygen atoms of a polyether (PE) chain. FIG. 1a shows the situation which would exist at a pH of about 7. At neutral pH, the carboxyl residues are dissociated, so no hydrogen bonded complex is formed between the ether oxygen atoms of the PE and the negatively charged carboxymethyl groups of CPS. FIG. 1b shows the situation which would exist at a pH of about 2. At low pH, most of the carboxyl residues are protonated, so most are hydrogen-bonded to the ether oxygen atoms of the PE. FIG. 1c shows the situation which would exist at a pH of approximately 3–5. At the $pK_a$ of the CPS of about 4.4, half of the carboxyl groups are protonated, and thus are hydrogen bonded to the corresponding ether oxygen atoms of the PE. Within this intermediate pH region, the degree of cross-linking can be carefully adjusted according to the present invention (FIG. 2).

Membranes made according to FIG. 1b are like those described by Smith et al. (1968). They lack the several key features of the ideal adhesion preventative membrane. The low pH membranes hydrate poorly. Further, they are rough to the touch, non-pliable, and are poorly soluble. Because they are insoluble, they would not be cleared from the body in a sufficiently short time period. Moreover, because of the high acidity of the casting solution, they deliver a relatively larger amount of acid to the tissue compared to more neutral pH membranes. Physiological mechanisms may have difficulty in neutralizing this acid load before tissue damage occurs. Thus, they have poor biocompatability.

In contrast to the prior art membranes described above, the present invention teaches adhesion preventative membranes as schematically depicted in FIG. 1c. These membranes are made in an intermediate pH range, typically between approximately 3 and 5, so that the amount of cross-linking is neither too great, which would result in complexes which would not dissolve rapidly enough, nor too little, which would result in a complex which would disintegrate too rapidly. Furthermore, varying the pH of the casting solutions varies the Theological properties of the solution (Table 1), and varies the physical properties of the membranes made from those solutions (Table 2).

The above mechanism for formation of association complexes is not necessary to the invention. The results of our studies with CPS and PE describe the invention fully, without reliance upon any particular theory of the association between the components.

Manufacturing membranes from CPS/PE casting solutions requires only that the solution of CPS and PE can be handled easily. Dilute solutions (up to about 10% weight/volume) of CPS are easy to handle, and solutions of about 2% CPS are easier to handle. Solutions of PEO up to about 20% (weight/volume) are possible to make and handle, and solutions of about 1% by weight are easy to handle.

B. Carboxypolysaccharides

The carboxypolysaccharide may be of any biocompatible sort, including but not limited to carboxymethyl cellulose (CMC), carboxyethyl cellulose, chitin, carboxymethyl chitin, hyaluronic acid, alginate, pectin, carboxymethyl dextran, carboxymethyl chitosan, and glycosaminoglycans such as heparin, heparin sulfate, and chondroitin sulfate. Other suitable CPSs include the polyuronic acids polymannuronic acid, poly glucuronic acid and polyguluronic acid, and propylene glycol alginate. Alternatively, carboxymethyl cellulose or carboxyethyl cellulose is used. In other embodiments, carboxymethyl cellulose (CMC) is used. The molecular weight of the carboxypolysaccharide can vary from 100 kd to 10,000 kd. CPS in the range of from 600 kd to 1000 kd work well, and CPS of 700 kd works well, and is easily obtained commercially. The degree of substitution (d.s.) can be 0.4 greater than 0 up to and including 3 for CMC. For other CPSs, the d.s. can be from greater than 0 up to and including the maximum d.s. for that particular CPS.

C. Polyethers and Polyethylene Glycol

Similarly, the polyether used is not crucial. A suitable polyether of the present invention is polyethylene oxide (PEO). Whereas CMC sodium by itself has been used as an antiadhesion barrier in a gel formulation, CMC/PEO compositions have some unique properties useful for adhesion prevention.

Membranes made of CMC and PEO together are more flexible than membranes made of CMC alone, which are hard and stiff. The membranes may accordingly be manipulated during surgery to conform closely to the shape needed for close adherence to a variety of tissues. Further, the inclusion of PEO in the complex confers antithrombogenic properties which can help prevent adhesions by decreasing the adherence of blood proteins and platelets to the membrane (M. Amiji, *Biomaterials,* 16:593–599 (1995); Merill, E. W., *PEO and Blood Contact in Polyethylene Glycol Chemistry-Biotechnical and Biomedical Applications*, Harris J. M. (ed), Plenum Press, NY, 1992; Chaikof et al., *A.I. Ch.E. Journal* 36(7):994–1002 (1990)). PEO-containing membranes can impair the access of fibrin clots to tissue surfaces, even more so than a membrane containing CMC alone. Increasing flexibility of CMC/PEO membranes without compromising the tensile strength improves the handling characteristics of the membrane during surgery. The molecular weight range of the polyether as used in this invention can vary from about 5 kd to about 8000 kd. Polyethers in the range from 100 kd to 5000 kd work well and are readily available commercially.

Polyethylene glycol (PEG) is a polymer, similar to PEO, except that the numbers of monomer units in the polymer is generally less than for PEO. The MW of PEG suitable for this invention is in the range of about 200 d to about 5 kd, alternatively about 1000 d to 4000 d, and in other embodiments, about 2000 d.

In addition to PEO, plasticizers, such as glycerol can be incorporated into the compositions of this invention. Glycerol and other plasticizers can increase the flexibility of membranes. Other plasticizers than glycerol include ethanolamines, ethylene glycol, 1,2,6-hexanetriol, mono-, di- and triacetin, 1,5-pentanediol, polyethylene glycol (PEG), propylene glycol and trimethylol propane. The glycerol content of the composition can be in the range of greater than about 0% to about 30% by weight. In alternative embodiments, the content of glycerol can be in the range of about 2% to about 10%, and in yet other embodiments, in the range of about 2% to about 5%. As the percentage of glycerol in the films increased, the film become more plastic, having a rubbery texture, and was softer to the touch than films not having glycerol. In one experiment, a film made with 30% glycerol was placed on the skin and adhered to a similar degree as a control film not having glycerol incorporated therein. Incorporation of glycerol improves the handling characteristics, and can provide membranes that are easy to roll up and apply using a specially designed insertion device, herein termed a "Filmsert™" device. A description of the Filmsert device is found in co-pending patent application by Oppelt et al., titled "Laparoscopic Insertion and Deployment Device" Ser. No. 09/180,010, filed Oct. 27, 1998, incorporated herein fully by reference.

Varying the ratio of the polysaccharide and polyether alters viscoelastic properties of the solutions (Tables 4, 5), and produces different degrees of adhesion prevention and antithrombogenic effects. Increasing the percentage of CPS increases the bioadhesiveness, but reduces the antithrombogenic effect. On the other hand, increasing the percentage of PE increases the antithrombogenic effect but decreases bioadhesiveness. The percentage of carboxypolysaccharide to polyether may be from 10% to 100% by weight, preferably between 50% and 90%, and most preferably should be 90% to 95%. Conversely, the percentage of polyether may be from 0% to 90%, preferably from 5% to 50%, and most preferably should be approximately 5% to 10%.

The tightness of the association and thus the physical properties of the association complex between the CPS and PE may be closely regulated. Decreasing the pH of the association complex increases the amount of hydrogen cross-linking. Similarly, increasing the degree of substitution of the carboxypolysaccharide in the membrane increases cross-linking within the association complex at any given pH, and thereby decreases the solubility and therefore the bioresorbability of the complex. Membranes made from low pH polymer solutions are generally harder and stiffer, dissolve more slowly, and therefore have longer residence times in tissues than do membranes made from solutions with higher pH or of hydrogels. Low pH polymer membranes are generally useful in situations where the period of adhesion formation may be long, or in tissues which heal slowly. Such situations may occur in recovery from surgery to ligaments and tendons, tissues which characteristically heal slowly. Thus, a long-lasting membrane could minimize the formation of adhesions between those tissues. However, low pH membranes are rough to the touch, crack easily when folded, and tend to shatter easily.

In contrast, membranes made from solutions with higher pH are more flexible and easier to use than membranes made from solutions with lower pH. They are more bioadhesive and biodegrade more rapidly than membranes made at lower pH, and are therefore more useful where the period of adhesion formation is short. These membranes feel smooth, and are pliable, and are capable of being folded without as much cracking or shattering compared to membranes made from solutions with low pH.

The pH of the compositions of the present invention may be between 1 and 7, alternatively between 2 and 7, in other embodiments, between 2.5 and 7, in other embodiments, between 3 and 7, and in yet other embodiments, between 3.5 and 6.0. For certain uses, a pH of about 4.1 is desired where there is a desirable balance between the bioadhesiveness, antiadhesion properties, the rates of bioresorbability and the biocompatability for several uses contemplated in the present invention.

D. Bioadhesiveness and Hydration

Bioadhesiveness is defined as the attachment of macromolecules to biological tissue. Bioadhesiveness is important in preventing surgical adhesions because the potential barrier must not slip away from the surgical site after being placed there. Both CMC and PEO individually are bioadhesive (e.g., see Bottenberg et al., *J. Pharm. Pharmacol.* 43: 457–464 (1991)). Like other polymers which are known to swell when exposed to water, CMC/PEO membranes are also bioadhesive.

Hydration contributes to bioadhesiveness of membranes (Gurney et al, *Biomaterials* 5:336–340 (1984); Chen et al., *Compositions Producing Adhesion Through Hydration, In: Adhesion in Biological Systems*, R. S. Manly (Ed.) Acad. Press NY (1970), Chapter 10). A possible reason for this phenomenon is that with increased hydration, more charges on the CMC become exposed, and therefore may be made available to bind to tissue proteins. However, excessive hydration is detrimental to bioadhesion. Thus, a means of controlling the bioadhesiveness of membranes is to control their hydration properties.

Figure 3:
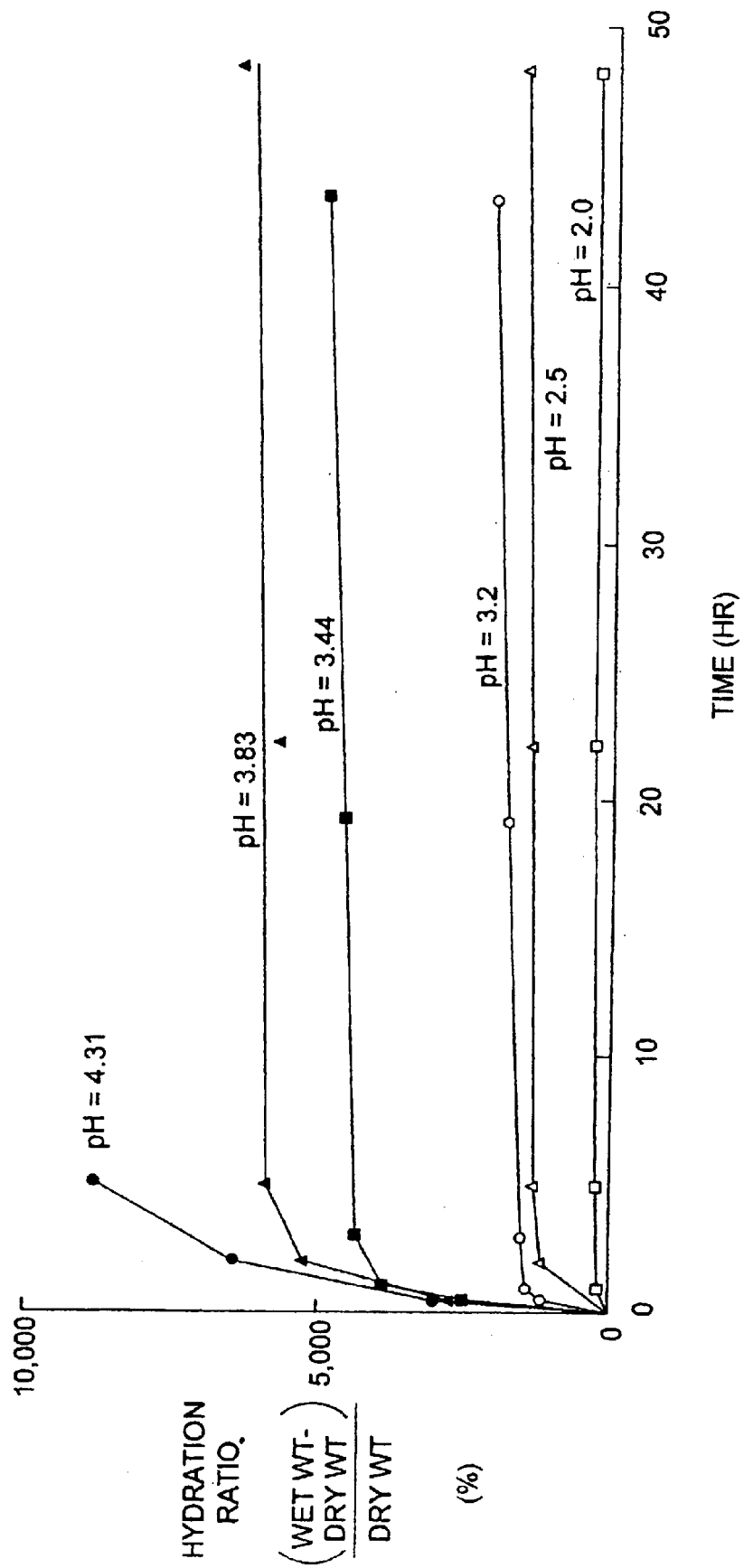
FIG. 3 shows the time course of hydration or swelling of CMC/PEO membranes made from casting solutions at different pHs, from 2.0 to 4.31 at room temperature.

The membranes of the present invention rapidly hydrate in PBS solution (FIG. 3). This behavior mimics that of membranes placed on moist tissues during surgery or treatment for injuries. The hydration of the membranes increases both the thickness of the barrier and its flexibility, thus permitting it to conform to the shape of the tissues to be separated during the period during which adhesions could form. The preferred hydration ratios (% increase in mass due to water absorption) that provide desirable adhesion prevention are about 100%4000%, alternatively 500%4000%, in other embodiments, the ratios are between 700%–3000%, and for other embodiments, a desired hydration ratio for alleviating adhesions is approximately 2000% FIG. 4).

In addition to decreasing the pH of the association complex, increased intermacromolecular association can be achieved using CPSs with increased degree of carboxyl substitution. By increasing the density of protonatable carboxyl residues on the CPS, there is increasing likelihood of hydrogen bond formation even at a relatively high pH. The degree of substitution of CPS must be greater than 0, i.e., there must be some carboxyl residues available for hydrogen bond formation. However, the upper limit is theoretically 3 for cellulose derivatives, wherein for each mole of the saccharide, 3 moles of carboxyl residues may exist. Thus, in the broadest application of the invention involving CPS as the polyacid, the d.s. is greater than 0 and up to and including 3. In other embodiments, the d.s. is between 0.3 and 2. CPS with d.s. between 0.5 and 1.7 work well, and CPSs with a d.s. of about 0.65–1.45 work well and are commercially available.

E. Bioresorption

The complexes of the instant invention are intended to have a finite residence time in the body. Once placed at a surgical or wound site, or site of inflammation, the dried membranes hydrate rapidly, turning into a gel-like sheet and are designed to serve as a barrier for a limited time period. Once healing has substantially taken place, the anti-adhesion barrier naturally disintegrates, and the components are cleared from the body. The time taken to clear the body for certain embodiments is desirable no more than 29 days because of increased regulation by the Food and Drug Administration of devices intended to remain within the body for more than 30 days. However, it can be desirable to provide longer-duration compositions for certain long-term uses.

Figure 5:
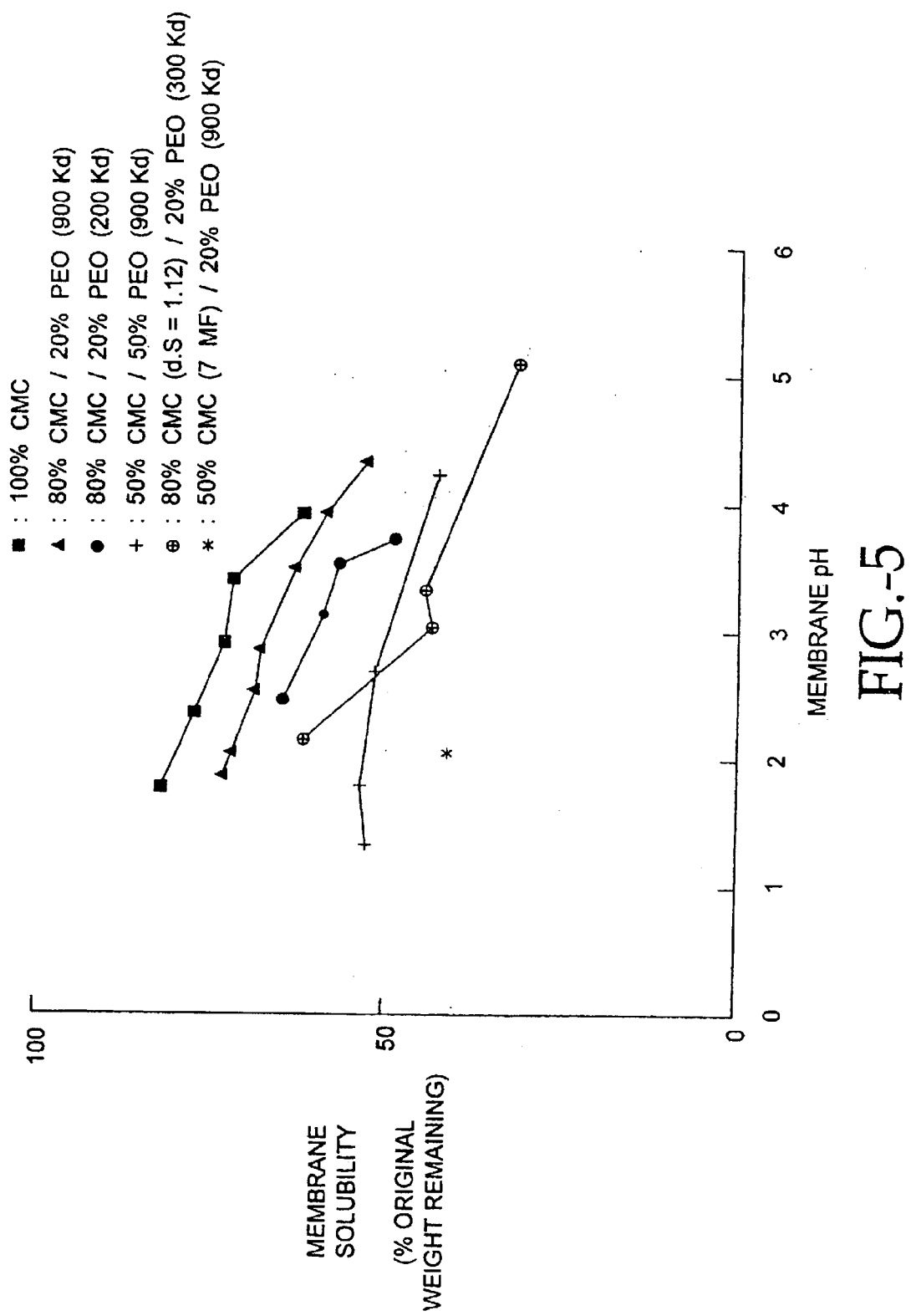
FIG. 5 shows solubility in PBS of membranes of different composition and pH.

The mechanisms for bioresorption of CMC/PEO complexes are not well understood. However, an early step in the process of bioresorption is solubilization of the network of CMC and PEO. Thus, increasing the solubility of the complex increases the ease of clearing the components from the tissue (FIG. 5). When soluble, CMC and PEO can diffuse into the circulation and be carried to the liver and kidneys, where they may be metabolized or otherwise eliminated from the body. Additionally, enzymatic action can degrade carbohydrates. It is possible that enzymes contained in neutrophils and other inflammatory cells may degrade the polymer networks and thereby increase the rate of elimination of the components from the body.

The degradation and rate of solubilization and disruption of the membrane is manipulated by careful adjustment of the pH during formation of the association complexes, by varying the CPS/PE ratio, and by selecting the appropriate degree of substitution of the CPS and molecular weights of the PE and CPS. Decreasing the molecular weight of CPS increases its solubility. (Kulicke et al., *Polymer* 37(13): 2723–2731 (1996). The strength of the membrane can be tailored to the surgical application. For example, certain surgical applications (e.g., spine or tendon) may require a stronger, more durable membrane than others (such as intraperitoneal applications). Manipulation of the above-mentioned experimental variables allows the manufacture and use of products with variable residence times in the body.

F. Biocompatability

Figure 6:
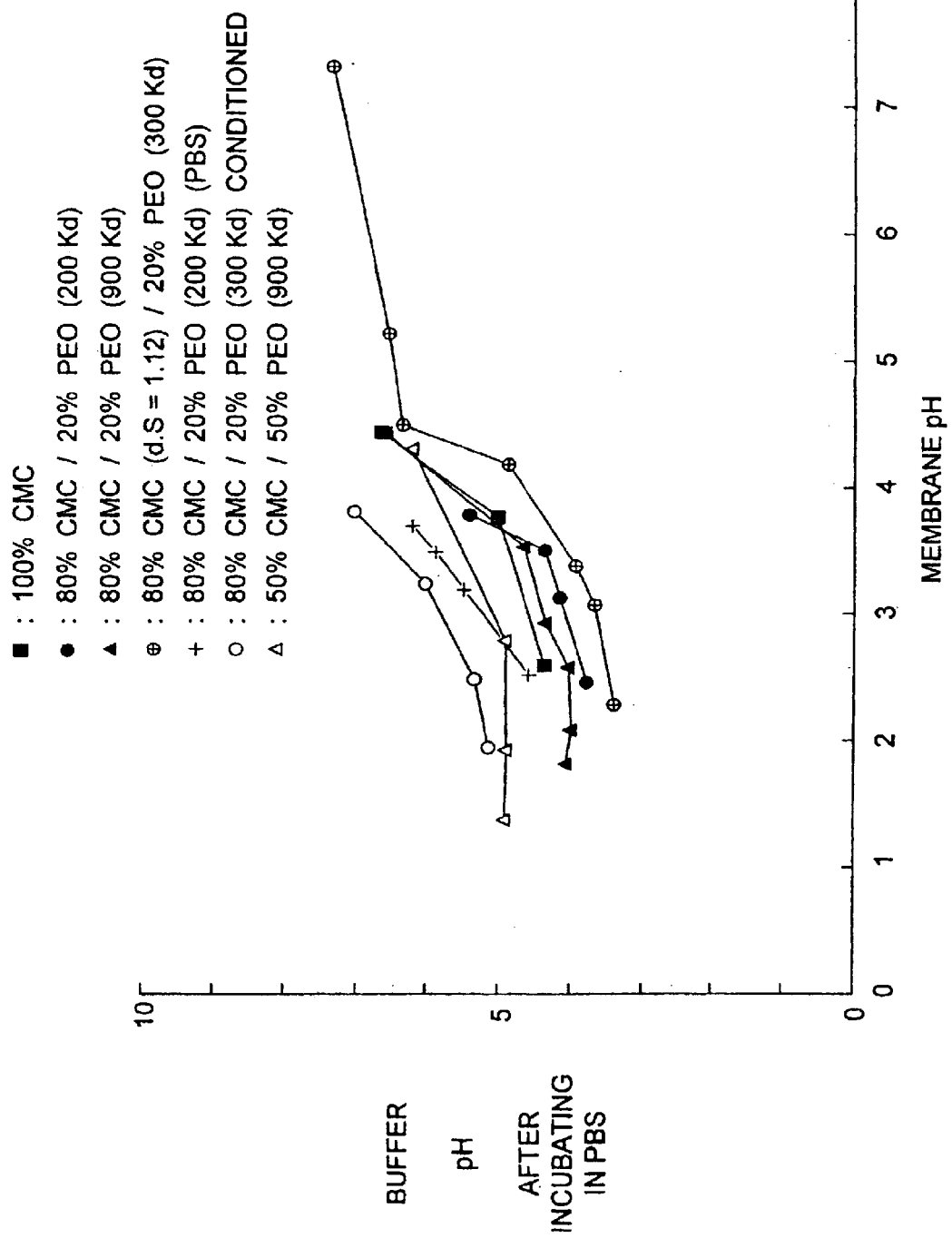
FIG. 6 shows results of studies of the acidification of PBS solutions by CMC/PEO membranes.

Biocompatability of CPS/PE complexes of the present invention can be a function of its acidity. A highly acidic complex contributes a relatively larger total acid load to a tissue than does a more neutral complex. Additionally, the more rapidly hydrogen ions dissociate from a complex, the more rapidly physiological mechanisms must compensate for the acid load by buffering, dilution and other mechanisms. To mimic the rate and total amount of acid given up by a membrane in vivo, membranes are placed in PBS solutions and the degree of acidification of the PBS is measured. In addition to membrane pH, membrane composition also influences the acid load delivered to the body. FIG. 6 and Tables 3 and 6 show the results of studies designed to mimic the delivery of acid by membranes to tissues.

After their manufacture, membranes may be modified to suit the particular needs of the user. For example, relatively bioresorbable membranes maybe made more insoluble by treating them with solutions containing an acid, exemplified, but not limited to hydrochloric, sulfuric, phosphoric, acetic, or nitric acid, the "acidic" method.

Conversely, a relatively non-resorbable acidic membrane may be made more bioresorbable and bioadhesive by conditioning it with alkali such as ammonia (the "alkaline" method), or with a buffered solutions such as phosphate buffer (PB) or phosphate buffered saline (PBS; the "buffer" methods). A 10 mM solution of PBS at a pH of 7.4 is preferred, due to the biocompatability of phosphate buffers. Moreover, the pH of a membrane may be buffered without eliminating the advantages of membranes made at lower pH. Thus, an originally acid membrane will hydrate slowly and have a relatively long residence time even if its pH is raised by alkali or buffer treatment.

Table 7 shows the effects of ammonia treatment on properties of CMC/PEO membranes. A highly acidic original membrane (pH 2.03) acidified a PBS buffer solution originally at a pH of 7.40 by lowering its pH to 4.33. After soaking this membrane in PBS solution, it hydrated to over 2.5 times its original dry weight and after 4 days in PBS, this membrane lost approximately 29% of its original mass. In an identical membrane, incubation for 1 min in a 0.5N ammonia solution substantially neutralized the membrane so that it released few hydrogen ions into the buffer solution, and the pH of the PBS solution remained nearly neutral (pH 7.29).

Table 8 shows the effects of phosphate-buffer treatment on properties of CMC/PEO membranes. Membranes treated with 50 mM phosphate buffer solution for progressively longer time periods had increasingly neutral pH as judged by their decreased release of acid into a PBS solution. Similarly, PBS (10 mM phosphate buffer) neutralized the acid in membranes (Table 9). Therefore, membranes can be made which are physiologically compatible with tissues, yet because they are made at an acidic original pH which creates an association complex, the membranes retain the desired properties of the original complex.

G. Multilayered Membranes

Additionally, multi-layered membranes may be made, for example, to incorporate a low pH inner membrane, surrounded by an outer membrane made with a higher pH. This composition permits the introduction of a membrane with long-term stability and low rate of bioresorbability of the inner membrane while minimizing adverse effects of low pH membranes, such as tissue damage and the stimulation of inflammatory responses. Moreover, the high pH outer portion is more bioadhesive than low pH membranes, ensuring that such a membrane remains at the site more securely.

Multilayered membranes may also be made which include as one layer, a pure CPS or PE membrane. Such a membrane could have the flexibility, antiadhesion, and solubility properties of the side which is a mixture of CPS and PE, and have the property of the pure material on the other. For example, bioadhesiveness is a property of CPS, and a pure CPS side would have the highest degree of bioadhesiveness. Alternatively, a pure PE membrane would have the most highly antithrombogenic properties. Thus, a membrane can be made which incorporates the desired properties of each component.

Multilayered membranes can also be made in which two layers have different ratios of CPS and PE. For example, in certain embodiments, a bilayered membrane having 97.5% CMC/2.5% PEO on one side, and a 60% CMC/40% PEO layer on the other side.

Membranes of this invention exhibit several desirable properties, including, but not limited to anti-adhesion, bioadhesive, anti-thrombogenic, and bioresorbable. The membranes of this invention can be flexible, and can be inserted through cannulae during minimally invasive surgical procedures.

H. Ionically Cross-Linked Polyacid/Polyalkylene Oxide Compositions

Other embodiments of the present invention are directed to ionically cross-linked gels for reducing surgical adhesions, decreasing the symptoms of arthritis, and providing biologically compatible lubricants. Methods for accomplishing these aims comprise the step of delivering to a wound or other biological site, an implantable, bioresorbable composition comprised of a polyacid and a polyether which are associated with each other by way of ionic bonding, ionic association or ionic crosslinking. We have unexpectedly found that a mixture of a polyether, a polyacid and an ionic crosslinking agent can increase the viscosity of the gel above the viscosity predicted on the basis of either the interactions between the polyether and the crosslinking ions, the polyacid and the polyether, or the polyacid and ions. Thus, the compositions of this invention provide advantages not found in previously disclosed antiadhesion compositions.

Certain embodiments having relatively little intermolecular ionic bonding can be more readily resorbed than embodiments having more bonding. Thus, increasing intermolecular bonding can increase residence time of the composition in the body, and therefore can remain at the site for a longer period of time than compositions having smaller degrees of intermolecular bonding. By way of example, by selecting compositions which provide the highest viscosity (see below), the residence time can be adjusted to provide a desired lifetime of antiadhesion effect. Additionally, in certain other embodiments, the compositions can be dried to form a membrane, which can further increase the residence time at a tissue site. Thus, by selecting the chemical composition of the gel, and by selecting the form of the composition (e.g., gel or membrane), a desired combination of properties can be achieved to suit particular needs.

A. Gel Structures

The gels of this invention are termed "physical gels." The term physical gels has been used (de Gennes, P. G. *Scaling Concepts in Polymer Physics.* Ithaca, N.Y. Cornell University Press, p, 133, (1979)) to describe non-covalently cross-linked polymer networks. Physical gels are distinguished from "chemical gels" which are covalently cross-linked. Physical gels are relatively weak and have potentially reversible chain-chain interactions which may be comprised of hydrogen bonds, ionic association, hydrophobic interaction, stereo-complex formation, cross-linking by crystalline segments, and/or solvent complexation.

Ionically cross-linked gels can be made by mixing appropriate amounts and compositions of polyacids, polyether and cross-linking cations together in a solution. Additionally, and optionally, the solution can be acidified to promote cross-linking of the polyacid and polyether molecules through hydrogen bonds as described for carboxypolysaccharides and polyethers above and in U.S. patent application Ser. No. 08/877,649, filed Jun. 17, 1997, now U.S. Pat. No. 5,906,997, issued May 25, 1999; U.S. patent application Ser. No. 09/023,267, filed Feb. 23, 1998; U.S. patent application Ser. No. 09/023,097; and U.S. patent application Ser. No. 09/252,147, filed Feb. 18, 1999. Each aforementioned Patent Application herein incorporated fully by reference.

The ionically cross-linked gels can be made in the form of a membrane by pouring the solution onto a suitable flat surface, such as a tray, and permitting the mixture to dry to form a membrane at either reduced (>0.01 Torr) or normal (about 760 Torr) atmospheric pressure. Additionally, sponges and microspheres of gel materials can be made. The ionically cross-linked association complex can be placed between tissues which, during wound healing, would form adhesions between them. The complex can remain at the site for different periods of time, depending upon its composition, method of manufacture, and upon post-manufacture conditioning. When the tissues have substantially healed, the complex can then degrade and/or dissolve and is cleared from the body.

Ionically cross-linked gels and membranes in accordance with the invention can be made with desired degrees of viscosity, rigidity, different rates of bioresorbability, different degrees of bioadhesion, different degrees of antiadhesion effectiveness and different degrees of antithrombogenic properties.

Although the exact mechanism of ionic cross-linking of polyacid/polyether association complex formation is not completely known, one theory is that ionic bonding or association occurs between the acid residues of the polyacid and the ether oxygen atoms of the polyether. According to this theory, divalent ions such as calcium ($Ca^{2+}$), cobalt ($Co^{++}$), magnesium ($Mg^{++}$), manganese ($Mn^{++}$) and trivalent ions such as iron ($Fe^{3+}$) and aluminum ($Al^{3+}$) can lie between the acidic residues of the poly acid and the ether oxygen atoms of the polyether and can be attracted to valence electrons with the acid and oxygen atoms, thereby forming an ionic bond. Because trivalent ions have three valences, according to this theory, trivalent ions can provide tighter ionic bonding between the polymers of the solution. Additionally, cross-linking can occur between adjacent polyacid molecules, thereby trapping polyether molecules without the necessity for direct poly acid/polyether association through ionic interactions. Cross-linking can also be accomplished by the use of a polycation such as polylysine, polyarginine or chitosan. However, this invention does not rely upon any particular theory for operability.

Additionally, adjusting the pH of the solution can affect the degree of ionic bonding that can occur between pH sensitive acidic residues and the ether oxygen atoms. For example, if a polyacid such as CMC is used, at lower pH, fewer of the carboxyl residues can be dissociated, and fewer carboxyl electrons can be available for ionic bonding to polyether oxygen atoms. In these situations, increased ionic bonding can promoted by increasing the pH of the solution.

However, reducing the pH can increase the degree of hydrogen bonding that can occur between polymers. See Dieckman et al., Industrial and Engineering Chemistry 45(10):2287–2290 (1953). By adding acid (e.g. hydrochloric acid) to the CPS solution, the initially neutral, anionic polysaccharide carboxyl groups are converted into protonated, free carboxylic acid groups. The protonated carboxyl residues can subsequently bond electrostatically to the ether oxygen atoms of the polyether, thereby forming hydrogen bonds.

Decreasing the pH of the polymer solution can increase the number of protonated carboxyl residues, which can increase the number of possible hydrogen bonds with the polyether. This can strengthen the polymer network, and can result in a stronger, more durable, less soluble and less bioresorbable composition. On the other hand, if the polymer solution is near neutral pH, the carboxyl groups on the carboxypolysaccharide are more negatively charged and thus repel both each other and the ether oxygen atoms of the PE, resulting in a weakly hydrogen-bonded gel.

Thus, by combining the use of ionic cross-linking and hydrogen bonding, the gels of this invention can be manufactured to have specifically desired properties.

The above mechanisms for formation of ionically cross-linked association complexes is not necessary to the invention. Our invention does not rely upon any particular theory of the association between the components.

Ionically cross-linked compositions of PA and PO require only that the solutions of PA and PO can be handled easily. Dilute solutions (up to about 10% weight/volume) of CPS are easy to handle, and solutions of about 2% CPS are easier to handle. Solutions of PEO up to about 20% (weight/volume) are possible to make and handle, and solutions of about 1% by weight are easy to handle. However, the maximal concentration can be increased if the molecular weight of the PE is reduced. By way of example only, PEG having a molecular weight of about 1000 Daltons can be made in a concentration of about 50%. Further decreasing the molecular weight of the PE can permit even higher concentrations to be made and handled easily.

B. Polyacid Components

The polyacid may be of any biocompatible sort. By way of example, a group of polyacids useful for the present invention are carboxypolysaccharides (CPS) including carboxymethyl cellulose (CMC), carboxyethyl cellulose, chitin, carboxymethyl chitin, hyaluronic acid, alginate, pectin, carboxymethyl dextran, carboxymethyl chitosan, and glycosaminoglycans such as heparin, heparin sulfate, and chondroitin sulfate. Additionally, polyuronic acids such as polymannuronic acid, polyglucuronic acid, and polyguluronic acid, as well as propylene glycol alginate can be used. Additionally, polyacrylic acids, polyamino acids, polylactic acid, polyglycolic acids, polymethacrylic acid, polyterephthalic acid, polyhydroxybutyric acid, polyphosphoric acid, polystyrenesulfonic acid, and other biocompatible polyacids known in the art are suitable. Such polyacids are described in *Biodegradable Hydrogels for Drug Delivery*, Park et al., Ed., Technomic Publishing Company, Basel, Switzerland (1993), incorporated herein fully by reference. Preferably, carboxymethylcellulose or carboxyethylcellulose is used. More preferably, carboxymethylcellulose (CMC) is used. The molecular weight of the carboxypolysaccharide can vary from 10 kd to 10,000 kd. CPS in the range of from 600 kd to 1000 kd work well, and CPS of 700 kd works well, and is easily obtained commercially.

C. Polyalkylene Oxide Components

Similarly, many polyalkylene oxides can be used. These include polypropylene oxide (PPO), PEG, and PEO and block co-polymers of PEO and PPO, such as the Pluronics™ (a trademark of BASF Corporation, North Mount Olive, N.J.). The preferred PO of the present invention is polyethylene oxide (PEO) having molecular weights of between about 5,000 Daltons (d) and about 8,000 Kd. Additionally, polyethylene glycols (PEG) having molecular weights between about 200 d and about 5 kd are useful.

The inclusion of a polyether in the complex confers antithrombogenic properties which help prevent adhesions by decreasing the adherence of blood proteins and platelets to a composition (M. Amiji, *Biomaterials*, 16:593–599 (1995); Merill, E. W., *PEO and Blood Contact in Polyethylene Glycol Chemistry-Biotechnical and Biomedical Applications*, Harris J. M. (ed), Plenum Press, NY, 1992; Chaikof et al., *A.I. Ch.E. Journal* 36(7):994–1002 (1990)). PEO-containing compositions impair the access of fibrin clots to tissue surfaces, even more so than a composition containing CMC alone. For embodiments of the invention wherein the ion-associated gels are dried to form membranes, sponges, or microspheres, increasing flexibility of CMC/PEO compositions without compromising the tensile strength or flexibility improves the handling characteristics of the composition during surgery.

A The inclusion of PE to the gels also can increase the spreading or coating ability of the gel onto biological tissues. By increasing the spreading, there is increased likelihood that the gel can more efficiently coat more of the tissue and thereby can decrease the likelihood of formation of adhesions at sites remote from the injured tissue.

Varying the ratios and concentrations of the polyacid, the polyether and multivalent cations or polycations can alter viscoelastic properties of the solutions and can produce different degrees of bioadhesion, adhesion prevention and antithrombogenic effects. Increasing the percentage of polyacid increases the bioadhesiveness, but reduces the antithrombogenic effect. On the other hand, increasing the percentage of PE increases the antithrombogenic effect but decreases bioadhesiveness. The percentage ratio of polyacid to PO may be from about 10% to 99% by weight, alternatively between about 50% and about 99%, and in another embodiment about 90o/o to about 99%. Conversely, when the PO is PE, the percentage of PE can be from about 1% to about 90%, alternatively from about 1% to about 50%, and in another embodiment, about 1% to 10%. In another embodiment, the amount of PE can be about 2.5%.

D. Ionic Components

The tightness of the association and thus the physical properties of the association complex between the PA and PO may be closely regulated by selection of appropriate multivalent cations. In certain embodiments, it can be desirable to use cations selected from groups 2, 8, or 13 of the periodic table. Increasing the concentration and/or valence of polyvalent cations can increase ionic bonding. Therefore, trivalent ions of group 3 of the periodic table such as $Fe^{3+}$, $Al^{3+}$, $Cr^{3+}$ can provide stronger ionic cross-linked association complexes than ions of group 2, such as $Ca^{2+}$, $Cr^{3+}$, or $Zn^{2+}$. However, other cations can be used to cross-link the polymers of the gels of this invention. Polycations such as polylysine, polyarginine, chitosan, or any other biocompatible, polymer containing net positive charges under aqueous conditions can be used.

The anions accompanying the cations can be of any biocompatible ion. Typically, chloride (Cl) can be used, but also $PO_4^{2-}$, $HPO_3^-$, $CO_3^{2-}$, $HCO_3^-$, $SO_4^{2-}$, borates such as $B_4O_7^{2-}$ and many common anions can be used. Additionally, certain organic polyanions can be used. By way of example, citrate, oxalate and acetate can be used. In certain embodiments, it can be desirable to use hydrated ion complexes, because certain hydrated ion salts can be more easily dissolved that anhydrous salts.

Moreover, decreasing the pH of the association complex increases the amount of hydrogen cross-linking. Similarly, increasing the degree of substitution of the carboxypolysaccharide in the gel can increase cross-linking within the association complex at any given pH or ion concentration. The pH of the gels can be between about 2 and about 7.5, alternatively between about 6 and about 7.5, and in other embodiments, about 3.5 to about 6.

E. Methods for Calculating Degree of Ionic Association of Ionically Cross-Linked Gels The degree of ionic association and cross-linking can be varied by varying the concentration of the cation used. A method for comparing the changes in viscosity of gels of this invention is to compare the measured viscosity of a gel as a function of a calculated degree of ionic association. The degree of ionic association is related to the degree of cross-inking between polymer chains in a cross-linked gel. A method for determining the ionic association of an ionically cross-linked gel can be calculated according to the following method, exemplified for CMC. CMC consists of repeating units of carboxymethylated anhydroglucose units (referred herein to as "CMAG" units). 100% ionic association is achieved when 3 CMAG units bind with one trivalent ion, such as $Fe^{3+}$. Theoretically, the % ionic association ("% IA") is related to the number of moles of a trivalent ion ("$I^{3+}$") and the number of moles of the CMAG ("CMAG") as follows:

$$\% IA = \frac{\text{Moles } I^{3+}}{\text{Moles } CMAG} \times 3 \times 100 \%  \quad \text{(Equation 1)}$$

For example, the amount of iron chloride ($FeCl_3$) needed to produce 30% ionic association of a 500 ml sample of gel containing 2% by weight/volume of total solids, CMC/PEO ratio of 95%/5% using PEO with a molecular weight of 8,000 kd. The CMC has a degree of substitution of 0.82. The amount of CMC is corrected for the water content present in the bulk material (6% water) and for the degree of substitution. A degree of substitution of 0.82 indicates that the CMC was manufactured with 8.2 carboxymethyl groups per 10 anhydroglucose units. Thus, $$\text{Moles } CMAG = \frac{9.5 \text{ g } CMC(0.94) \times 0.82}{242 \text{ g/mol } CMAG}$$

Thus, Moles CMAG 0.0303.

Rearranging Equation 1 and solving for the number of moles of iron:

$$\text{Moles Fe} = \frac{0.00303 \text{ mol } CMAG \times 30 \% \text{ } IA}{3 \times 100 \%}$$
$$= 0.00303 \text{ mol.}$$

Therefore, the volume of a 25.2 (weight/volume % $FeCl_3 \cdot 6H_2O$ solution needed is:

$$= \frac{0.00303 \text{ mol} \times 270.2 \text{ gm/mol} \times 100 \text{ ml}}{25.2 \text{ gm}}$$
$$= 3.2 \text{ ml.}$$

Table 1 shows the comparison of calculated percentage of ionic association and ion concentration for each ion listed for gels made with a ratio of CMC:PEO of 95:5 and 2% total solids content.

TABLE 1

Relationship Between Percentage Ionic Association to Ion Concentration

| % Ionic Association | mmol Fe | mmol Al | mmol Ca |
|---|---|---|---|
| 5 | 0.47 | 0.47 | 0.7 |
| 10 | 1.03 | 1.03 | 1.54 |
| 15 | 1.49 | 1.49 | 2.24 |
| 20 | 2.05 | 2.05 | 3.08 |
| 25 | 2.52 | 2.52 | 3.78 |
| 30 | 2.98 | 2.98 | 4.48 |
| 35 | 3.54 | 3.54 | 5.33 |
| 40 | 4.01 | 4.01 | 6.03 |
| 45 | 4.57 | 4.57 | 6.87 |
| 50 | 5.04 | 5.03 | 7.57 |
| 55 | 5.5 | 5.5 | 8.27 |
| 60 | 6.06 | 6.06 | 9.11 |
| 65 | 6.53 | 6.52 | 9.81 |
| 70 | 7.09 | 7.08 | 10.85 |
| 75 | 7.55 | 7.55 | 11.35 |
| 80 | 8.11 | 8.11 | 12.19 |
| 85 | 8.58 | 8.57 | 12.89 |
| 90 | 9.05 | 9.04 | 13.39 |

TABLE 1-continued

Relationship Between Percentage Ionic Association to Ion Concentration

| % Ionic Association | mmol Fe | mmol Al | mmol Ca |
|---|---|---|---|
| 95 | 9.61 | 9.60 | 14.43 |
| 100 | 10.07 | 10.07 | 15.13 |

Figure 23:
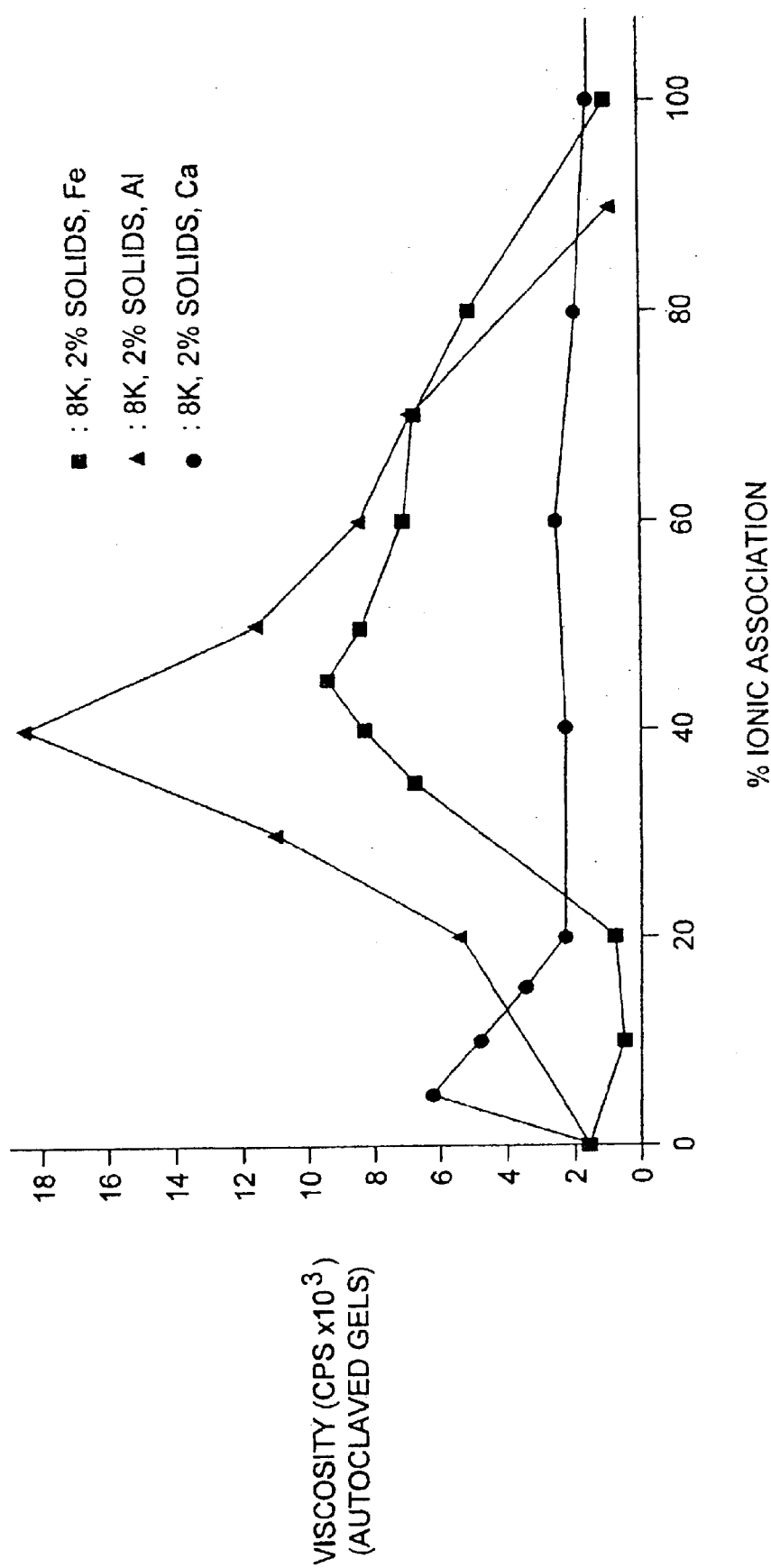
FIG. 23 depicts the relationship between the percent ionic association of CMC/PEO gels, the ionic composition and the viscosity of autoclaved gels of embodiments of this invention.

By way of example, increasing the concentration of $Fe^{3+}$ can increase the viscosity of the gel. However, this effect has a maximum at a concentration of $Fe^{3+}$ sufficient to produce a gel having between about 35% and about 50% of the theoretical maximum cross-linking, based on the availability of carboxyl groups (see Example 31). Further increases in cross-linking can decrease measured viscosity (see FIGS. 23 and 24 below). Similarly, for gels containing 1.33% solids, a CMC:PEO ratio of 97:3, and with PEO of molecular weight of 8 kd, $Ca^{2+}$ and $Al^{3+}$ have a concentration dependence which has a maximum. However, the maximum for $Ca^{2+}$ is only at around 5% of the total theoretical cross-linking, and $Al^{3+}$ has a maximum at around 45% of the theoretical maximal cross-linking (FIG. 23).

Gels having high solids %, or high degrees of cross-linking, such as those made using trivalent cations in the concentration range providing maximal ionic association can dissolve more slowly than gels made with lower ion concentration and/or with ions having lower valence numbers. Such gels can be used advantageously during recovery from surgery to ligaments and tendons, tissues which characteristically heal slowly. Thus, a long-lasting composition could minimize the formation of adhesions between those tissues.

F. Properties of Ionically Cross-Linked Polyacid Polyalkylene Oxide Compositions 1. Residence Time, Viscosity, and Composition of Polyacid Polyalkylene Oxide Compositions For the ionically cross-linked compositions of this invention to be effective at decreasing adhesions, the material should remain at the site for a sufficiently long time to permit tissue repair to occur while keeping the tissues separated. The tissues need not completely heal to reduce the incidence of adhesions, but rather, it can be desirable for the composition to remain during the immediate postsurgical period. The time that a composition remains at a tissue site can depend on the ability of the composition to adhere to the tissue, a property termed "bioadhesiveness."

Bioadhesiveness is defined as the attachment of macromolecules to biological tissue. Bioadhesiveness is important in preventing surgical adhesions because the potential barrier must not slip away from the surgical site after being placed there. Both CMC and PEO individually are bioadhesive (e.g., see Bottenberg et al., *J. Pharm. Pharmacol* 43: 457–464 (1991)). Like other polymers which are known to swell when exposed to water, CMC/PEO gels and membranes are also bioadhesive.

Hydration contributes to bioadhesiveness (Gurney et al, *Biomaterials* 5:336–340 (1984); Chen et al., *Compositions Producing Adhesion Through Hydration, In: Adhesion in Biological Systems*, R. S. Manly (Ed.) Acad. Press NY (11970), Chapter 10). A possible reason for this phenomenon could be that with increased hydration, more charges on the polyacid become exposed, and therefore may be made available to bind to tissue proteins. However, excessive hydration is detrimental to bioadhesion. Thus, a means of controlling the bioadhesiveness of gel compositions and membranes is to control their hydration properties.

Bioadhesiveness can depend on the viscosity of the gel and/or the charge density. A possible mechanism could be that positively charged sites, introduced by way of multivalent cations or polycations, may interact with negatively charged sites on the tissues. However, other mechanisms may be responsible for the phenomena, and the invention is not limited to any particular theory or mechanism. The gels made according to the invention have unexpected properties which were not anticipated based on prior art. We have unexpectedly found that the addition of polyvalent cations to mixtures of polyacids and polyalkylene oxides can increase the viscosity above that expected on the basis of the polyacid and polyalkylene oxide alone. Furthermore, we have unexpectedly found that the addition of polyethers to mixtures of polyacids and polyvalent cations increases the viscosity above that predicted on the basis of the polyacid and ions alone. Additionally, the results are unexpected based on the lack of increase in viscosity of polyalkylene oxide solutions with the addition of ions. This synergism between polyacid/polyether and polyvalent cations can provide a wider range of biophysical properties of the compositions than were previously available.

In addition to altering the ion concentration and valence of the ions of the association complex, increased intermacromolecular association can be achieved using polyacids with increased numbers of acid residues. By increasing the numbers or density of acidic residues on the polyacid, there is increasing likelihood of ionic bond formation even at a relatively low pH. The degree of substitution ("d.s") must be greater than 0, i.e., there must be some acid residues available for ionic bond formation. However, the upper limit is theoretically 3 for cellulose derivatives with carboxylic acids, wherein for each mole of the saccharide, 3' moles of carboxyl residues can exist. Thus, in the broadest application of the invention for CPS, the d.s. is greater than 0 and up to and including 3. Preferably, the d.s. is between 0.3 and 2. CPS with d.s. between 0.5 and 1.7 work well, and CPSs with a d.s. of about 0.65–1.45 work well and are commercially available.

The viscosity of a gel can depend on the molecular weight of the PA. With increased molecular weight, there can be more acidic residues per mole of PA, and therefore more opportunities for ionic interaction to occur with other molecules in solution. Additionally, the increased molecular weight produces longer PA chains which can provide greater opportunities for entanglement with nearby polymers. This can lead to a more entangled polymer network. Therefore, in embodiments in which the polyacid is a CPS, the molecular weights of the carboxypolysaccharide can vary from 10 kd to 10,000 kd. CPS in the range of from 600 kd to 1000 kd work well, and CPS of 700 kd works well, and is easily obtained commercially.

2. Resorption of Ionically Cross-Linked Polyacid Polyalkylene Oxide Compositions The gel complexes of the instant invention are intended to have a finite residence time in the body. Once placed at a surgical site, the compositions are designed to serve as a barrier for a limited time period. Once healing has substantially taken place, the anti-adhesion barrier naturally disintegrates, and the components are cleared from the body.

The degradation and rate of solubilization and disruption of the compositions can be manipulated by careful adjustment of the ionic composition and concentration during formation of the association complexes, by varying the PA/PO ratio, and by selecting the appropriate degree of substitution of the PA and molecular weights of the PO and PA. Decreasing the molecular weight of CPS increases its solubility. (Kulicke et al., Polymer 37(13): 2723–2731 (1996). The strength of the gel or membrane can be tailored to the surgical application. For example, certain surgical applications (e.g., spine or tendon) may require a stronger, more durable materials than others (such as intraperitoneal applications). Manipulation of the above-mentioned experimental variables allows the manufacture and use of products with variable residence times in the body.

3. Sterilization of Polyacid Polyalkylene Oxide Compositions

After their manufacture, gels and membranes of this invention can be packaged and sterilized using steam autoclaving, ethylene oxide, γ-radiation, electron beam irradiation or other biocompatible methods. Autoclaving can be carried out using any suitable temperature, pressure and time. For example, a temperature of 250° F. for 20 minutes is suitable for many preparations. For preparations that should not be exposed to water vapor in an autoclave, the compositions, including dried membranes and/or sponges can be irradiated with gamma radiation. In certain embodiments, the intensity of radiation is in the range of about 1 megaRad ("MRad") to about 10 MRad, alternatively, about 2 MRad to about 7 MRad, in other embodiments about 2.5 MRad, or in other embodiments, about 5 MRad. Gamma irradiation can be performed using, for example, a device from SteriGenics, Corona, Calif. We observed that sterilization procedures can alter the chemical and physical properties of the compositions and their individual components and thereby can increase the bioresorption of the compositions.

III. Incorporation of Drugs into Compositions

Ionically cross-linked gels and membranes can be made which incorporate drugs to be delivered to the surgical site. Incorporation of drugs into membranes is described in Schiraldi et al., U.S. Pat. No. 4,713,243. The incorporation may be at either the manufacturing stage or added later but prior to insertion. Drugs which may inhibit adhesion formation include antithrombogenic agents such as heparin or tissue plasminogen activator, drugs which are anti-inflammatory, such as aspirin, ibuprofen, ketoprofen, or other, non-steroidal anti-inflammatory drugs. Furthermore, hormones, cytokines, osteogenic factors, chemotactic factors, proteins and peptides that contain an arginine-glycine-aspartate ("RGD") motif, analgesics or anesthetics may be added to the compositions, either during manufacture or during conditioning. Any drug or other agent which is compatible with the compositions and methods of manufacture may be used with the present invention.

IV. Uses of PA/PO Compositions

The types of surgery in which the membrane and/or gel compositions of the instant invention may be used is not limited. Examples of surgical procedures include abdominal, ophthalmic, orthopedic, gastrointestinal, thoracic, cranial, cardiovascular, gynecological, arthroscopic, urological, plastic, musculoskeletal, otorhinolaryngological and spinal.

Between 67% and 93% of all laparotomies and laparoscopies result in adhesion formation. Specific abdominal procedures include surgeries of the intestines, appendix cholecystectomy, hernial repair, lysis of peritoneal adhesions, kidney, bladder, urethra, and prostate.

Gynecological procedures include surgeries to treat infertility due to bilateral tubal disease with adhesions attached to ovaries, fallopian tubes and fimbriae. Such surgeries including salingostomy, salpingolysis and ovariolysis. Moreover, gynecological surgeries include removal of endometrium, preventing de-novo adhesion formation, treatment of ectopic pregnancy, myomectomy of uterus or fundus, and hysterectomy.

Musculoskeletal surgeries include lumbar, sacral, thoracic and cervical laminectomy, lumbar, sacral, thoracic and cervical discectomy, flexor tendon surgery, spinal fusion and joint replacement or repair, and other spinal procedures.

Thoracic surgeries which involve sternectomy or thoracotomy can be hazardous after primary surgery because of adhesion formation between the heart or aorta and sternum. Thoracic surgeries include bypass anastomosis, and heart valve replacement.

Because many cranial surgical procedures require more than one procedure, adhesions involving the skull, dura, cortex, sinus cavities and ear can complicate the secondary procedures.

Ocular surgical uses include strabismus surgery, glaucoma filtering surgery, and lacrimal drainage system procedures.

Additionally, the compositions of this invention are useful for the prevention of de novo adhesions and reformation of adhesions, at local sites and at sites remote from the immediate site of the procedure.

In addition to surgical uses, the membrane and/or gel compositions of this invention can be readily used to reduce adhesions and to promote healing following traumatic injury or a disease process in which adhesions can form and thereby limit the ability of the healed tissue to function properly. Examples of injuries include puncture wounds, cuts and abrasions. Examples of diseases include arthritis, abscesses and autoimmune diseases.

For example, injection of the compositions of this invention can decrease the severity of arthritic conditions and joint inflammation. Additionally, arthroscopic procedures can benefit from the use of the gels of this invention. In arthroscopy, the surgeon visualizes the interior of a joint through a small diameter endoscope inserted into the joint through a small incision. The joint may be operated upon through similar incisions using fiber optic endoscopic systems. Further, diagnostic arthroscopy can be used in the temporomandibular, shoulder, elbow, wrist, finger, hip, and ankle joints. Surgical arthroscopic procedures include synovectomy, chondroplasty, removal of loose bodies and resection of scar tissue or adhesions. Additionally, compositions can be injected directly into joints for synovial fluid supplementation. Moreover, the compositions of this invention can be used as tissue lubricants or to lubricate surgical instruments prior to or during use.

Additional uses for the compositions of this invention include uses as lubricants for insertion of medical instruments such as catheters, and to decrease the trauma caused by medical instruments and devices. By coating the surface of the instrument or device prior to use, the friction of the device against tissues can be decreased. Decreasing trauma can lessen the tendency for medical instruments to promote formation of unwanted adhesions.

V. General Methods For Testing And Evaluating Antiadhesion Membranes

A. Hydration Ratio of Membranes

To determine the rate of hydration and the hydration ratio of membranes, pieces of dry membranes, preferably 160 mg, were placed singly in a glass vial and 20 ml phosphate buffered saline solution (PBS, 10 mM, pH 7.4, Sigma Chemical Company, St. Louis, Mo.) was added. The membranes hydrate, creating soft sheets of hydrogel. After a certain time period (typically 1 hr to 5 days), each of the hydrated membranes was carefully removed from the test vial and placed in a polystyrene petri dish. Excess water was removed using a disposable pipette and by blotting the membrane with tissue paper. Each membrane was then weighed and the hydration ratio (% H) was determined according to the following formula:

$$\% \, H = \frac{(\text{wet mass} - \text{dry mass})}{\text{dry mass}} \times 100 \, \%.$$

B. Solubility of Membranes

To determine the solubility of membranes, we measured the relative solubility in water and the aqueous stability of the membranes as a function of their chemical compositions. Membrane solubility in water correlates with the resorption time of the membranes in-vivo.

Typically, the test is performed in conjunction with the hydration measurements outlined above. However, the membranes take up salt during the hydration test due to exposure to PBS. This added salt results in an artifactually high dry weight. Therefore, after determining the hydration ratio, we soaked the membranes in deionized water (30 ml for 30 min.) to remove the salt incorporated in the polymer network. The water was decanted and a fresh 30 ml aliquot of deionized water was added. The membranes were allowed to soak for another 30 min., were taken out of the petri dishes, were blotted dry and were placed in a gravity convection oven at 50° C. to dry.

The drying time was dependent on the amount of water absorbed by the membrane. Highly hydrated, gel-like membranes took up to 24 hours to dry whereas partially hydrated membranes took as little as a few hours to dry. After the membranes lost the excess water, the membranes were allowed to equilibrate at room temperature for 1–2 hours before weighing them. The weight measurements were repeated until a constant weight was obtained. Typically, some rehydration of the membrane took place during this period due to adsorption of moisture from the air.

After the desalinization process described above, the membranes were placed in petri dishes containing 30 ml deionized water to hydrate for periods of from 20 minutes to 5 days. Preliminary studies showed that membranes at pH within the range of 6 and below did not disintegrate during the 1 hr desalinization period.

The solubility (S) of membranes was calculated using the following formula:

$$\% \, S = \frac{(\text{dry mass before soaking} - \text{dry mass after soaking})}{\text{dry mass before } PBS \text{ soaking}} \times 100 \, \%.$$

The dry mass before soaking is the mass after desalinization, and the dry mass after soaking is the mass after the hydration period in water.

C. Determination of Acid Load Delivered by Membranes

This test was performed in conjunction with the hydration and solubility tests described above. The test gives an indication of the acid load which the membrane could deliver to a tissue when placed implanted in an animal or human subject. After manufacture, the membranes were placed in a PBS solution, the complex released protons in a time-dependent way resulting in a measurable decrease in pH of the PBS solution.

The acid load test was performed using a Model 40 pH meter (Beckman Instruments, Fullerton, Calif.). 160 mg of dry membrane was placed in a glass vial and 20 ml PBS was added. The initial pH of the PBS solution was 7.40; the pH of this solution was gradually decreased as the polymers in the membrane partly dissolved thereby exposing more protonated carboxylic residues. In highly hydrated membranes (pH 4–7) this process was accelerated as the polymer chains were pulled apart by the hydrostatic forces generated during the hydrating process.

VI. EXAMPLES

In the following examples, carboxypolysaccharide/polyether membranes and ionically cross-linked gel compositions are described for CMC as an exemplary carboxypolysaccharide, and PEO is the exemplary polyether. It is understood that association complexes of other carboxypolysaccharides, other polyacids, polyethers and other polyalkylene oxides can be made and used in similar ways. Thus, the invention is not limited to these Examples, but can be practiced in any equivalent fashion without departing from the invention.

Example 1

Neutral CMC/PEO Membranes

Type 7HF PH (MW approximately 700 kd; lot FP 10 12404) carboxymethylcellulose sodium (CMC) was obtained from the Aqualon Division of Hercules (Wilmington, Del.). PEO with a MW of approximately 900 kd was obtained from Union Carbide (Polyox WSR-1105 NF, lot D 061, Danbury Conn.); PEO with a MW of approximately 1000 kd was obtained from RITA Corporation (PEO-3, lot 0360401, Woodstock, Ill.).

A membrane with a composition of 65% CMC and 35% PEO was made as follows: 6.5 g of CMC and 3.5 g of PEO was dry blended in a weighing dish. A Model 850 laboratory mixer (Arrow Engineering, PA) was used to stir 500 ml of deionized water into a vortex at approximately 750 RPM. The dry blend of CMC and PEO was gradually dispersed to the stirred water over a time period of 2 min. As the viscosity of the polymer solution increased as the polymers dissolved, the stirring rate was gradually decreased. After approximately 15 min., the stirring rate was set at between 60–120 RPM and the stirring was continued for approximately 5 h to obtain a homogeneous solution containing 2% total polymer concentration (wt/wt) without any visible clumps.

Instead of pre-blending the CMC and PEO, an alternative way of formulating the casting solution for the membranes is to individually dissolve the polymers. The anionic polymer, CMC, can be then acidified by adding the appropriate amount of HCl. For example, a 500 ml batch of 2% CMC made by dissolving 10.0 g of CMC 7HF in 500 ml deionized water was acidified to a pH of 2.6 by adding 2700 $\mu l$ concentrated HCl ("solution A"). Separately, a batch of 2% PEO was made (w/v 900,000 MW, "solution B"). Solutions A and B are then thoroughly mixed in a specific ratio using the laboratory stirrer of Example 1 at 60 RPM. The total polymer concentration was kept at 2% (w/v), as in Examples 1–2.

Membranes were cast from solutions by pouring 20 g of solution into 100×15 mm circular polystyrene petri dishes (Fisher Scientific, Santa Clara, Calif. The petri dishes were placed in a laboratory gravity convection oven set at 40°–45° C., and were allowed to dry overnight at about 760 Torr. The resulting membranes were carefully removed from the polystyrene surface by using an Exacto knife.

For larger membranes, 243×243×18 mm polystyrene dishes (Fisher Scientific) were used. Using the same weight to surface area ratio as for the circular membranes (in this case, 220 g of casting solution was used), resulted in a membrane which had a dry weight of approximately 4.5 g. The membrane appeared homogeneous, smooth, and pliable. Placing 160 mg of this membrane in 20 ml of a PBS solution (pH 7.4) did not change the pH of the solution. The dry tensile strength and % elongation at break were slightly higher than corresponding membranes which were made from an acidified casting solution (Table 2). When placed in deionized water or PBS, the membrane exhibited excessive swelling and lost its sheet structure rapidly (within 10 min.) to form a gel-like substance which eventually homogeneously dispersed into a polymer solution.

Example 2

Moderately Acidified CMC/PEO Membranes and Hydrogels

The procedure for making acidified membranes in the intermediate pH region (2.5<pH<7) initially follows the procedure outlined in Example 1. The neutral blended polymer solution containing the polymers specified in Example 1 is acidified by adding concentrated hydrochloric acid (HCl, 37.9%, Fisher Scientific, Santa Clara, Calif.) while stirring the polymer solution at 60–120 RPM for 1 hour. Initially, a white precipitate forms in the solution; the precipitate gradually disappears and a stable solution is formed. Typically, a 2% total polymer concentration was found useful to achieve the desired viscosity for stable casting solutions. Higher polymer concentrations resulted in polymer solutions which were too viscous and too difficult to pour. Lower polymer concentrations required more casting solution for the same membrane weight which greatly increased drying time for equivalent membranes. In the 500 ml 65% CMC/35% PEO polymer blend of Example 1, 1500 $\mu l$ of concentrated HCl is needed to achieve a pH of 3.1 in the casting solution. The viscosity of the starting polymer solution dropped by at least 50% by this acidification process.

The titration curves for various polymer blends (as well as 100% CMC and 100% PEO) are shown in FIG. 2. FIG. 2 shows the amount of HCl needed to make casting solutions of desired pHs depending upon the composition of the CMC/PEO mixture. Membranes made of 100% CMC (■) require more acid than do other compositions to become acidified to the same degree. Increasing the concentration of PEO (decreasing the concentration of CMC) decreases the amount of acid necessary to acidify a casting solution to a desired point. Increasing the PEO concentration to 20% has a small effect, regardless of whether the molecular weight of the PEO is 200 k (●) or 1000 kd (▲). Increasing the PEO concentration to 40%(+) or to 100% (□) further decreases the amount of acid needed to achieve a desired casting solution pH.

A. Viscosity of Hydrogels

Because the antiadhesion properties of a hydrogel are dependent upon its viscosity, we determined the relationship between casting solution pH and the viscosity of the hydrogel. We determined the viscosity of PCS/PE solutions at 22° C. using a Brookfield™ viscometer. Using methods published in the brochure *Cellulose Gum*, Hercules, Inc., Wilmington, Del., (1986), page 28. Briefly, the composition of the solution to be tested is selected, and by referring to Table XI on page 29 of Cellulose Gum, the spindle number and spindle revolution speed is selected. Viscosity measurements are made within 2 hr after stirring the solution. After placing the spindle in contact with the solution, and permitting the spindle to rotate for 3 minutes, the viscosity measurement is read directly in centipoise on a Brookfield Digital Viscometer (Model DV-II). We studied 65% CMC/35% PEO solutions made with 7HF PH CMC and 1000 kd PEO at a pH of 7.5. Another 65% CMC/35% PEO solution was made at a pH of 3.1

TABLE 2

Effect of Casting Solution pH on Hydrogel Viscosity

| RPM | Viscosity @ pH 7.5, 22° C. (centipoise) | Viscosity @ pH 3.1, 22° C. (centipoise) |
|---|---|---|
| 0.5 | 38,000 | 13,000 |
| 1.0 | 31,000 | 12,000 |
| 2.0 | 23,200 | 10,400 |
| 5.0 | 19,400 | 8,800 |
| 10 | 15,500 | 7,300 |

Table 2 shows the change in viscosity due to acidification of casting solutions. Reducing the pH from 7.5 to 3.1 decreased the viscosity of the casting solution by more than half. Because the viscosity of a hydrogel is related to its ability to prevent adhesions, possibly due to its ability to remain in one site for a longer time period, gels of higher pH have greater anti-adhesion properties. Further, it is also possible to characterize casting solutions by their viscosity as well as their pH. Thus, for situations in which the measurement of pH is not be as easy or reliable, measurements of viscosity are preferred. To make membranes, the acidified casting solutions containing the weakly H-bonded intermolecular PEO-CMC complex were next poured into polystyrene dishes and dried out in a similar way as described in Example 1. After drying, physical properties were determined.

B. Physical Properties of CMC/PEO Membranes:

Tensile strength and elongation of membranes are measured for pieces of membrane in the shape of a "dog bone," with a narrow point being 12.7 mm in width. The membranes are then mounted in an Instron™ tester equipped with a one ton load cell. The crosshead speed is set at 5.0 mm/min. We measured membrane thickness, tensile strength, and elasticity (% elongation of the membrane at the break point). Results are reported for those samples that had failure in the desired test region. Those samples that either failed at the radius of the sample or in the grips were considered improper tests and results of those tests were discarded.

TABLE 3

Physical Properties of CMC/PEO Membranes

| Membrane Composition | Thickness (mm) | Tensile Strength (psi) | % Elongation at Break Point |
|---|---|---|---|
| 65% CMC/35% PEO (1000 kd) pH 3.1 | 0.081 | 6017 | 4.17 |
|  | 0.076 | 5527 | 4.47 |
|  | 0.076 | 5956 | 5.07 |
| 65% CMC/35% PEO (1000 kd) pH 7.5 | 0.071 | 10,568 | 6.69 |
|  | 0.069 | 10,638 | 6.61 |
| 80% CMC/20% PEO (5000 kd) pH 3.1 | 0.084 | 3763 | 3.20 |

The membranes are all less than 0.1 mm thick. Table 3 shows that decreasing the pH of the membrane from neutral decreases the tensile strength, and decreases the elasticity (% elongation) at the break point. Similarly, decreasing the PEO concentration decreases the tensile strength and elasticity of the membranes.

C. Hydration of CMC/PEO Membranes in PBS

To evaluate the bioadhesive properties of membranes, we determined the rate and extent of hydration properties of CMC/PEO membranes according to the methods described above.

FIG. 3 shows the time course of hydration of CMC/PEO membranes of the present invention. A membrane made of 80% CMC/20% PEO (m.w. 900 kd) at a pH of 4.31 rapidly hydrated (●). After 2 h in PBS, its hydration ratio (wet wt.–dry wt)/dry wt; % swelling) increased to more than 6000%. After 5 h in PBS, this membrane's hydration ratio was nearly 8000%. This highly hydrated membrane lost its cohesiveness and substantially disintegrated thereafter. Reducing the membrane pH to 3.83 and below resulted in membranes which hydrated nearly to their equilibrium points within 2 hrs. and maintained their degree of hydration and cohesiveness for at least 40 hrs. The degree of hydration was dependent upon the membrane pH with the least acidic membranes being capable of swelling to a higher degree. At a pH of 3.83 (A), the membrane had a hydration ratio of nearly 6000%, whereas at a pH of 2.0 (E), the hydration ratio was less than 300%. Within the range of pH from 3.2 to 4.3, the degree of hydration is very sensitive to the pH.

Figure 4:
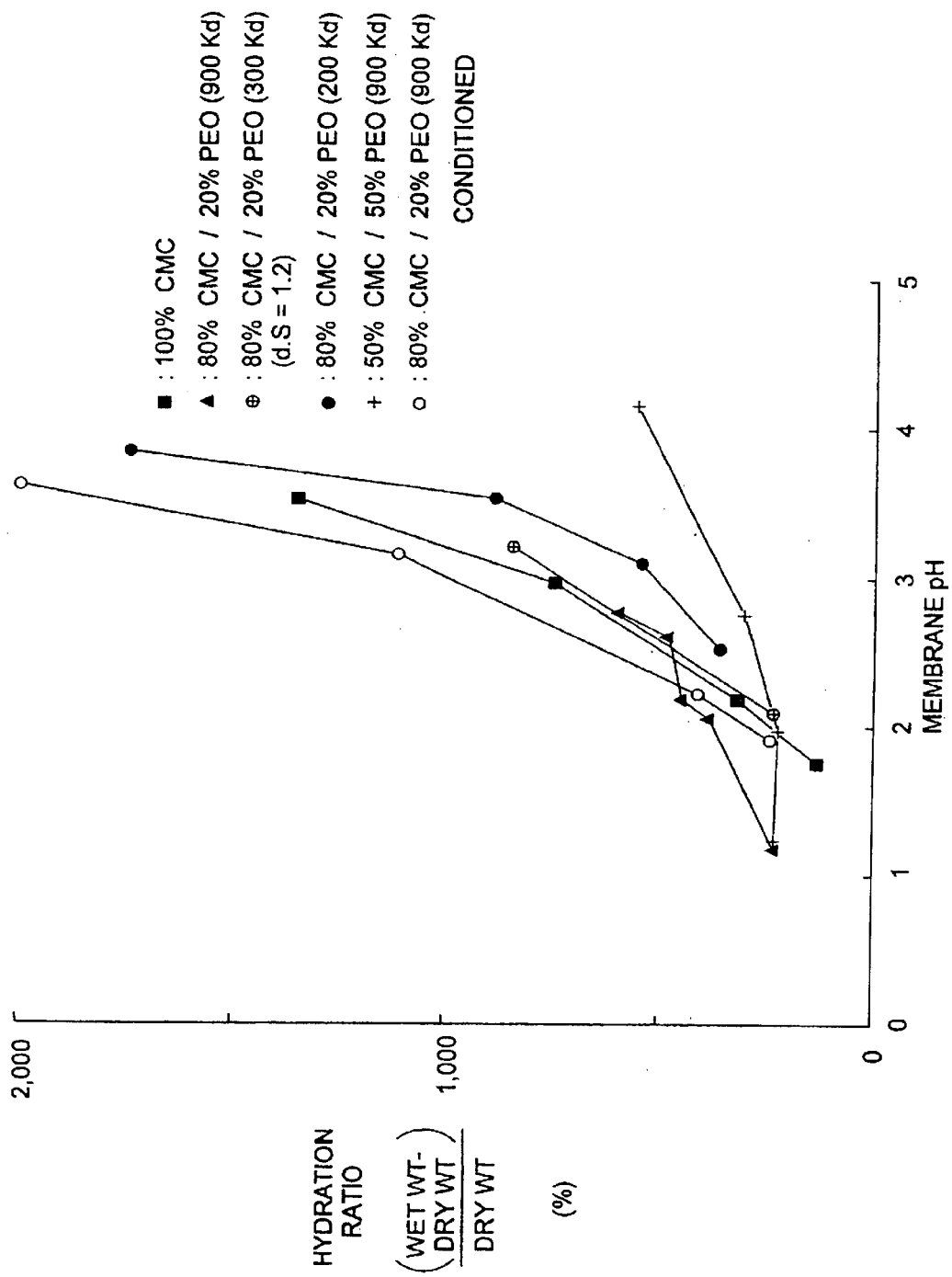
FIG. 4 shows the hydration or swelling of CMC/PEO membranes in phosphate buffered saline (PBS) solution with a pH of 7.4 at room temperature.

FIG. 4 shows a summary of another study of the effect of membrane composition and pH on the hydration of CMC/PEO membranes. Hydration was measured after at least 6 hrs in PBS, a time after which the degree of hydration had nearly reached equilibrium for each membrane (see FIG. 3). For each of the compositions studied, increasing the membrane pH increased the hydration of the membrane. Membranes of 100% CMC (■) increased their hydration ratios from approximately 100% at a membrane pH of 1.7 to over 1300% at a membrane pH of 3.4. For membranes made of 80% CMC/20% PEO, the molecular weight of the PEO had a slight effect on hydration. Membranes made with 900 kd PEO (▲), hydrated slightly more at a given pH than membranes made with 200 kd PEO (●). Furthermore, membranes made with CMC of a higher degree of substitution (d.s.=1.2; ⊕) hydrated similarly to those of 100% CMC with a degree of substitution of 0.84 (■). Finally, membranes that were made with 50% CMC/50% PEO (900 kd) hydrated less than any of the other membranes, except at low membrane pH (<2.5).

D. Solubility of CMC/PEO Membranes

Because the biodegradation of CPS/PE polymers is related to solubility, we measured the solubility of membranes after at least 4 days in PBS according to methods described above. FIG. 5 shows the effects of membrane pH and composition on the solubility of membranes in PBS solution. Membranes were made of different CMC/PEO compositions and at different membrane pHs. For all membranes, as the membrane pH increased, the solubility in PBS increased. Membranes of 100% CMC (■) were the least soluble. Membranes containing PEO were more soluble, with membranes made of 900 kd PEO (▲) being less soluble than membranes of 200 kd PEO (●). Further increasing the percentage of PEO to 50% (+) further increased membrane solubility. Decreasing the molecular weight of the CMC (7MF;*) increased the solubility. Additionally, increasing the degree of substitution of the CMC from 0.84 to 1.12 (⊕) resulted in even more soluble membranes. Also, with the higher degree of substitution, there was a larger effect of pH on membrane solubility. For the other membranes, the effect of increasing pH appeared to be of similar magnitude regardless of the composition of the membrane. Thus, the slopes of the lines were similar. These results indicate that regardless of membrane composition, the solubility of membranes can be increased by increasing the membrane pH. Moreover, because bioresorption requires solubilization, more highly soluble membranes will be cleared from the body more rapidly than less soluble membranes.

E. Biocompatability of CMC/PEO Membranes

Because biocompatability is related to the acid load delivered to a tissue, we determined the acid load delivered by CMC/PEO membranes to a PBS solution as described above as a suitable in-vitro model. We first determined the time course of acidification of PBS solutions exposed to different compositions of CMC/PEO membranes.

TABLE 4

Time Course of Acidification of PBS by CMC/PEO Membranes

| Membrane Composition | Casting Solution pH | Time in PBS Solution (hr) | | | | 45 h PBS pH Change |
|---|---|---|---|---|---|---|
| | | 1 | 3.5 | 21 | 45 | |
| 80% CMC/ 20% PEO (900 kd) | 1.85 | 6.26 | 5.62 | 4.78 | 4.64 | 2.76 |
| | 3.17 | 6.53 | 5.71 | 5.61 | 5.65 | 1.75 |
| 50% CMC/ 50% PEO (900 kd) | 1.77 | 6.60 | 6.12 | 5.62 | 5.42 | 1.98 |
| | 2.71 | 6.47 | 6.13 | 6.01 | 5.98 | 1.42 |
| 80% CMC/ 20% PEO (8 kd) | 1.82 | 3.71 | 3.39 | 3.52 | 3.45 | 3.95 |

Table 4 shows the kinetics of acidification of a PBS solution by CMC/PEO membranes of the instant invention. When added to a PBS solution, membranes released acid into the solution, thereby lowering the solution pH. This process occurred slowly, with a reduction in solution pH of approximately 1 pH unit in the first hour for membranes including those combining high molecular weight PEO. This is true for membranes cast from low pH polymer solutions as well as those cast from higher pH polymer solutions. The remaining reduction in pH occurred over the next 20 hrs, at which time the solution pH remained approximately constant. By 45 hrs in the PBS solution, the pHs have decreased to below 6.0.

Additionally, as the molecular weight of the PEO decreased, the solution pH decreased more rapidly and to a higher degree than membranes made of high molecular weight PEO. This finding might be due to an ability of higher molecular weight PEOs to shield the acidic carboxyl residues of the CMC, thereby decreasing the dissociation of carboxyl hydrogen ions.

These results suggest that high molecular weight PEO acts to slow the delivery of acid to tissues, and thus, protects them from excessive acidification. Moreover, as protons are released in vivo, they will be diluted in the extracellular spaces, buffered by physiological buffers, and ultimately cleared from the tissue by the lymphatic and circulatory systems. Over the relatively long time during which protons are released, the physiological dilution, buffering, and clearance mechanisms will remove the acid load, keeping the pH at the tissue within acceptable ranges. Thus, these membranes are suitable for implantation in vivo without causing excessive tissue disruption due to a large acid load being delivered.

FIG. 6 shows the results of studies in which the pH of the PBS solution varies as a function of the membrane pH and composition of the membrane. Membranes were placed in PBS solution for 4–5 days, times at which the acidification had reached equilibrium (Table 4). The membrane composition which resulted in the least acidification were the pre-conditioned 80/20/300 k membranes (O). These membranes were made as described above, except for an additional step of soaking the membranes in PBS and then re-drying them (see Examples 7–9). The 80/20/200 k membranes cast in PBS (+) delivered the next lowest acid load, and the 50/50 CMC/PEO (900 k) series of membranes (Δ) delivered the third lowest acid load to the PBS solution. Membranes made of 100% CMC: (■), 80/20/200 k (●), and the 80/20/900 k (▲) delivered progressively more acid to the PBS, and the 80/20/300 k series of membranes made with CMC with a degree of substitution of 1.12 delivered the most acid to the PBS solution.

FIG. 6 also shows that conditioning membranes by soaking them in PBS decreased the acid load delivered to the PBS solution. For example, a pre-conditioned membrane cast at an original pH of 3.4 reduced the pH of the PBS solution only to 7.0 from 7.4. Thus, for those applications in which a long lasting membrane is needed, but one which will cause the least acidification, preconditioning of an acidic membrane in PBS is desirable.

Example 3

Membranes With Different PEO/CMC Ratios

A 500 ml batch of a 80/20 CMC/PEO membrane was obtained by dissolving 8.0 g CMC and 2.0 g PEO in 500 ml deionized water (source of CMC and PEO, and solution processes were as in Example 1). While stirring at low speed (60 RPM), 200 g of this polymer solution was acidified with 1500 μl of 5 N HCl (LabChem, Pittsburgh, Pa.), resulting in an equilibrium pH of 3.17. The acidified polymer solution was next poured into polystyrene dishes and dried out in a similar way as described in Example 1. By changing the relative amounts of CMC and PEO, membranes with different compositions were obtained. 100% CMC membranes were more brittle and less flexible than PEO-containing membranes. For our purposes, membranes which contain more than 70% PEO are generally not preferable as these membranes were unstable in an aqueous environment.

TABLE 5

Viscosity of Solutions With Different CMC/PEO Ratios (cps, @ Spindle #6, 20° C.)

| Membrane Composition (1000 kd PEO) (% CMC/% PEO; pH) | Spindle RPM | | | | |
|---|---|---|---|---|---|
| | 0.5 | 1.0 | 2.5 | 5.0 | 10.0 |
| 25/75 | | | | | |
| 4.0 | 8000 | 7000 | 4800 | 4400 | 3700 |
| 2.6 | 3200 | 3000 | 2800 | 2400 | 2000 |
| 33/66 | | | | | |
| 4.0 | 8000 | 7000 | 6800 | 6200 | 5100 |
| 2.6 | — | 3000 | 3200 | 2800 | 2500 |
| 50/50 | | | | | |
| 4.0 | 16,000 | 15,000 | 12,800 | 10,600 | 8400 |
| 2.6 | 4000 | 5000 | 4800 | 4200 | 3500 |
| 66/33 | | | | | |
| 4.0 | 28,000 | 25,000 | 20,400 | 16,000 | 12,300 |

TABLE 5-continued

Viscosity of Solutions With Different CMC/PEO Ratios
(cps, @ Spindle #6, 20° C.)

| Membrane Composition (1000 kd PEO) (% CMC/% PEO; pH) | Spindle RPM | | | | |
|---|---|---|---|---|---|
| | 0.5 | 1.0 | 2.5 | 5.0 | 10.0 |
| 2.6 100% CMC | 8000 | 7000 | 6400 | 5800 | 4900 |
| 4.0 | 72,000 | 61,000 | 42,800 | 31,600 | 28,700 |
| 2.6 | 88,000 | 67,000 | 42,400 | 29,400 | 20,400 |
| 100% PEO (900 kd) 2.6 | 480 | 300 | 280 | 290 | 290 |

Table 5 shows the effect of CMC/PEO ratio on solution viscosity. Membranes were made with different percentages of PEO (m.w.: 1,000,000) at two different pHs. Solutions containing higher proportions of CMC were more viscous than solutions containing less CMC. Furthermore, the less acidic solutions had a higher viscosity than solutions with more acidity. This relationship held for all solutions except for the 100% CMC solution. At a pH of 2.6, the viscosity was slightly higher than at a pH of 4.0. This was possibly due to the association between CMC molecules at lower pH.

Larger than expected viscosity decreases were obtained when the two solutions were mixed. For example, an 85% loss in viscosity was achieved when solutions A (pH 2.6) and B were mixed in a 50/50 ratio. At a spindle RPM of 2.5, the starting 2% CMC concentration (w/v), pH 2.6 solution had a viscosity of 42,400 cps, the 2% PEO solution had a viscosity of 280 cps. Thus, if viscosity of a mixture is the average of the viscosities of the components, we would expect that a 50/50 CMC/PEO solution would have a viscosity of (42400+280)2=21300 cps (approximately a 50% viscosity decrease from that of CMC alone). However, the actual CMC/PEO (50/50) solutions had a viscosity of only 4,800 CPS. A similar, more than expected decrease in viscosity was reported by Ohno et al. (*Makromol. Chem., Rapid Commun.* 2, 511–515, 198 1) for PEO blended with dextran and inulin.

Further evidence for intermolecular complexation between CMC and PEO is shown by comparing the relative decreases in viscosity caused by acidification for the 100% CMC and CMC/PEO mixtures. Table 5 shows at 2.5 rpm, the viscosity of CMC solution remained essentially unchanged when the pH was decreased from 4.0 to 2.6. However, for mixtures of CMC/PEO, the acidification caused a large decrease in viscosity. The decreases were by 69%, 63%, 53%, and 42% for mixtures of CMC/PEO of 66%/33%, 50%/50%, 33%/66%, and 25%/75%, respectively.

Thus, there is an intermolecular association between CMC and PEO, which, we theorize, results in PEO molecules becoming interspersed between CMC molecules, thereby preventing intermolecular bonding between the CMC molecules. Such a theory could account for the observations, but we do not intend to limit the present invention to any single theory of molecular interaction. Other theories may account for the observations.

Next, after manufacturing membranes with different CMC/PEO ratios we studied their hydration, acid load, and solubility properties using methods described above.

TABLE 6

Effect of CMC/PEO Ratio on Hydration,
Acid Load and Solubility

| Membrane Composition (% CMC 7HF/ % PEO 900 kd) | Membrane pH | Hydration Ratio (%) | Acid Load (PBS pH) | Solubility (% Mass Loss) |
|---|---|---|---|---|
| 100% CMC | 2.52 | 1145 | 3.46 | 9.7 |
| 66/33 | 2.87 | 2477 | 3.80 | 30 |
| 50/50 | 2.94 | 3077 | 4.58 | 34 |
| 33/66 | 2.98 | (dissolved) | 5.88 | (dissolved) |

Table 6 shows the effect of increasing the PEO concentration in CMC-PEO membranes on the % water uptake, acidity, and mass loss. Increasing the PEO content of membranes increases the hydration ratio and solubility and decreases the acid load delivered to PBS. These results indicate that as the total amount of CMC in the membrane decreases, the acid load decreases.

The effect of a different CMC/PEO ratios is further demonstrated in FIG. 5 (solubility vs. membrane pH), and FIG. 6 (membrane acidity vs. PBS solution pH).

Example 4

Membranes of Different Molecular Weight PEO

Membranes of PEO's of different molecular weight were made by mixing 2% (w/v) PEO solutions with 2% (w/v) solutions of CMC (type 7HF PH (lot FP 10 12404) obtained from the Aqualon Division of Hercules (Wilmington, Del.). PEO's with a molecular weight of 8000 (8K) was obtained as Polyglycol E8000NF from Dow Chemical, Midlands, Mich. The PEO's with molecular weights of 300,000 (300K), 900,000 (900K), and 5,000,000 (5M) were all from Union Carbide. 2% (w/v) solutions of PEO were made by dissolving 6.0 g of PEO in 300 ml deionized water according to the methods used in Example 1. The CMC stock solution was similarly made by dissolving 10.0 g CMC in 500 ml deionized water. The CMC stock solution was acidified by adding 2100 Ill concentrated HCl to decrease the pH of the casting solution to 3.37.

A 50% CMC/50% PEO (8K) membrane was made by mixing 40.07 g of the CMC stock solution with 40.06 g of the PEO (8K) stock solution. The casting solution was acidified to a pH of 3.46. A 50% CMC/50% PEO (300K) membrane was made by mixing 39.99 g of the CMC stock solution with 40.31 g of the PEO (300K) stock solution and adding sufficient HCl to lower the pH to 3.45. A 50% CMC/50% PEO (900K) membrane was made by mixing 39.22 g of the CMC stock solution with 39.63 g of the PEO (900K) stock solution and adding sufficient HCl to lower the pH to 3.56. A 50% CMC/50% PEO (5M) membrane was made by mixing 38.61 g of the CMC stock solution with 40.00 g of the PEO (5M) stock solution and adding sufficient HCl to lower the pH to 3.55.

Membranes made from these various acidified CMC/PEO mixtures were cast and dried according to the methods given in Example 1. FIG. 7 shows the effect of the molecular weight of PEO on the hydration ratios of the resulting membranes. The results indicate that increasing the molecular weight of PEO increases the hydration ratio, although there was little increase in hydration by increasing the PEO molecular weight from 900 kd to 5000 kd. Further differences between the membranes made from various molecular weights of PEO's can be observed from the data presented in FIGS. 4–6.

Example 5

Membranes of Different Molecular Weight CMC

A 50% CMC/50% PEO membrane was made from CMC (type 7MF PH; lot FP 10 12939, obtained from the Aqualon Division of Hercules, Wilmington, Del.) and PEO with a molecular weight of 900,000 (Union Carbide). In contrast to the "high viscosity", type 7HF CMC, the 7 MF CMC has a much lower viscosity in solution. The average molecular weight of type 7 MF is approximately 250 kd as compared to 700 kd for the 7HF type CMC. 5.0 g of CMC and 5.0 g of PEO (900K) were pre-blended dry and then dissolved in 500 ml deionized water according to the methods of Example 1. The solution was acidified with 950 µl of concentrated HCl which reduced the pH to 3.48. A membrane made from 20.0 g stock casting solution. Other portions of the stock solution were used to make more acidic membranes (with casting solutions pH's of 3.07, 2.51, and 1.96). The membranes were cast and dried from these acidified solutions. After drying, the hydration ratio, mass loss, and acid load were determined as previously described. For these membranes having pH of 3.48, 3.07, and 2.51, the % mass loss and hydration ratio could not be determined because the membranes dissolved. The final pH of the PBS solutions for each membrane were 5.93, 5.33 and 5.20, respectively. The membrane made at a pH of 1.96 retained its coherency, and the % mass loss was 60% and the hydration ratio was 343%, and the pH of the PBS solution was 4.33. Comparing the low pH membrane with others (FIG. 5) shows that at a pH of 2.0, the membrane made of lower molecular weight CMC was the most soluble. Thus, the strength of the association complex is dependent upon the molecular weight of the CMC.

Example 6

CMC/PEO Membranes with a Different Degree of CMC Substitution

CMC/PEO membranes were made from CMC of type 99-12M31XP (lot FP10 12159, degree of substitution (d.s.) of 1.17, obtained from the Aqualon Division of Hercules, Wilmington, Del.) and from PEO with a molecular weight of 300,000 (Union Carbide). 200 ml of blended polymer solution was acidified with 600 ill of concentrated HCl to yield a stock solution with a pH of 4.07. 20.7 g of this casting solution was poured into a petri dish; the membrane was dried as described in Example 1. The rest of the stock solution was used to make membranes with increased acidity. The pHs of the casting solutions for those membranes were 3.31, 3.03, 2.73, 2.44, and 2.17, respectively.

FIGS. 4–6 show the properties of these membranes compared to others with different compositions of CMC and PEO. FIG. 4 shows that the hydration ratio of CMC with a degree of substitution of 1.12 (e) is similar to that of other CMC/PEO membranes with a hydration ratio of 836% water when placed in PBS for 4 days. However, there are differences in other measured properties. FIG. 5 shows that compared to the other membranes, the membranes made from CMC with the higher degree of substitution produce the most soluble membranes. FIG. 6 shows that membranes made from highly substituted CMC produce membranes which deliver the largest acid load to PBS. This is consistent with the idea that at any given pH, there are more hydrogen ions available for dissociation in these membranes made with higher d.s.

Example 7

Ammonia Conditioning of Membranes

To study the effects of alkali conditioning on CMC/PEO membranes, 3 pieces of dried membranes (approximately 160 mg, composition: 80% CMC (7HF PH)/20% PEO (300K or 5000 kd) were placed in a petri dish. 30 ml of 0.5 N ammonium hydroxide (made from 10×dilution of 5 N ammonia, LabChem, Pittsburgh, Pa.) was added, immersing the membranes. Once completely immersed, the membranes were allowed to soak for either 1 or 5 min. The membranes were then removed from the ammonia solution, the excess ammonia was blotted off with filter paper, and the membranes were placed in a gravity convection oven at 45° C. and allowed to dry. After drying and re-equilibrating at room temperature, the membrane's mass was determined. After drying, the membranes hydration ratio, acid load, and solubility were determined. Results are shown in Table 7.

TABLE 7

Effect of Ammonia Conditioning on CMC/PEO Membranes

| Membrane Composition 80% CMC/ 20% PEO | Treatment Control or 0.5N NH₃ | Hydration Ratio (%) | PBS pH; at 4 d | Mass Loss after NH₃ (%) | Mass Loss after PBS (4 d) (%) | Total Mass Loss (%) |
|---|---|---|---|---|---|---|
| 300 kd PEO pH 2.03 | Control | 258 | 4.33 | — | 29 | 29 |
|  | 1 min | 374 | 7.29 | 22 | 1 | 23 |
|  | 5 min | 368 | 7.29 | 22 | 0 | 22 |
| 300 kd PEO pH 2.45 | Control | 281 | 3.92 | — | 26 | 26 |
|  | 1 min | 551 | 7.23 | 21 | 7 | 28 |
| 5000 kd PEO, pH 3.1 | Control | 553 | 4.24 | — | 36 | 36 |
|  | 1 min | 4774 | 6.98 | 21 | 61 | 63 |

Table 7 shows that ammonia treatment substantially decreased the acid load delivered to a PBS solution. By extension, this effect would also decrease the acid load delivered to a tissue in vivo. Also, compared to other membranes delivering the same acid load to the PBS other solutions, ammonia-conditioned membranes have lower solubility, and thus, increased residence time in vivo. Therefore, it is possible to introduce antiadhesion membranes with long residence times which deliver little residual acid to tissues. In contrast, unconditioned membranes at a pH of approximately 7.0 rapidly disintegrate, and thus are of little value in preventing post surgical adhesions.

Treating the membrane after initial manufacture reduced the acid load of the membrane. Compared to the controls (not soaked in ammonia) in all cases the conditioning treatment increased the pH from approximately 4 to more neutral pH values. Compared to the controls, the conditioning treatment also increased the hydration ratio of the membranes. Whereas this hydration increase was relatively small for the two types of acidic membranes, the least acidic (pH 3.1 80% CMC/20% PEO (5M)) membrane swelled to a higher degree. The effect of the treatment therefore is dependent on the prior condition of the membrane. The total mass loss due to the ammonia conditioning in two cases (for the 80% CMC/20% PEO (300 kd) pH 2.03 membranes) is slightly lower than that of the controls. This unexpected result may be due to the initial loss of salt in the ammonia solution followed by a uptake of salt in the salt-depleted membranes during soaking in PBS.

Example 8

Conditioning Membranes Using Phosphate Buffer

Similar to Example 7, membranes were conditioned after manufacture in phosphate buffer (50 mM, pH 7.40). A piece of dry membrane (0.163 g; 80% CMC (7 HF PH)/20% PEO (5000 kd), pH 3.1) was placed in a petri dish. The membrane was soaked for 5 min in 30 ml of monobasic potassium phosphate/sodium hydroxide buffer (50 mM, pH 7.40; Fisher Scientific). After 5 minutes the membrane was removed from the solution, excess buffer blotted off with filter paper, and the membrane was placed in a gravity convection oven at 45° C. to dry. After drying and re-equilibration at room temperature, the membrane's mass was 1.42 g (i.e., 13% mass loss). Other membranes were soaked for 20 or 60 minutes in buffer before drying. After drying, the membranes were tested as above. The hydration ratio, acid load, and solubility (after 4 days in PBS) for each of those membranes was determined, and the results are shown in Table 8.

TABLE 8

Effect of Phosphate Buffer Conditioning on CMC/PEO Membranes

| Membrane Composition 80% CMC/ 20% PEO | Treatment | Hydration Ratio (%) | PBS pH (3 d) | Mass Loss After PO$_4$ (%) | Mass Loss After PBS (3 d) (%) | Total Mass Loss (%) |
|---|---|---|---|---|---|---|
| PEO (300 kd) pH 2.03 | Control | 258 | 4.33 | — | 29 | 29 |
|  | 5 min | 296 | 592 | 20 | 10 | 30 |
| PEO (5000 kd) pH 3.1 | Control | 553 | 4.24 | — | 36 | 36 |
|  | 5 min | 572 | 6.58 | 13 | 18 | 31 |
|  | 20 min | 685 | 7.17 | 16 | 19 | 35 |
|  | 60 min | 833 | 7.30 | 20 | 17 | 37 |

Table 8 shows that like ammonia conditioning, phosphate buffer conditioning neutralized the acid load delivered to the PBS solution. Moreover, increasing the duration of exposure to phosphate buffer resulted in progressive neutralization of the acid in the membranes. The pH increased from approximately 4.3 to 7.30 after 1 hour incubation. These membranes remain intact in PBS for at least 3 days. In contrast, membranes made at an original pH of 7.0 and above hydrated rapidly as and completely dissociated and lost integrity within several hours. Thus, conditioning acidic membranes with alkali or neutral phosphate buffer can decrease membrane solubility (increase residence time in vivo) while maintaining a highly biocompatible pH. Further, it is anticipated that soaking acidic membranes in other neutral or alkaline buffer solutions (e.g., a pH 9.0 boric acid-KCl, NaOH, 0.1 M; Fischer Scientific) will also be effective in reducing the acidity of an originally membrane.

Example 9

Conditioning Membranes Using PBS

To determine whether an isotonic, phosphate buffered saline solution can reduce the acid load delivered by a membrane, we repeated the above experiment as in Example 8, but using PBS as the buffer (10 mM, pH 7.4, 3 washes, 20 min each). A piece of dry membrane (wt, 0.340 g; composition: 80% CMC (7HF PH)/20% PEO (300 kd); pH of 3.1) was placed in a petri dish containing 50 ml of a phosphate buffered saline (PBS) solution (10 mM, pH 7.40, Sigma Chemical Company, St. Louis, Mo.) and allowed soak for 20 min. The soaking procedure was repeated another 2 times by decanting the solution from the membrane and adding fresh PBS. Next, the membrane was removed from the PBS solution, blotted and dried as above. After drying and re-equilibrating at room temperature, the membrane's mass was 0.274 g. (a 19.4% mass loss). After drying, the hydration ratio, acid load, and solubility were determined as above. Results are shown in Table 9.

TABLE 9

Effect of Phosphate Buffered Saline Conditioning on CMC/PEO Membranes

| Membrane pH 80% CMC/ 20% PEO (300 kd) | Treatment | Hydration Ratio (%) | PBS pH (3 d) | Mass Loss After PBS Conditioning (%) | Mass Loss After PBS (3 d) (%) | Total Mass Loss (%) |
|---|---|---|---|---|---|---|
| 3.72 | PBS | 3230 | 7.0 | 20 | 53 | 73 |
| 3.14 | PBS | 1295 | 6.02 | 19 | 37 | 56 |
| 2.85 | Control | 362 | 4.28 | — | 32 | 32 |
| 2.35 | PBS | 417 | 5.26 | 24 | 9 | 33 |
| 1.84 | PBS | 267 | 5.14 | 23 | 2 | 25 |

As with phosphate buffer, conditioning acidic membranes with PBS raises the membrane pH without completely disrupting the strong association between polymers that originally existed at the lower pH. Thus, an original membrane of pH 3.14, when conditioned using the PBS buffer method and subsequently placed in PBS, generated a pH of 6.02. A non-conditioned membrane which generates the same pH in PBS would originally have a pH in the range of 3–4. Additionally, except for pHs below 2, the conditioned membranes hydrate to a higher degree than un-conditioned membranes. Thus, the conditioned membranes retain some properties of the original, acidic membranes, yet are more biocompatible due to the decreased acid load delivered in solution.

Example 10

Multilayered CMC/PEO Membranes

To provide membranes with more varied properties, membranes were made by sandwiching an acidified membrane between two layers of a neutral membrane, the latter of which may or may not have the same CMC/PEO ratio as the acidified membrane. A sheet of partially dried neutral membrane was first placed on a dry flat surface used as the drying surface for the laminated membrane. A sheet of partially dried acidified membrane of slightly smaller dimensions was carefully placed on the neutral membrane. Next, another sheet of partially dried membrane was carefully placed over the acidified membrane such that the edges of the two neutral membranes were aligned and that none of the acidified membrane extended beyond the edges of the two neutral membranes. When all the three sheets were properly aligned, deionized water was slowly introduced into the petri dish, with care being taken not to misalign the sheets relative to one another. When all sheets were wetted, a non-absorbable porous thin membrane such as a nylon filter medium was carefully placed over the wetted laminate and only slightly pressed onto it. This assembly was then left undisturbed until it is dry, at which point the porous membrane was carefully removed followed by removal of the laminated membrane from the flat surface.

An alternative, double-layered membrane was made in a similar fashion. The bi-layered membrane exhibits different properties on each side. The low pH side, which is more poorly bioadhesive, permits that side to slide more easily over a tissue than the side with higher pH. The side with higher pH would adhere more strongly to the tissue in contact with it and conform to the crevices in the tissue better keeping it in place. Such membranes are valuable in situations where a mobile tissue normally can move freely with respect to a more fixed tissue.

Another bi-layered membrane was made by placing a partially dried membrane (ratio of CMC: PEO=95:5, pH 3.0, cast from 15 gm of a 2% polymer solution) in a petri dish and then pouring a CMC/PEO (ratio of CMC:PEO=95:5, pH 5.5, cast from 10 gm of a 2% polymer solution) mixture on top of the partially dried membrane. The mixture and partially dried membrane were then dried together to form the final, bi-layered membrane. In a similar way, bilayered membranes of varying PEO compositions were made, e.g., membranes in which the two layers have different PEO contents. The higher the PEO content of the layer, the more slippery the surface of that layer becomes. The other layer, with lower PEO content, adheres more strongly to the tissue.

An example is abdominal surgery, where the intestinal membranes move freely with respect to each other and to the surrounding abdominal peritoneum. Additional examples involve thoracic surgery, where the lungs must be able to move with respect to the surrounding peritoneum. Placing the high pH side of a membrane against the parietal peritoneum will keep it in place but will permit the visceral peritoneum attached to the lungs to move freely. Similarly, in cardiac surgery, placing the high pH side of a bilayered membrane onto the pericardium will keep the membrane in place and permit the low pH side to slide more freely over cardiac tissues, for example, the myocardium. Similarly, in orthopedic surgery, placing the high pH side of a membrane against a fixed tissue, such as bone or periosteum, will cause it to adhere more firmly to those locations and permit a less fixed tissue, such as a ligament, tendon, or muscle, to move more freely.

Example 11

Effect of Concentration of CMC/PEO on Stability of Casting Solutions

To determine the effects of the CMC and PEO concentrations on the stability of casting solutions, we added 16 g of CMC d.s.=1.2. and 4 g PEO (300 kd) to 50 ml isopropanol to make a slurry, which was then added to 450 ml water. This resulted in a relatively homogeneous but more viscous casting solution than that of Examples 1–9. A series of membranes were made by acidifying portions of the casting solution to progressively lower pHs. 11 g portions of the casting solution were poured into 10 cm petri dishes and dried.

Membranes were homogeneous above pH of about 3.3, whereas the association complexes precipitated from the casting solution at lower pH. At lower membrane pH, the resulting membranes had areas of inhomogeneity and holes, and had rough surfaces.

Membranes can be made from solutions of CMC as high as 10% by weight and of PEO as high as 20% by weight.

Example 12

Antithrombogenic Effect of CMC/PEO Membranes I

Samples of CMC (7 HF PH) and CMC/PEO (5000 kd) membranes were made with CMC/PEO ratios of 80%/20%, 65%/35%, and 50%/50% at a pH of from 2.7 to 2.9. An observation chamber for adherent platelets was assembled consisting of a polymer-coated glass slide, two polyethylene spacers, and a glass coverslip. Human blood, obtained from healthy adult volunteers after informed consent, was collected in heparin-containing evacuated containers (Vacutainers™, Becton-Dickinson, Rutherford, N.J.). Heparinized blood was centrifuged at 100 g for 10 min to obtain platelet-rich plasma (RP).

Two hundred $\mu$l of PRP was instilled into the platelet observation chamber. Platelets in PRP were allowed to adhere and activate on the polymer surfaces for 1 hr at room temperature. Non-adherent platelets and plasma proteins were removed by washing the chamber with PBS. Adherent platelets were fixed with 2.0% (w/v) glutaraldehyde solution in PBS for 1 hour After washing with PBS, the platelets were stained with 0.1% (w/v) Coomassie Brilliant Blue (Bio-Rad, Hercules, Calif.) dye solution for 1.5 hours. Stained platelets were observed using a Nikon Labophot™ light microscope at 40× magnification (Melville N.Y.). The image of adherent platelets was transferred to a Sony Trinitron™ video display using a Mamamatsu CCD™ camera (Hamamatsu-City, Japan). The Hamamatsu Argus-10™ image processor was used to calculate the number of platelets per 25,000 $\mu m^2$ surface area in every field of observation. The extent of platelet activation was determined qualitatively from the spreading behavior of adherent platelets. Images of activated platelets were obtained from the Sony Trinitron™ video display screen using a Polaroid ScreenShooter™ camera (Cambridge, Mass.).

The number of adherent platelets and the extent of platelet activation are considered early indicators of the thrombogenicity of blood-contacting biomaterials. Platelet activation was measured qualitatively by the extent of platelet spreading on the polymer surfaces. The extent of platelet spreading was judged from 1 (least reactive) to 5 (most reactive) as described in Table 10, which is based on the criteria of Lin et al., Polyethylene surface sulfonation. Surface characterization and platelet adhesion studies. *J. Coll. Interface Sci.* 164: 99–106 (1994), incorporated herein fully by reference.

TABLE 10

Evaluation of Platelet Activation: Surface-Induced Spreading

| Platelet Activation Stage | Approximate Spread Area ($\mu m^2$) | Remarks |
|---|---|---|
| 1 | 10–15 | Contact-adherence. Platelets not active. |
| 2 | 15–25 | Partially active. Initiation of pseudopods. |
| 3 | 25–35 | Partially activated. Pseudopod extension and initiation of release of granular contents. |
| 4 | 35–45 | Partially activated. Significant pseudopod formation and extension. Complete release of granular contents. |
| 5 | >45 | Fully activated. Retraction of pseudopods leading to the flat or "pancake" shape. |

TABLE 11

Platelet Adherence And Activation By CMC/PEO Membranes

| Membrane Composition | Number of Adherent Platelets (per 25,000 $\mu m^2$)[a] | Extent of Activation |
|---|---|---|
| 100% CMC | 95.8 ± 15.3 | 2.96 ± 0.37 |
| 80% CMC/20% PEO | 48.1 ± 10.9 | 3.25 ± 0.35 |
| 65% CMC/35% PEO | 17.8 ± 4.25 | 1.57 ± 0.39 |
| 50% CmC/50% PEO | 5.25 ± 2.67 | 1.00 ± 0.00 |

[a]: mean ± standard deviation (n = 24).

Table 11 shows that significant number of platelets had adhered and activated on membranes made of 100% CMC. On the average, more than 95 activated platelets were present per 25,000 μm². The number of adherent platelets and the extent of activation decreased with increasing PEO content in the membranes. The CMC/PEO 500/o/50% membranes had the least number of platelets. On the average, only 5.0 contact-adherent platelets were present on these membranes.

The results of this study indicate that CMC/PEO membranes, especially the 50%/50% CMC/PEO membrane, is highly anti-thrombogenic, based on the reduction in the number of adherent platelets and the extent of platelet activation on these surfaces. Thus, increasing the amount of PEO in membranes increases their antithrombogenic properties.

To determine whether CMC and PEO adversely affect blood clotting in vivo, we performed a series of studies in which we injected rabbits with CMC/PEO mixtures, and measured prothrombin time.

Four rabbits (2.4 to 2.8 kg) were anesthetized using ketamine (40 mg/kg) and xylazine (8 mg/kg), and 0.20 ml of clinical grade 2% CMC, 0.05% PEO, 50% $H_2O$ and 47.9% balanced salt solution (Lot #SD011089) was injected into the lower spinal area using a 27-gauge, ½ inch needle. A fifth, uninjected rabbit (2.8 kg) served as the control. Blood samples (approximately 1.6 ml) were taken at 0 (before injection), 2, 6, 24, 48, and 96 hr post dose. To 1.6 ml of the collected blood, 0.2 ml of 3.8% sodium citrate solution was added. After mixing plasma was prepared by centrifuging the sample at 2000 rpm for 3 to 5 minutes in a clinical centrifuge. Plasma was pipetted into a separate labeled tube and kept on ice. The sample was frozen and sent to California Veterinary Diagnostics, Inc., West Sacramento, Calif. for prothrombin-time determination, which was conducted in compliance with FDA's Good Laboratory Practice Regulations.

Table 12 shows the prothrombin times for each sample of rabbit plasma at various sampling times. Rabbit blood coagulates more quickly than human blood (Didisheim et al., *J. Lab. Clin. Med.* 53, 866–1959); thus, several of the samples collected from these rabbits coagulated before analysis. However, the samples assayed showed no effect of the CMC/PEO mixture on the prothrombin time except for rabbit No. 3, which showed a transient increase but recovered by day 4.

TABLE 12

Prothrombin Time (Seconds) of Rabbits Injected with CMC/PEO

| | Rabbit Number | | | | |
|---|---|---|---|---|---|
| Time (hr) | 1 | 2 | 3 | 4 | 5* |
| 0 | 7.2 | 7.2 | 7.1 | 8.4 | 7.1 |
| 2 | — | 7.1 | 7.1 | 7.1 | 7.1 |
| 6 | 7.3 | 7.1 | 7.1 | 7.8 | 7.1 |
| 24 | 7.2 | 7.1 | 10.6 | 7.1 | 8.0 |
| 48 | 7.3 | — | 10.3 | — | — |
| 96 | 6.2 | 6.5 | 6.5 | 6.0 | 6.0 |

*Control rabbit not injected with CMC/PEO.
— indicates that assay was not performed because the sample had coagulated.

Example 13

Determination of Bioadhesiveness of CMC/PEO Membranes

Bioadhesiveness of membranes was determined generally using a peel test described below. Several membranes composed of CMC (7HF PH) and PEO (molecular weight 5000 kd) and varying in acidity were tested for their relative bioadhesiveness using an in vitro test. Fresh, center-cut pork chops purchased from a local store were used as adherends to the membranes. Six thinly cut pork chops were placed in a polystyrene bioassay dish (243×243×18 mm) and some water placed in the dish to keep a relatively moist environment. Care was taken to blot off any excess water from the exposed side of the pork chop. Six membranes were cut in a rectangular shape to a mass of 120–130 mg and subsequently placed on six individual pieces of meat with their smooth sides down. The smooth side of the membrane is that side which was attached to the polystyrene surface during the drying process. The other side of the membrane which was exposed to air generally yields a slightly rougher surface. A top cover of polystyrene was placed over the dish and the membranes were allowed to hydrate and adhere to the meat at room temperature for 3 hours. In a similar manner, other bioassay dishes were used to test other membranes.

After the 3 hour incubation period, the membranes and the meat were carefully examined in a qualitative way for clarity (color, transparency), structural character of the membrane, form of the membrane (folding on the meat), blanching, rippling as a result of strong bioadhesion. The adhesion force in gm. was measured quantitatively in a peel test by first attaching a clip to the edge of the membrane, subsequently attaching the clip to a spring scale (0–10 gm or 0–250 gm range) and slowly pulling the membrane off the meat by vertically raising the spring scale. The force in gm. needed to pull the membrane completely free of the meat, or in some cases, to cause a rip in the membrane was recorded.

TABLE 13

Summary: Comparative Adhesion Strength of CMC/PEO Membranes

| | % PEO (5000 kd) in Membrane | | | | | |
|---|---|---|---|---|---|---|
| Membrane pH | 35% | 20% | 10% | 5% | 2.5% | 0 |
| 2.00 | — | 2 | — | — | — | 100 |
| 2.80 | 7 | 7.5[a] | — | — | — | 0 |
| 3.00 | 9 | 7.5[a] | 7[b] | 120[b] | 50[b] | 9 |
| 3.10 | — | 83[b] | 6[b] | — | — | — |
| 3.30 | — | — | — | >150[b] | 67[b] | 11[b] |
| 4.00 | — | — | 8[c] | 10[c] | 7[c] | 3 |

[a]: mean value: n = 2 ea
[b]: mean value: n = 3 ea
[c]: mean value: n = 4 ea

The results shown in Table 13 show that the adhesion force between CMC/PEO membranes is related to the membrane pH. The pH showing the greatest adhesive force for a given PEO percentage was approximately 3.30, but either increasing or decreasing the pH from this level decreased adhesion force. Further, the adhesion force was related to the % PEO in the membrane. The membranes with the highest PEO percentage exhibited the least adhesion. Increasing the PEO percentage increased adhesion until 5% PEO is reached, but further increases in PEO concentration decreased adhesive force.

Example 14

In Vivo Clearance of CMC and PEO

To determine the in vivo clearance of CMC and PEO, we performed a series of experiments in which we injected rats with radio-labeled CMC and PEO (2% CMC, 0.05% PEO, 50% H₂O and 47.9% balanced salt solution). The studies were conducted under Good Laboratory Practices.

Formulations containing [$^{14}$C]carboxymethylcellulose (CMC) and [$^{14}$C]polyethylene oxide (PEO) were injected into the lower spinal area of four groups of six rats (3 male, 3 female); two groups were sacrificed after 3 days and the remaining two groups after 7 days. Urine and feces were collected daily from these rats to study the excretion pattern of the radioactivity. In addition, representative internal organs were assayed for the residual levels of radioactivity in these rats. Two separate sets of six rats were similarly injected, and blood samples were assayed for radioactivity at 0-time (pre-injection) and 8, 24, 48, 72, 96, and 168 hours after injection.

Both compounds were excreted primarily in the urine. Most of the excretion in urine occurred during the first 24 hours. In the 7-day study, the half-times for excretion of the $^{14}$C-CMC in the urine and feces were approximately 0.2 day (5 h) initially followed by a longer excretion half-time of approximately 1.6 days. The corresponding values for $^{14}$C-PEO were 0.2 day (5 h) and 1.7 days, respectively. Of the organs assayed, the liver and kidney contained the highest levels of radioactivity. The percentage of the injected dose in the liver was comparable for $^{14}$C-CMC and $^{14}$C-PEO but that in the kidney was at least 6 times higher after injection of $^{14}$C-PEO than after injection of $^{14}$C-CMC.

The radioactivity level in the blood after $^{14}$C-CMC administration declined with half-time of approximately 1 day, whereas the blood half-time for $^{14}$C-PEO was approximately 4 days. Higher percentages of the administered dose remained in the carcass plus injection site for $^{14}$C-CMC than for $^{14}$C-PEO. The mean overall recovery of the administered dose was 80+% for both compounds. No adverse reactions to the injected $^{14}$C-CMC or $^{14}$C-PEO were observed.

Example 15

Viscosity of CMC/PEO Solutions as a Function of pH

Figure 8A:
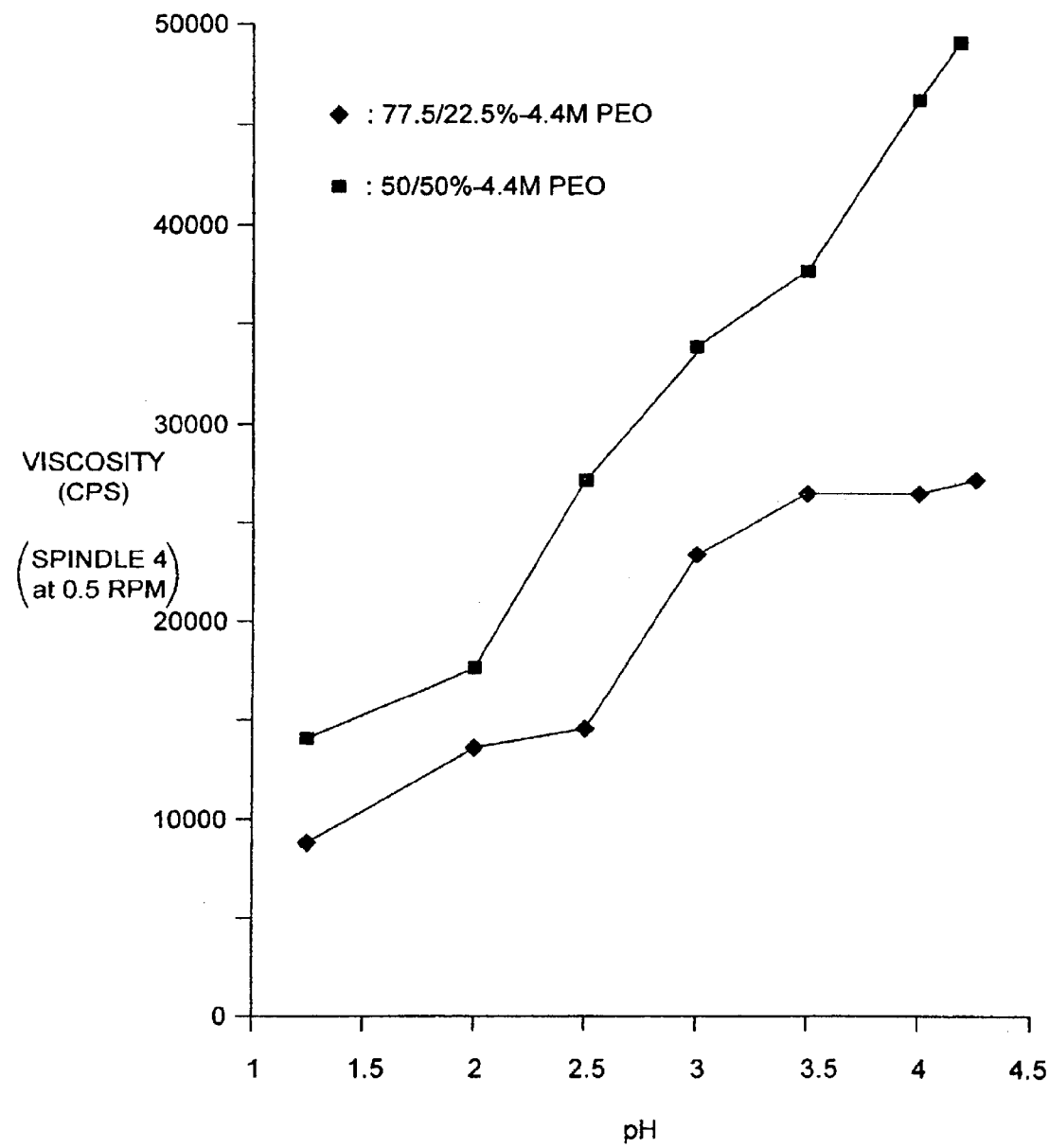
FIGS. 8a–8b show the effect of varying pH of CMC/PEO solutions of differing compositions on the viscosity of the solutions.
Figure 8B:
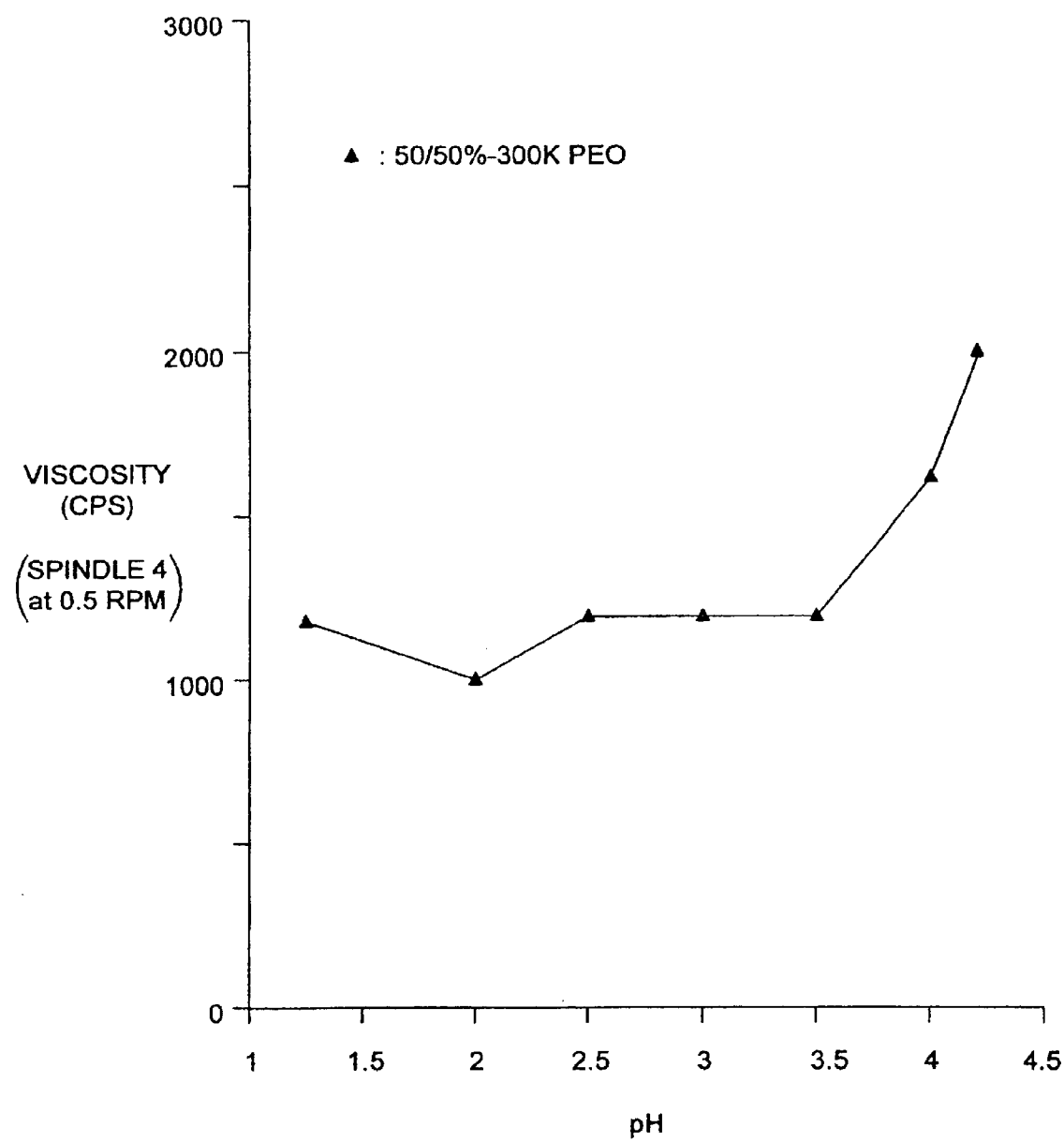

To determine the effect of varying the solution pH on the viscosity of CMC/PEO solutions, we determined the apparent viscosity samples of a solution containing 1.33% solids, and having a ratio of CMC:PEO of 77.5:22.5 with the molecular weight of PEO being 4.4 Md; ♦), a solution having a CMC:PEO ratio of 50:50 with a molecular weight of PEO being 4.4 Md; ■), and a solution having a CMC::PEO ratio of 50:50 and a molecular weight of/50% PEO being 300 kd; ▲), see FIGS. 8a–8b. Viscosity data is presented in centipoise; cps; as measured using spindle No. 4 at 0.5 rpm.

FIG. 8a shows that at each pH, the viscosities of solutions having a ratio of CMC:PEO of 77.5:22.5 were higher than those of solutions having a CMC:PEO ratio of 50:50. Moreover, for both solutions, increasing the pH increased the viscosity of the solutions, with the change in viscosity being more pronounced at pH values above about 2. FIG. 8b shows the results of a similar study using a solution having a ratio of CMC:PEO of 50:50, with a molecular weight of the PEO being 300 kd. For this solution, raising the pH above about 3.0 caused a large increase in viscosity.

Example 16

Measurements of Turbidity of CMC/PEO Solutions

To determine whether the CMC and PEO associated into large aggregates that cause fight scattering, we measured the appearance of particles of CMC/PEO in solution using a nephelometry apparatus. We used two types of apparatus: a Model 21 nephelometer (side scatter design, Monitek, Inc.) and a Model 251 turbidimeter (forward scatter design, Monitek, Inc.). Light absorbance was measured using a Monitek light absorbance instrument using a tungsten lamp, which provides visible and near infrared light emission.

Figure 9A:
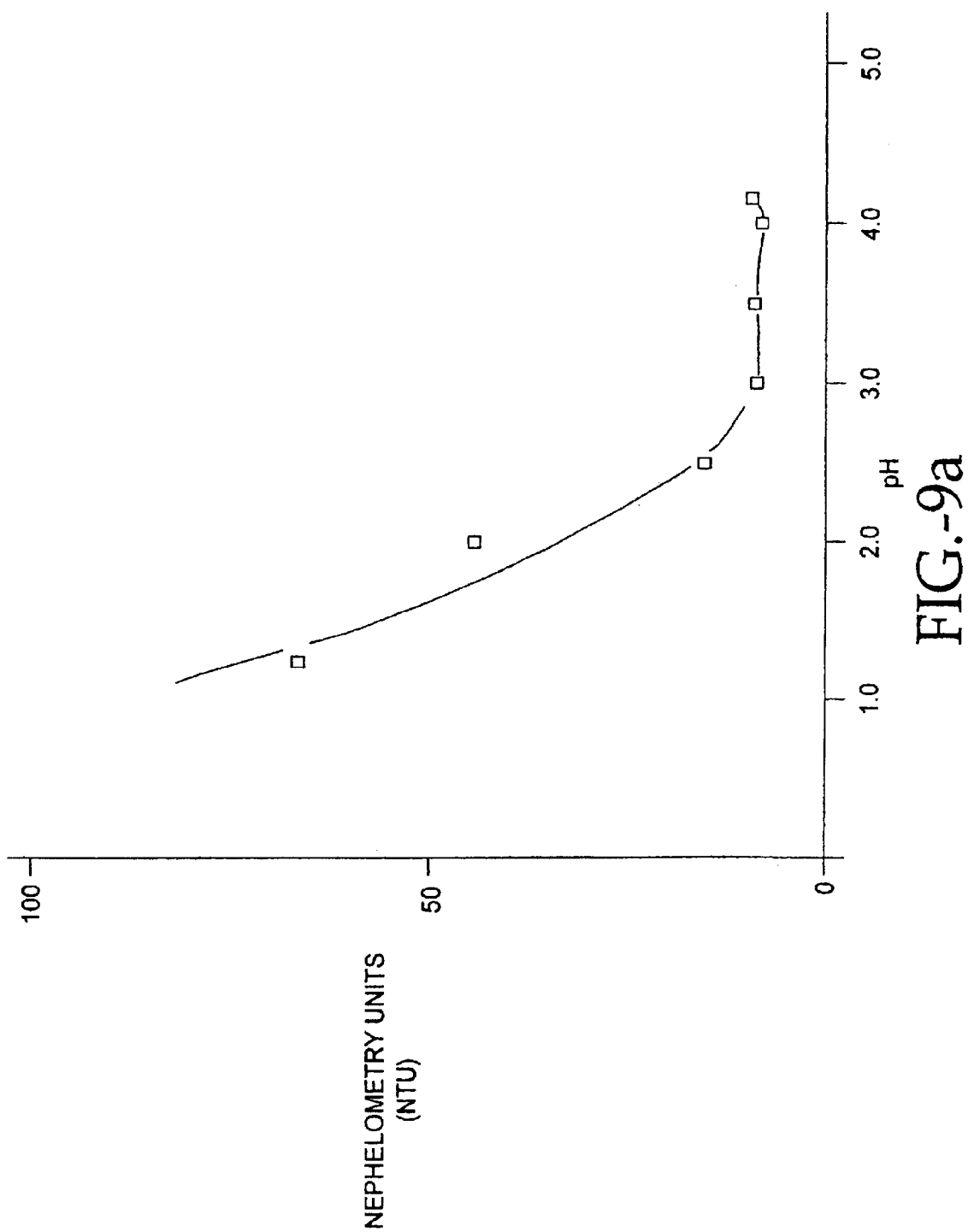
FIGS. 9a and 9b show the effect of solution pH on the turbidity of a solution containing 1.33% total solids and a CMC:PEO ratio of 50:50 with the molecular weight of the PEO of either 4.4 Md (FIG. 9a) and 500 kd (FIG. 9b) as measured using nephelometry apparatus.
Figure 9B:
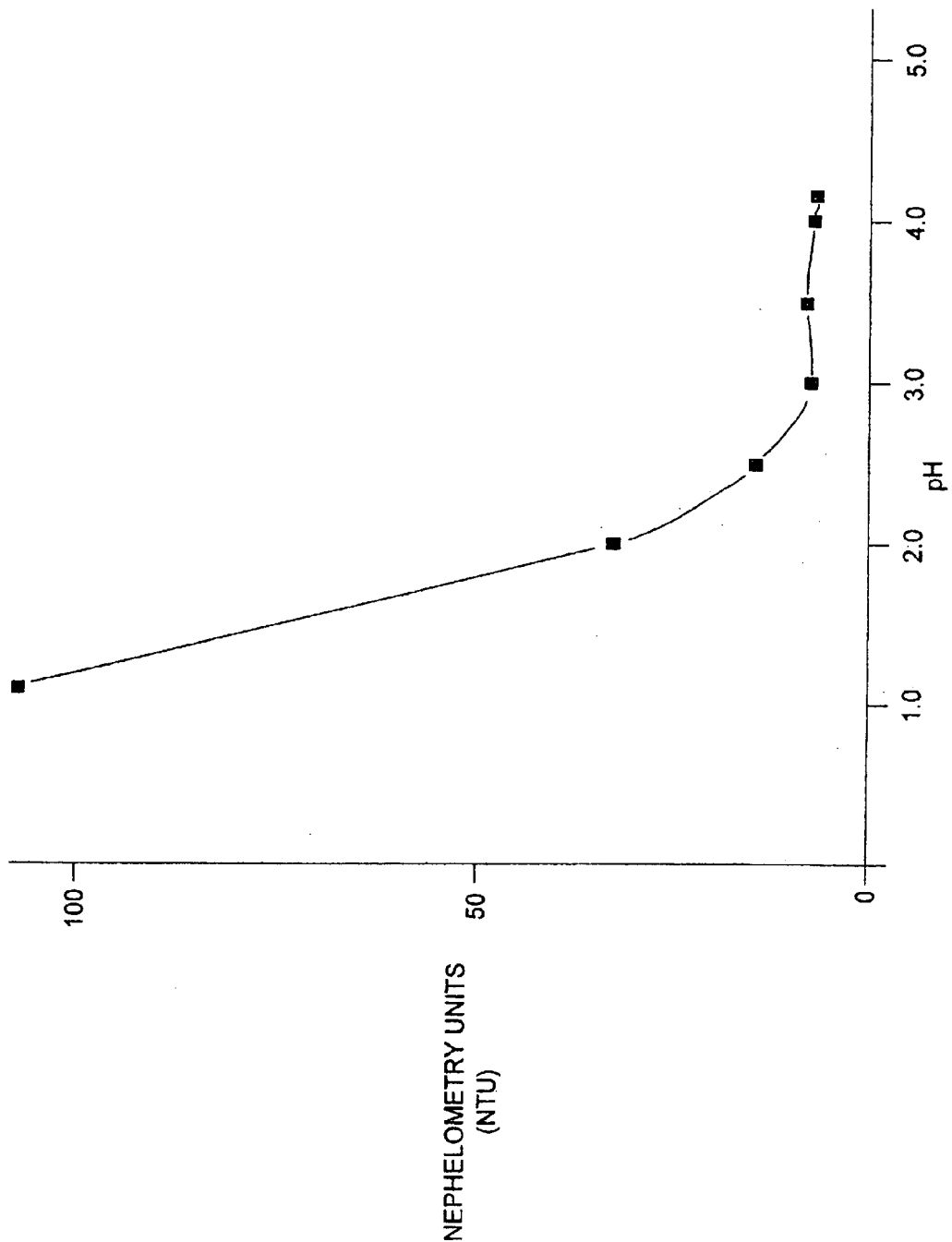
Figure 10:
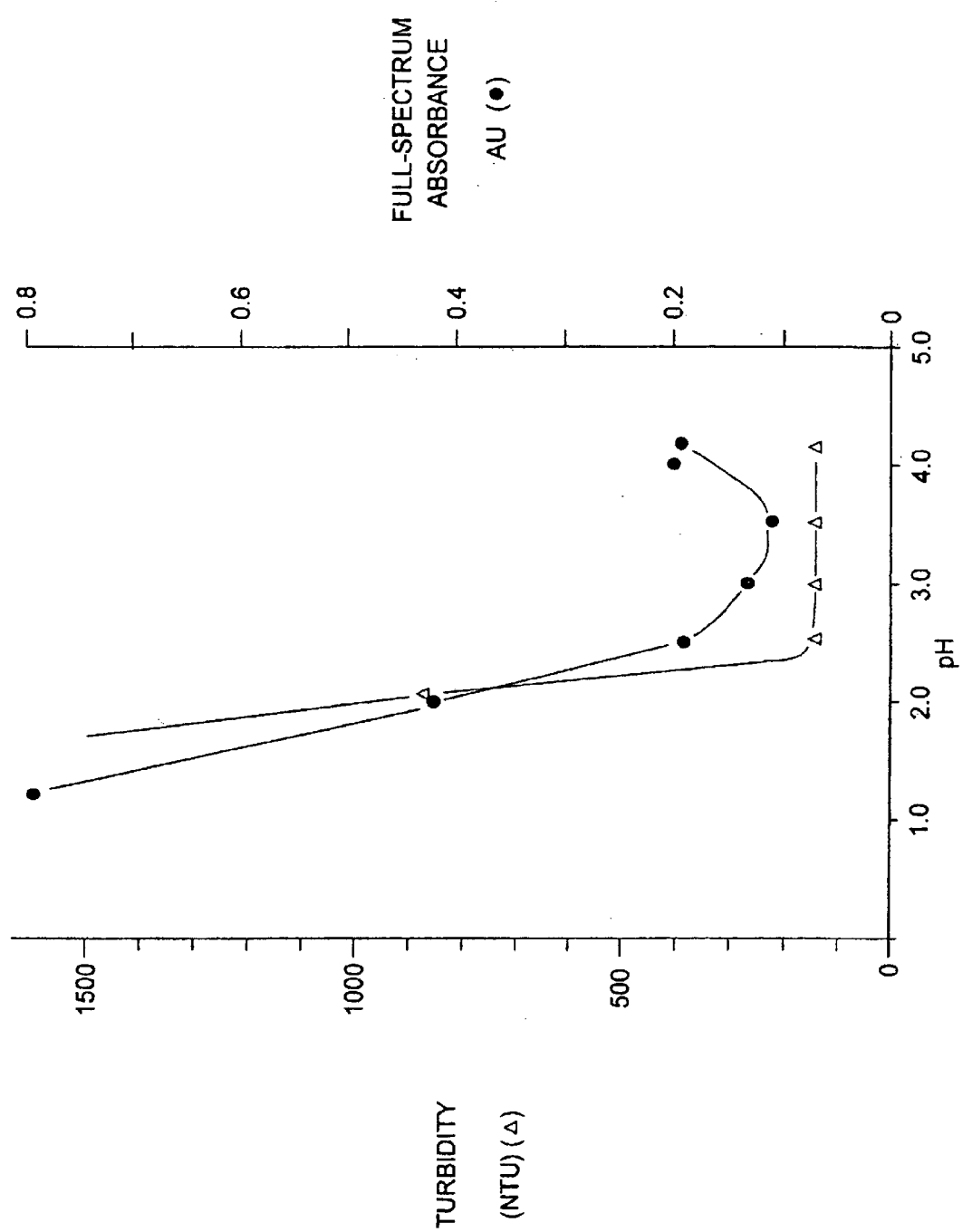
FIG. 10 shows the effect of solution pH on full spectrum absorbance (●) and forward scan turbidity (Δ) of the solutions described in FIG. 9, measured using nephelometry apparatus.

After making the mixtures for study, the mixtures were maintained in a homogeneous state if needed by stirring with a low speed (60–120 rpm) laboratory stirring device. Results of the studies are shown in FIGS. 9 and 10. FIG. 9a shows the results of an experiment to determine the effect of solution pH on side scattering, as measured in nephelometry units (NTU), of a solution containing 1.33% total solids and a ratio of CMC:PEO of 50:50, wherein the molecular weight of the PEO was 4.4 Md. At a pH above about 3, the scattering was minimal, with every data point being below 10 NTU. As the pH was decreased to 2.5, side scattering increased slightly, and when the pH was further reduced to 2 and below, the side scattering increased substantially. FIG. 9b is of a similar experiment as shown in FIG. 9a, except that the solution had a CMC:PEO ratio of 50:50 and the molecular weight of the PEO was 300 kd. As with the higher molecular weight PEO, in the pH range above about 2.5, there was little side scattering, but in the pH range below about 2.5, side scattering increased substantially.

FIG. 10 shows the results of similar studies of a solution having 1.33% total solids content and a ratio of CMC:PEO of 50:50 and wherein the molecular weight of the PEO was 4.4 Md, in which the full spectrum absorbance, expressed in absorption units (AU) (right-hand scale; ●) and forward scan turbidity, expressed as NTU (left-hand scale; Δ) were measured. As with the nephelometry data presented in FIGS. 9a and 9b, in the pH range above about 2.5, there is little turbidity or absorbance, whereas in the pH range below about 2.5, there are striking increases in turbidity and absorbance as pH is reduced.

These studies indicate that above pH of about 2.5, CMC and PEO remain in suspension. However, when the pH is reduced to below about 2.5, precipitation begins to occur, and the CMC and PEO form aggregates which scatter light sufficiently to be detected (see FIGS. 9 and 10).

Example 17

Hydration of CMC/PEO Membranes as a Function of pH

Figure 11A:
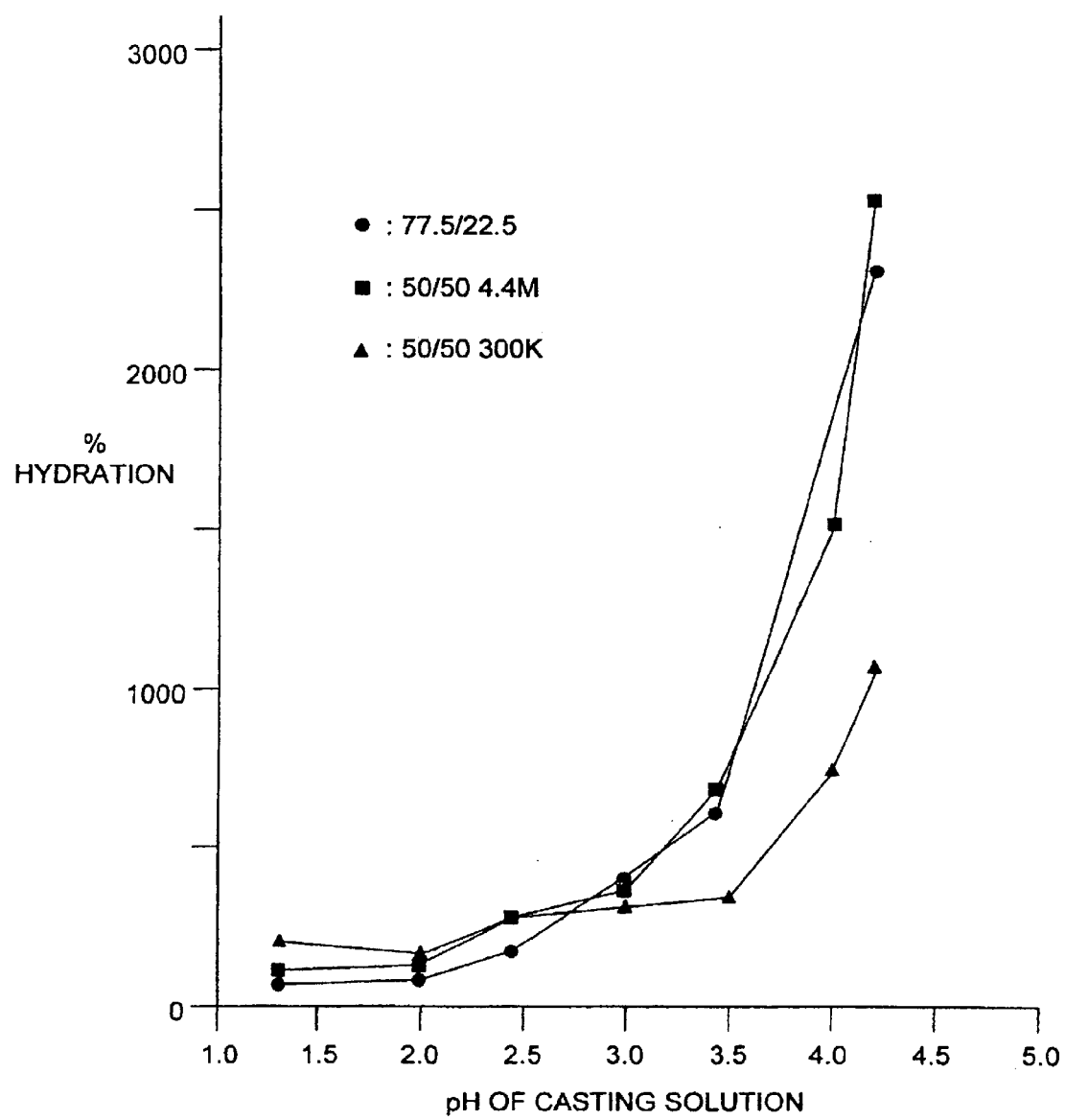
FIGS. 11a–11b show the effects of pH on hydration ratio of CMC/PEO membranes: 77.5%/22.5%, 4.4 Md PEO, 50%/50%, 4.4 Md PEO, and 50%/50%, 300 kd PEO.
Figure 11B:
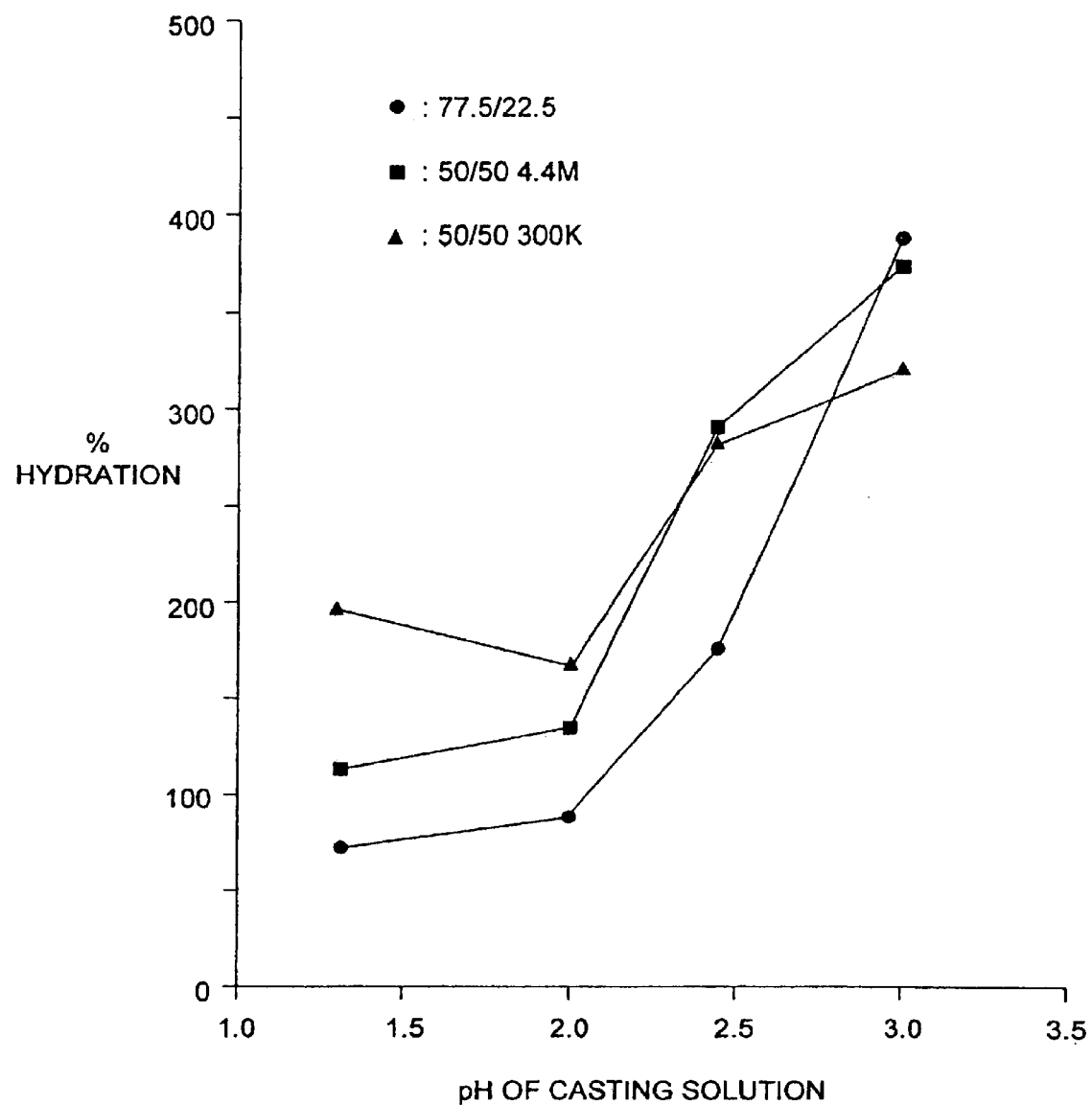

Three series of CMC/PEO membranes were manufactured and studied, and the results are shown in FIGS. 11a and 11b. One series comprised 77.5% CMC/22.5% PEO (4.4 Md; ●). Another series was made of 50% CMC/50% PEO (4.4 Md; ■), and the third was made of 50% CMC/50% PEO (300 kd; ▲). In each case, membranes were dried and then immersed in PBS for 20 hours. After 20 hours, the membranes were blotted dry, and the wet weight was determined. The hydration ratio (% hydration) is expressed as the (wet weight–dry weight)/dry weight×100%.

FIG. 11a shows the results of the experiments over the entire range of pH studied. At a pH of about 2.0 and below, there is little, if any, dependence of hydration ratio on pH. However, as the pH increases above about 2.0, there is an increase in hydration ratio for each type of membrane studied.

FIG. 11b shows the results of the same experiments, but only the pH range of 3 and below are shown. This graph emphasizes the lack of a significant effect of pH on hydration in the pH range below about 2.0. However, in the pH range of above 2 to about 3, there are substantial increases in hydration as pH is raised. Moreover, at the pH range below about 2, there is little dependence of hydration on pH; increasing pH from 1.3 to about 2 resulting in only a slight increase in hydration for the membranes containing 4.4 Md PEO. However, above a pH of about 2, the incremental effect of increasing pH is much greater than it is in the range of pH below 2. Regardless of the PEO used, or the ratio of CMC to PEO, every membrane type showed the large dependency of hydration on pH above 2.

These results are unexpected based upon the prior art, such as the Smith et al. patent, which showed hydration ratios of 16% and 18% for CMC/PEO membranes at pH of 1.25.

Example 18

Solubility of CMC/PEO Membranes

In another experiment to study the solubility of CMC/PEO membranes in 0.9% NaCl, we made membranes of 77.2% CMC/22.5% PEO (4.4 Md; +), 50% CMC/50% PEO (4.4 Md; ■) and 50% CMC/50% PEO (300 kd; ▲). Membranes were made at different pH values, and were immersed in 0.9% NaCl for a period of 5 days, after which time, the membranes were dried and weighed. The data are expressed in FIG. 12 as the percent of the original dry weight.

Figure 12:
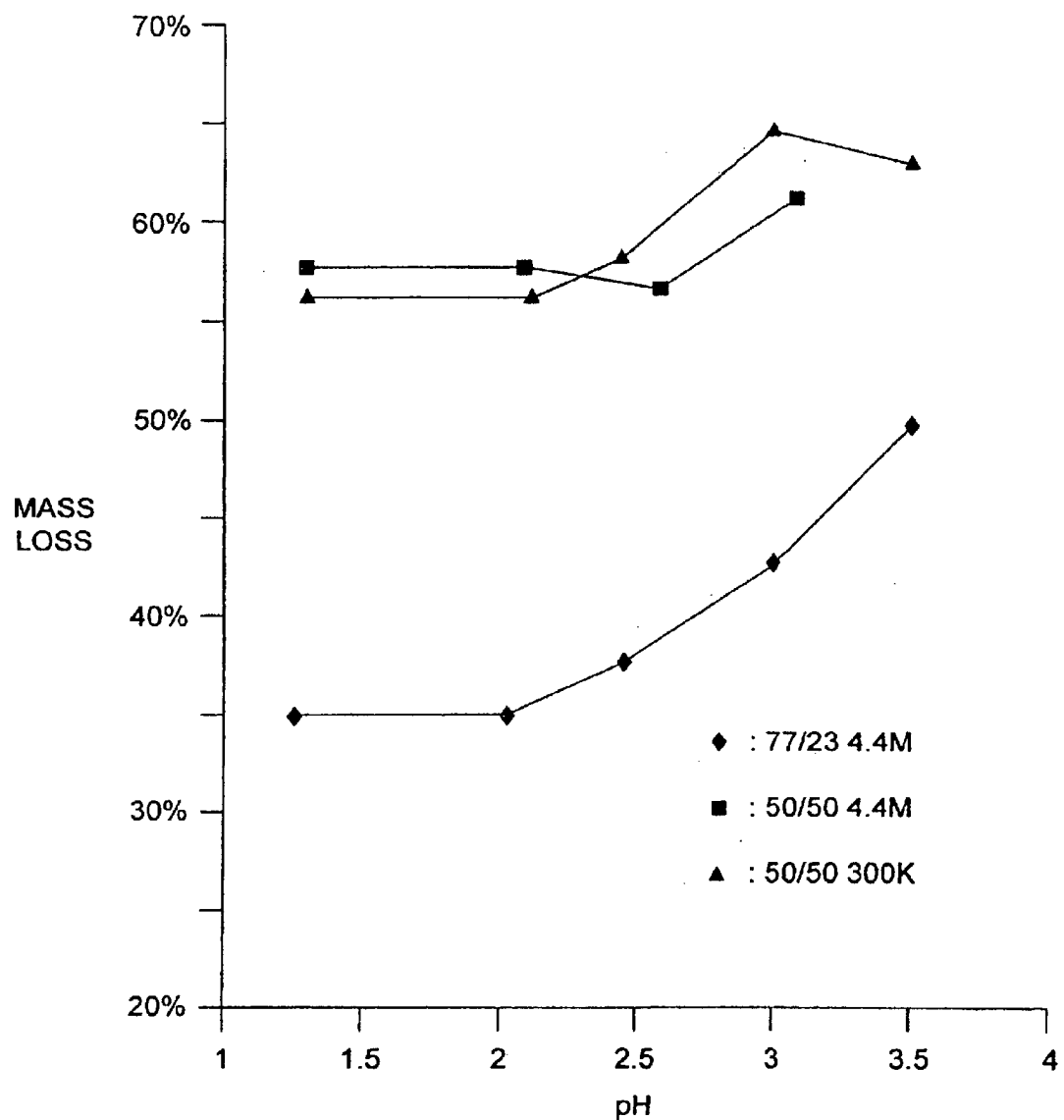
FIG. 12 shows the relationship between solution pH and solubility of CMC/PEO membranes of the compositions indicated.

FIG. 12 shows that the 77.5% CMC membrane was the least soluble, with only about 35% of the initial dry weight lost during the 5 day immersion. Moreover, in the pH range of 2 and below, there was no change in solubility with pH. However, as the pH increased to 2.5 and above, there was a progressive increase in solubility of the membranes. The membranes made with 50% CMC were more soluble (at least 55% soluble) at each pH than were the membranes made with 77.5% CMC. As with the 77.5% CMC membranes, the membranes made with 50% CMC showed no dependence of solubility on pH below about 2.5. However, above a pH of about 2.5, there was in increase in solubility as pH increased.

Example 19

Bioadhesion of CMC/PEO Membranes

To further characterize the bioadhesive properties of CMC/PEO membranes of this invention, we determined the relationship between membrane pH and bioadhesiveness using a bovine mesentery loop adhesion system. Pieces of fresh bovine mesentery were attached to an adhesive platform, and a loop of CMC/PEO membrane was used as an adherend, being held on an arm of the device. The mesentery and membrane were moistened with water, and the loop of membrane was lowered to make contact with the mesentery. The arm was raised, and the force in grams was continuously monitored. When the loop of membrane broke away from the mesentery, the force was recorded. The force required to detach the membrane from the mesentery was recorded for membranes manufactured in the pH range of about 1.25 to about 4.25.

Figure 13A:
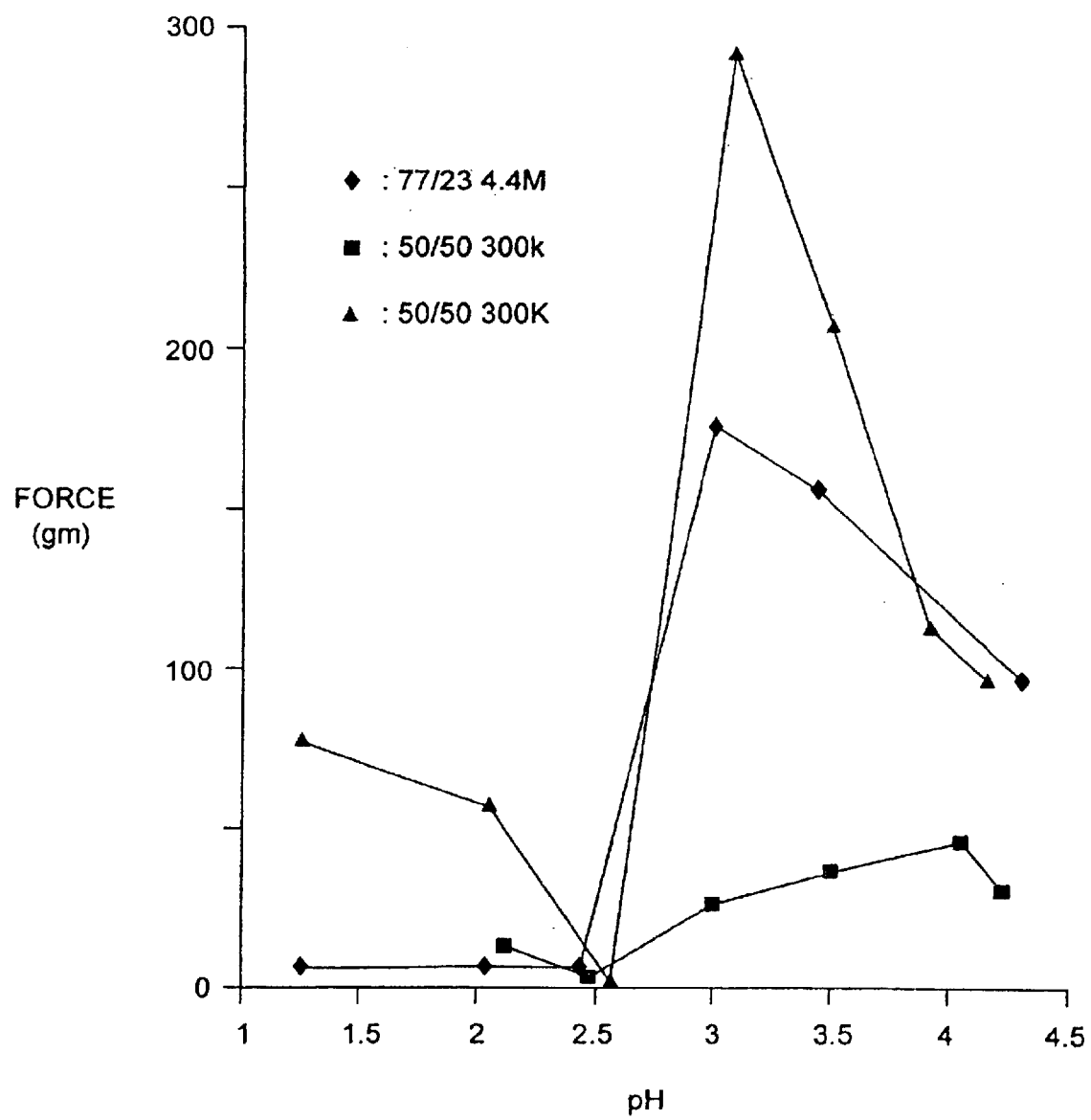
FIG. 13a shows the relationships between membrane pH and bioadhesion for 3 CMC/PEO membranes of the compositions indicated.
Figure 13B:
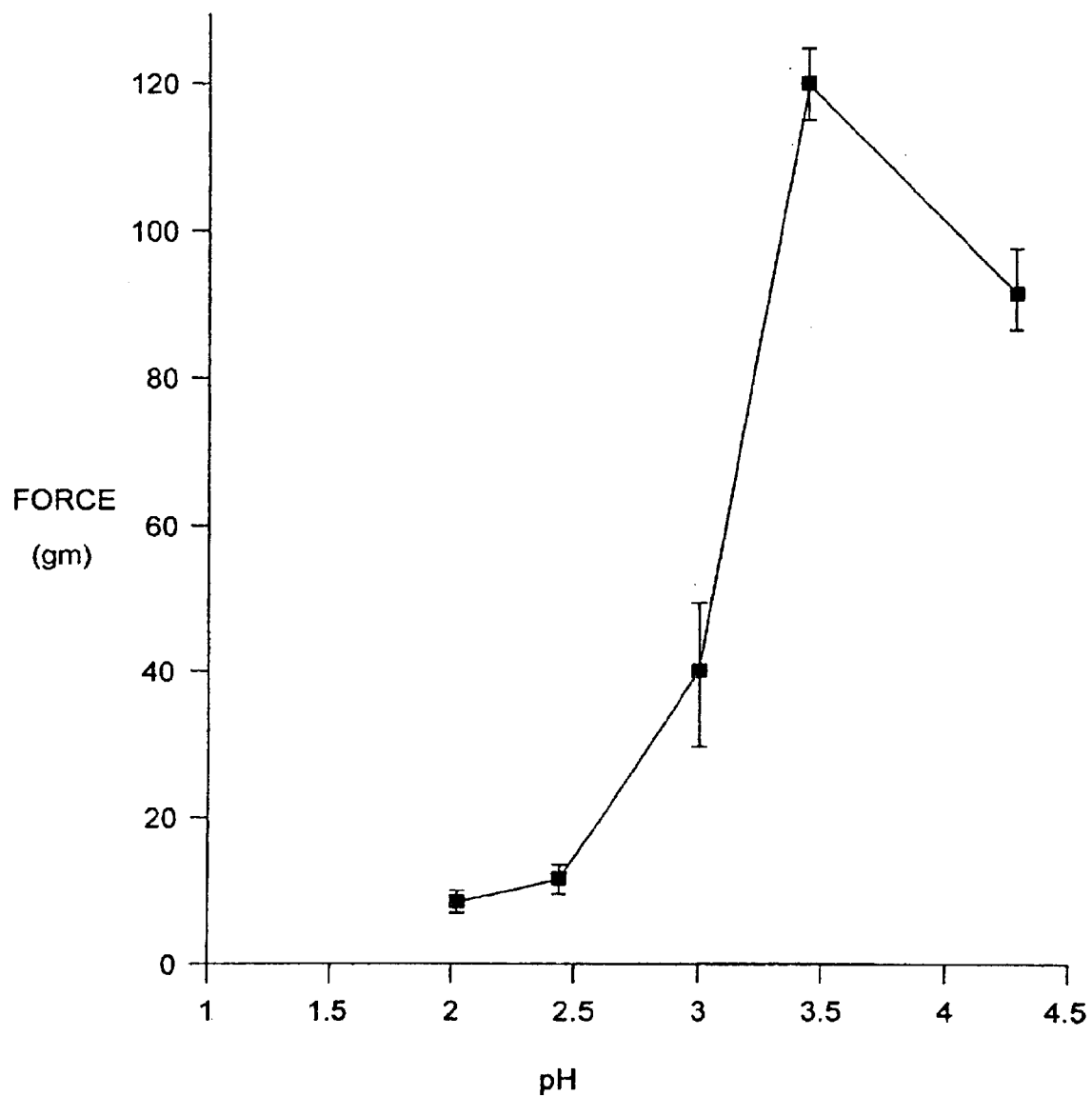
FIG. 13b shows the average data for the relationships between pH and bioadhesiveness for 77.5% CMC membranes.

FIGS. 13a and 13b show the results of the bioadhesion test using the bovine mesentery. In FIG. 13a (77.5% CMC/22.5% PEO, 4.4 Md; ♦), the membranes at pH of below 2.5 did not adhere well to the mesentery. However, as the pH was raised to above 2.5, the membrane adhered well to the mesentery, requiring a force of about 170 g to detach the membrane at a pH of 3.0. Membranes made of 50% CMC/50% PEO (300 kd; ■) similarly did not adhere to the bovine mesentery at pH of below about 2.5. However, increasing the pH increased the adherence of these membranes. In contrast, membranes of 50% CMC/50% PEO, 4.4 Md (▲) adhered at the lowest pH of 1.25, but increasing the pH to 2.5 decreased the adherence to the bovine mesentery. Unexpectedly, increasing the pH above 2.5 reversed this trend, and increased the adherence to the mesentery to a very high degree, with the force required to detach the membrane from the mesentery at a pH of 3.0 being about 280 g. Moreover, as the pH was increased further, there were decreases in adherence of two of the membrane series, but in no case did bioadhesion decrease to values below those seen at a pH of 2.5 for that membrane series.

FIG. 13b shows the summary of data obtained for studies of 77.5% CMC/22.5% PEO (4.4 Md) membranes. Data are expressed as the mean±standard error of the mean; n=6 or 7. As with the single series presented in FIG. 13a, in the pH range of 2.4 and below, the membranes did not adhere to the mesentery well. However, increasing the pH to above about 2.5 increased adherence substantially, and in a pH-dependent fashion, with a maximal force required to detach the membrane from the mesentery of about 120 gms.

These results observed at in the pH range of greater than 2.5 are completely unexpected based on the results obtained at the low pH range of 2.0 and below. CMC/PEO membranes made in the pH range similar to those of Smith et al. adhere only poorly to biological materials, and does not predict the bioadherence behavior of CMC/PEO membranes at pH ranges above about 2.5.

Example 20

Effect of CMC/PEO Films on Adhesiveness Biocompatability and Bioresorption

Introduction:

The purposes of this study were first to determine the ability of films containing various combinations of polyethylene oxide (PEO) and carboxymethyl cellulose (CMC) to adhere to various organs within the peritoneal cavity. The second purpose was to grossly assess the biocompatability of the same five films. The third purpose was to determine whether films of this invention are bioresorbable.

Methods:

Twenty, female, 2.4–2.7 kg, New Zealand White rabbits were quarantined at least 2 days prior to surgery. On the day of surgery, the rabbits were anesthetized with intramuscular ketamine/xylazine and prepared for sterile surgery. A midline laparotomy was performed and 2 cm pieces of film of the invention were placed on the sidewall, bowel and uterine horns. The only injury that was performed besides the incision line was removal of the broad ligament of the rabbit uterine horns to allow the films to be wrapped on the uterine horns. After recovery, the rabbits were returned to the vivaria. At 24, 48, 72 and 96 hours after surgery, the rabbits were reopened at the incision line for evaluation of the site of the material relative to initial placement, the condition of the material and the appearance of the tissue in contact with the material.

Films Used:

The films studied were gamma irradiated with a total dose of 2.5 megaRads ("MRad"), and comprised: 95% CMC/5% PEO, pH 5.0 (film No.: 414), a bi-layered membrane comprising layers of 60/o CMC/40% PEO, pH 2.0 and 95% CMC/5% PEO, pH 5.0 (film No.: 417), a bilayered membrane comprising layers of 60% CMC/40% PEO, pH 3.0 and 95% CMC/5% PEO, pH 5.0 (film No.: 418), 95% CMC/5% PEO, pH 4.0 (film No.: 419) and 95% CMC/5% PEO, pH 3.0 (film No.: 422). After insertion of the film, a suture comprising 3-0 Dexon-II was used to close the abdominal muscle and skin.

Results:

The majority of the materials were soaked with blood at the horn and were associated with a large blood clot at all times observed. Only in the instances that this was not the case will the observation be noted below. Overall, very little inflammation was noted in association with the placed materials. Again, only in the instances where any inflammation or tissue damage was observed will be noted. At all times, the inflammation was localized and quite transient (noted only at one time point and in one animal per time point).

The film comprising 95% CMC/5% PEO, pH 5.0 (film No.: 414) was present at the site of placement in 4 of 6 sites 24 hours after implantation. Forty-eight hours after implantation, the material was present at 5 of 6 sites and was fragmented at the bowel. After 72 hours, the material was present only at the horns (in one rabbit the material was fragmented). In one rabbit at 72 hours, slight petechial hemorrhage was observed on the bowel of one rabbit. After 96 hours, the material was present at 3 of the 6 sites. At one site, the material observed was gel-like.

The film comprising 95% CMC/5% PEO, pH 4.0 (film No.: 419) was present at 5 of 6 sites at 24 and 48 hours. At 48 hours, the material at the bowel was fragmented. In one rabbit, whitening and petechial hemorrhage was observed at the sidewall. At 72 hours, the material was present at 4 of 6 sites. The material on the bowel was fragmented. Gel-like material was present in the gutter. At 96 hours, fragmented and/or gel-like material was present at 5 of the 6 sites. In one rabbit, the material at the horn was not associated with a blood clot.

The film comprising 95% CMC/5% PEO, pH 3.0 (film No.: 422) was present at all sites at 24 hours after implantation. At 48 hours, the material was present at 3 of 5 sites. Whitening (more intense in the center than at the edges) was observed at the sidewall of one rabbit. Some petechial hemorrhage was observed on the bowel of this same rabbit. At 72 hours, the material was present at all sites. On the sidewall and the bowel, the material could not be seen visually, but a slippery gel-like coating was observed at the site of placement. At 96 hours, an intact piece was observed at the horn and on the bowel of one rabbit. On the sidewall of both rabbits and bowel of the other rabbit, small fragments and slippery gel was present at the site of placement.

The bilayered film comprising 95% CMC/5% PEO, pH 5.0 and 60% CMC/40% PEO, pH 2.0 (film No.: 417) was present at 4 of 6 sites. At this time, a small amount of irritation was observed on the bowel of one rabbit. At 48 hours, the material was observed at 3 of 6 sites (fragmented at bowel). At 72 hours, the material was presented at 3 of 6 sites and irritation was observed at the sidewall of both rabbits. At 96 hours, fragments was observed at 5 of 6 sites. At the horn, no large blood clot was observed associated with the material at the horns. Inflammation and petechial were observed on the bowel.

The bilayered film comprising 95% CMC/5% PEO, pH 5.0 and 60% CMC/40% PEO, pH 3.0 (film No.: 418) was present at all sites at 24 hours. Some inflammation was observed at the sidewall of one rabbit. At 48 hours, the material was observed at 5 of 6 sites (gel-like at 3 of these sites). At 72 hours, the material was present at 5 of 6 sites (gel-like at 4 sites). In one rabbit, petechial hemorrhage and bruising was observed at sidewall (same rabbit with inflammation at 24 hours). At 96 hours, fragments of material was present at 5 of 6 sites. In one rabbit, the material at the horn was not associated with a blood clot.

Conclusion:

These studies indicated that both monolayered and bilayered membranes of this invention adhere to the peritoneal tissues of rabbits. The studies also indicated that the films were biocompatible and were retained in the animal's bodies for periods of time, with some of the film being removed from the surgical sites by the animals' physiological processes.

Example 21

Evaluation of Films of the Invention In the Prevention of Formation of Abdominal Adhesions Introduction:

The purposes of this series of studies was to test the efficacy of films of this invention on the formation of abdominal adhesions in a rabbit model of adhesion formation between the sidewall and cecum and bowel.

Methods:

1. Animals:

Forty female New Zealand White rabbits, 2.4–2.7 kg, were purchased and quarantined for at least 2 days prior to use. The rabbits were housed on a 12:12 light:dark cycle with food and water available ad libitum.

2. Materials:

The films studied comprised bilayered films consisting of layers of 95% CMC/5% PEO, pH 5.0 and 60% CMC/40% PEO, pH 2.0 (film No.: 438), which had been gamma irradiated with a total gamma ray dose of 2.5 MRad, a bilayered film comprising layers of 95% CMC/5% PEO, pH 5.0 and 60% CMC/40% PEO, pH 3.0 (film No.: 437) and a monolayered film comprising 95% CMC/5% PEO, pH 4.0 (film No.: 436). The sutures that were used to close the peritoneum and skin were 3-0 coated Dexon II suture (Davis and Geck, Manati, PR).

3. Sidewall Model of Adhesion Formation:

Rabbits were anesthetized with a mixture of 55 mg/kg ketamine hydrochloride and 5 mg/kg Rompum intramuscularly. Following preparation for sterile surgery, a midline laparotomy was performed. The cecum and bowel were exteriorized and digital pressure were exerted to create subserosal hemorrhages over all surfaces. The damaged intestine was then lightly abraded with 4"×4", 4-ply sterile gauze until punctuate bleeding was observed. The cecum and bowel were then returned to its normal anatomic position. A 4×3 cm area of peritoneum and transversus abdominous muscle was removed on the right lateral abdominal wall. The film was placed at the site of sidewall injury. After 7–8 days, the rabbits were killed and the percentage of the area of the sidewall injury that was involved in adhesions was determined.

In addition, the tenacity of the adhesions was scored using the following system:

0=No Adhesions
1=mild, easily dissectable adhesions
2=moderate adhesions; non-dissectable, does not tear the organ
3=dense adhesions; non-dissectable, tears organ when removed.

A reduction in either the area or the tenacity of the adhesions were considered to be beneficial.

Results:

In the 10 control rabbits, 5 had adhesions varying from an area of 20% to 80% of the sidewall. The other 5 control rabbits had no adhesions. However, none of the sites having antiadhesion membranes had any evidence of adhesions.

Example 22

Evaluation of CMC/PEO Films in Preventing Reformation of Abdominal Adhesions Introduction:

The purpose of this study was to evaluate the efficacy of PEO/CMC films in reducing reformation of abdominal adhesions in rabbits after lysis of adhesions between the sidewall and cecum and bowel.

Methods:

1. Animals:

One hundred ten female New Zealand White rabbits, 2.4–2.7 kg, were be purchased from Irish Farms (Norco, Calif.) and quarantined in the USC Vivaria for at least 2 days prior to use. The rabbits were housed on a 12:12 light:dark cycle with food and water available ad libitum. The rabbits that had adhesions and no evidence of subcutaneous infection were used in the lysis portion of the study.

2. Materials:

The PEO/CMC films used in this study comprised of 95% CMC/5% PEO, pH 4.0 (film No.: 603), a bilayered film consisting of layers of 95% CMC/5% PEO, pH 5.0 and 60% CMC/40% PEO, pH 3.0 (film No.: 604) and a bilayered film consisting of layers of 95% CMC/5% PEO, pH 5.0 and 60% CMC/40% PEO, pH 2.0 (film No.: 605). The films contained FD&C Blue Dye No 2 and were sterilized by exposure to gamma irradiation (2.5 MRad total dose). In a separate experiment, we studied films (film No.: 627) comprising 77.5% CMC and 22.5% PEO, pH 4.2, also having Blue Dye No 2. Adhesion prevention in animals receiving membranes having the above compositions were was compared to control animals not receiving any anti-adhesion membrane. After implantation of the membranes, sutures 3-0 coated Dexon II suture (Davis and Geck, Manati, PR) were used to close the peritoneum and skin.

Sidewall Model of Adhesion Reformation:

Rabbits were anesthetized with a mixture of 55 mg/kg ketamine hydrochloride and 5 mg/kg Rompum intramuscularly. Following preparation for sterile surgery, a midline laparotomy will be performed. The cecum and bowel were exteriorized and digital pressure was exerted to create subserosal hemorrhages over all surfaces. The damaged intestine was then lightly abraded with 4"×4", 4-ply sterile gauze until punctuate bleeding was observed. The cecum and bowel were returned to their normal anatomic position. A 5×3 cm area of peritoneum and transversus abdominous muscle were removed on the right lateral abdominal wall. The incision was closed in two layers with 3-0 Dexon II. One week later, the animals were anesthetized as described above and underwent a second laparotomy. In the rabbits where adhesions were present, the adhesions were scored and lysed using blunt and sharp dissection. Care was taken not to injury the bowel.

3. Implantation of Antiadhesion Films:

The selected film was placed at the site of adhesiolysis. After 7 to 10 days the rabbits were killed and the percentage of the area of the sidewall injury that was involved in adhesions was determined as described in Example 21 above.

Results:

The results of this study are presented below in Tables 14–16. All of the CMC/PEO films studied were highly efficacious in the reduction of adhesion reformation. These data are summarized in Table 14 (area of adhesion reformation) and Table 15 (incidence of adhesion reformation).

TABLE 14

Effects of CMC/PEO Membranes on Adhesion Reformation

| Membrane Composition | Initial Area of Adhesions | Area of Adhesions After Reformation | % Initial Area |
|---|---|---|---|
| Control | 82.2 ± 2.8 | 67.8 ± 9.8 | 83.5 ± 11.9 |
| 95/5, 4.0 | 77.8 ± 8.5 | 5.6 ± 3.8 | 5.6 ± 3.8 |
| 95/5, 5.0: 60/40, 3.0 | 80.9 ± 7.7 | 0.9 ± 0.9 | 1.3 ± 1.3 |
| 95/5, 5.0: 60/40, 2.0 | 82.2 ± 7.2 | 1.1 ± 1.1 | 1.1 ± 1.1 |

Membrane composition is expressed as the % CMC/% PEO, pH, and bilayered membranes are expressed as the composition of the two layers. Data is expressed as the mean ± standard deviation.

TABLE 15

Effect of CMC/PEO Films on Incidence of Adhesion Reformation

| Group | # of Animals Adhesion Free | % of Animals Adhesion Free |
|---|---|---|
| Control | 0/9 | 0.0 |
| 95/5, 4.0 | 7/9 | 77.7 |
| 95/5, 5.0: 60/40, 3.0 | 10/11 | 91.0 |
| 95/5, 5.0: 60/40, 2.0 | 8/9 | 88.8 |

These experiments show that bilayered CMC/PEO films substantially prevent adhesion reformation.

TABLE 16

Effect of a CMC/PEO Film (No.: 627) on Adhesion Formation

| | Initial Area of Adhesions | Area of Adhesions After Reformation | % Initial Area |
|---|---|---|---|
| Control | 84.6 ± 5.5 | 80.0 ± 6.7 | 95.5 ± 7.3 |
| 77.5% CMC/ 22.5% PEO, pH 4.2, Dyed | 81.0 ± 6.2 | 7.0 ± 4.7 | 7.0 ± 4.7 |

Data expressed as mean ± standard deviation.

The monolayered film #627 increased the number of animals that were adhesion-free from 0 of 11 to 8 of 10. This study shows that the monolayered CMC/PEO film substantially reduces the incidence and severity of the reformation of adhesions.

Example 23

Intracutaneous Reactivity of CMC/PEO Films

Introduction:

The purpose of this test was to evaluate the potential of the test material to produce irritation following intracutaneous injections into rabbits.

Methods:

1. Animals:

As in the previous examples, New Zealand White rabbits were used for this study. The rabbit is the species required by the current version of the International Organization for Standardization. They were obtained from Grimaud Farms of California, Stockton, Calif. Three adult female animals were used, and weighed between 2.2 and 2.3 kg each. The animals were housed individually and maintained at 16–22° C. and 50±20% relative humidity. They were fed Laboratory Rabbit Diet (approximately 200 grams per day) and water ad libitum and had a light:dark cycle of 12 hours on–12 hours off.

2. Sample Preparation:

For the SCI extract, a dry sterile glass tube with a screw cap was filled with 20 ml of the appropriate extracting medium. Two gamma-irradiated (2.5 MRad) adhesion film samples (both surfaces exposed) measuring 120 cm² total surface area were cut into pieces then added to the tube. An additional sterile tube was filled with the same volume of medium to serve as a blank. Each sample and blank was extracted at 37° C. for 72 hours. Each extract was vigorously agitated prior to withdrawal of injection doses to ensure even distribution of extracted matter.

3. Injection Protocol:

On the day of the test the fur on the back of each rabbit is removed on both sides of the spinal column. A 0.2 ml portion of one of the sample extracts is injected intracutaneously at each of five sites along one side of the spinal column of each of three rabbits. A 0.2 ml portion of the corresponding blank (saline alone) is injected intracutaneously at five sites along the other side of the spinal column of each of the three rabbits. The injection sites are observed immediately after injection for erythema, eschar formation, edema and necrosis, and scored at 24, 48 and 72 hours.

4. Evaluation of Results:

All of the animals were observed daily for signs of ill health. The injection sites were examined and scored for any tissue reactions, such as erythema, eschar formation, edema and necrosis, at 24, 48 and 72 hours after injection. For each animal, the individual irritation scores for both erythema and edema are added separately for each test extract at each time point and divided by 10 (the total number of observations). A similar assessment is made of the sites injected with the control. A Primary Irritation Score is then obtained for each time point by subtracting the mean irritation scores for the control from that of the test material.

The Primary Irritation Scores of each animal are then added and divided by the total number of animals to obtain the Primary Irritation Index (PII). The primary irritation response to the test material is then determined.

The methods used for these studies are standards in the art, and meet the standards for the NV SOP 16G-43, *Intracutaneous Reactivity Test (ISO)*, *the* AAMI Standards and Recommended Practices, Vol. 4; Biological Evaluation of Medical Devices (11997) pp. 255–256, and USP 23 [1995] pp. 1699–1702.

TABLE 17

| Classification Systems for Intracutaneous (Intradermal) Reactions[1] | |
|---|---|
| | Score |
| Erythema and Eschar Formation | |
| No erythema | 0 |
| Very slight erythema (barely perceptible) | 1 |
| Well-defined erythema | 2 |

TABLE 17-continued

| Classification Systems for Intracutaneous (Intradermal) Reactions[1] | |
|---|---|
| | Score |
| Moderate to severe erythema | 3 |
| Severe erythema (beet-redness) to slight eschar formation (injuries in depth) | 4 |
| Edema Formation | |
| No erythema | 0 |
| Very slight erythema (barely perceptible) | 1 |
| Slight edema (edges of area well defined by definite raising) | 2 |
| Moderate edema | 3 |
| Severe edema (raised more than 1 mm and extending beyond area of exposure) | 4 |
| Total Possible Score for Irritation | 8 |

[1]. Other adverse changes at the injection sites shall be recorded and reported.

TABLE 18

| Primary Irritation Response Categories in Rabbits[2] | |
|---|---|
| Response Category | Mean Score (PII) |
| Negligible | 0 to 0.4 |
| Slight | 0.5 to 1.9 |
| Moderate | 2 to 4.9 |
| Severe | 5 to 8 |

[2]. The Primary Irritation Index (PII) is determined by adding the Primary Irritation Scores for each animal and dividing the total score by the number of animals.

Results:

The animals remained healthy throughout the test period. In none of the animals injected with saline were any irritant responses observed. In only 5 of the 15 sites injected with the test material was any erythema observed, and when present, the erythema was very slight, having a score of 1. In no animal was edema observed after injecting the test material. The Primary Irritation Scores and Primary Irritation Indices are shown in Table 19. The Primary Irritation Indices (PII) of the test material extracted in SCI was 0.

TABLE 19

| Primary Irritation Scores and Primary Irritation Index (SCI) | | | | |
|---|---|---|---|---|
| Rabbit Number | Time (hours) | Control Mean | Test Mean | Primary Irritation Score (Test Mean - Control Mean) |
| 1 | 24 | 0 | 0.1 | 0.1 |
| | 48 | 0 | 0.1 | 0.1 |
| | 72 | 0 | 0 | 0 |
| 2 | 24 | 0 | 0.1 | 0.1 |
| | 48 | 0 | 0 | 0 |
| | 72 | 0 | 0 | 0 |
| 3 | 24 | 0 | 0.2 | 0.2 |
| | 48 | 0 | 0.2 | 0.2 |
| | 72 | 0 | 0.1 | 0.1 |
| Primary Irritation Index (9 Primary Irritation Scores/3 animals) | | | 0.3 | |

Example 24

Effect of the Number of Films Implanted on Gross and Histopathology

Introduction:

The purpose of this study was to determine the effect of placement of 10 to 20 times the expected clinical dose of CMC/PEO films of this invention on the gross and microscopic appearance of the liver, kidney, bladder, bowel, abdominal wall, heart, lung and ovaries.

Methods:

1. Animals:

Twelve female New Zealand White rabbits, 2.4–2.7 kg, were purchased and quarantined for at least 2 days prior to use. The rabbits were housed on a 12:12 light:dark cycle with food and water available ad libitum.

2. Materials:

Gamma-irradiated (2.5 MRad) CMC/PEO films (55.2 cm$^2$ (10×expected dose) or 110.7 cm$^2$ (20×the expected dose per rabbit) were implanted surgically into the peritoneal cavities of rabbits. The sutures that were used to close the peritoneum and skin is 3-0 coated Dexon II suture (Davis and Geck, Manati, PR).

3. Sidewall Model:

Adhesions were induced using the same methods as described above for Example 21.

4. Evaluation of Findings:

After 7 days, the rabbits were killed. The abdominal organs were evaluated grossly for any lesions. The kidney, spleen, liver, lung, heart, bowel, abdominal wall and ovaries (in addition to any found to have gross lesions) were placed in formalin for preservation and prepared for histopathologic evaluation.

Results:

CMC/PEO films prevented adhesion formation to injured sidewalls. This was consistent with previous studies described in the Examples above, which showed maximal efficacy of this barrier in the sidewall formation model. No gross lesions were noted upon necropsy. Upon microscopic examination of the tissues harvested according to the protocol, no microscopic lesions were noted. In the spleen, macrophages with material ingested were seen in the two groups of animals that received membranes of the invention. This was more pronounced in the animals receiving the higher amounts of films. This reflects a biological clearance mechanism for the CMC/PEO membranes at this postoperative time point.

Example 25

Effects of CMC/PEO Membranes on Abscess Formation in Rats

Introduction:

A host resistance model was used to determine whether implantation of CMC/PEO films of this invention, at the same time as bacterial inoculation affected the mortality and abscess formation as a result of the infection. The purpose of this test was to determine if there was an increase risk associated with the use of this product in potentiating infection.

Methods:

1. Animals:

Ninety female Sprague Dawley rats, 175 to 225 gms, were used for this study. Ten rats were used to produce fecal material. Twenty rats were used to assess the $LD_{10}$ and $LD_{50}$ of the new lot of material and sixty rats were used for the safety study. The rats were acclimated at least 2 days prior to surgery. The rats were housed in the USC Vivarium (an AALAC certified/accredited facility) on a 12:12 hour light/dark cycle. Food and water were available ad libitum except in the immediate postoperative interval.

2. Preparation of Gelatin Capsules:

The fecal contents and feces from rats fed hamburger for 2 weeks were collected and mixed 1:1 with sterile peptone yeast glucose broth containing no preservatives (Scott Laboratories) and 10% barium sulfate. The amount of this fecal preparation that caused mortality in 0 to 20% of the rats (25 μl-$LD_{10}$) or 40 to 60% of the rats (75 μl-$LD_{50}$) was determined in 20 rats. The appropriate amount of material was aseptically added to a gelatin capsule (Number 1, Eli Lilly Company). This capsule was then placed in a second larger capsule (Number 00, Eli Lilly Company). This was referred to as a double-walled gelatin capsule. The capsules were prepared 1 week prior to implantation and stored under frozen conditions under quarantine until the day of surgery.

3. Preparation of Film:

Gamma-irradiated (2.5 MRad) CMC/PEO films were cut into a 1.5 cm×1.5 cm piece for each rat.

4. Implantation of Gelatin Capsules:

The rats underwent a standardized procedure for, laparotomy (intramuscular anesthesia with ketamine/rompum, shaving with animal clippers, betadine scrub, alcohol scrub). A 2 cm incision was then made on the midline. A double-walled gelatin capsule was placed on the right side of the abdomen through the incision. In the control animals, no further treatment was given. In the animal treated with gelatin capsules containing CMC and PEO, the capsule was placed on the left side of the abdomen between the visceral and parietal peritoneum.

Four groups of 15 animals each were studied, two control groups receiving an $LD_{10}$, and an $LD_{50}$, respectively, and two groups receiving $LD_{10}$ or $LD_{50}$ and an implanted device containing CMC and PEO. The abdominal wall and skin were then sutured closed using two layers of 4-0 Ethicon suture. Following surgery, the rats received analgesic for 3 days and observed twice daily for signs of morbidity/mortality.

5. Necropsy:

The rats that died during the 11 day postoperative observation period were necropsied to confirm the presence of an acute bacterial infection. The rats that survived the initial acute infection were killed on day 11 after surgery. Each rat was examined for the presence of any abdominal abscesses palpated through the skin, odor upon opening and splenomegaly. In addition, four areas of the peritoneum were examined for abscess formation. These areas included the liver, abdominal wall, bowel and omentum. The abscesses were scored at each site as follows:

| Score | Description |
| --- | --- |
| 0 | No abscess present at the site |
| 0.5 | One very small abscess present at the site |
| 1 | Several small abscesses present at the site |
| 2 | Medium abscess present at the site |
| 3 | Large or several medium abscesses present at the site |
| 4 | One very large or several large abscesses present at the site |

The scoring were conducted in a blinded fashion by two separate observers and the scores recorded.

Results:

Administration of the CMC/PEO material concurrent with the initiation of bacterial peritonitis did not affect the survival of the rats after infection. The results of these studies is shown in Table 20 below. The group receiving an LD50, 9 of 15 survived, and for the group receiving an LD10, 13 of 15 survived.

TABLE 20

Abscess Formation in Control Animals and Animals Receiving CMC/PEO Mixtures

| Group | Liver | Abdominal Wall | Bowel | Omentum | Total |
|---|---|---|---|---|---|
| Control LD50 | 1.66 | 1.22 | 1.55 | 1.77 | 6.22 |
| CMC/PEO LD50 | 0.77 | 1.55 | 1.0 | 2.33 | 5.66 |
| Control LD10 | 0.54 | 1.78 | 0.46 | 0.85 | 3.6 |
| CMC/PEO LD10 | 0.92 | 1.38 | 0.78 | 0.54 | 3.62 |

In general, the animals receiving the higher dose of abscess-causing bacteria had a higher incidence of abscess formation than did animals receiving the lower dose. The CMC/PEO mixture did not cause any change in abscess formation in animals receiving either dose of bacteria.

Example 26

Surface and Blood-Contacting Properties of CMC/PEO Films

Introduction:

The purpose of this study was to determine whether the CMC/PEO membranes of this invention have anti-thrombogenic properties. CMC (700 kd) and PEO (4.4 Md) were blended and the mixture was cast into thin films. The bilayered films had approximately the same thickness as the monolayered films. Also, for the bilayered films, the different layers had about the same mass. The films were evaluated for surface and blood compatibility properties. Scanning electron microscopy (SEM), electron spectroscopy for chemical analysis (ESCA), platelet adhesion and activation, and plasma recalcification (fibrin clot formation) time analysis were performed on these film samples. Film A was a non-radiated bilayered film having 95% CMC/5% PEO on side 1, and 60% CMC and 40% PEO on side 2. Film B was identical to film A, except that it had not been irradiated. Films C and D were monolayered films having 77.5% CMC and 22.5% PEO, non-irradiated, and radiated, respectively. Film E is a control film made of 100% CMC, and was radiated.

Methods:

1. Scanning Electron Microscopy:

Scanning Electron Microscopy (SEM) of the film surface and cross-section morphologies were obtained at the Electron Microscopy Center at Northeastern University, Boston, Mass. The film samples were rapidly frozen in liquid nitrogen and snapped to obtain a clean cut for viewing the cross-section. The samples were mounted on an aluminum sample mount and sputter coated with a thin film of gold and palladium. The film samples were observed with an AMR-1000 scanning electron microscope (Amray Instruments, Bedford, Mass.) at 10 mm working distance and an accelerating voltage of 10 kV. The original magnification of film surface and cross-sectional images were 5,000× and 2,000×, respectively.

2. Electron Spectroscopy for Chemical Analysis:

Electron Spectroscopy for Chemical Analysis (ESCA) is a surface analytical technique that determines the elemental composition and maps the functional groups on the surface at up to 100 Å-thick layer. The technique is useful for determining the surface presence of PEO in the CMC/PEO membranes (see B. D. Ratner et al. *Surface Studies by ESCA on Polymers for Biomedical Applications*. In: W. J. Feast and H. S. Munro (eds) *Polymer Surfaces and Interfaces*. John Wiley and Sons, New York, N.Y. pp:231–251 (1987), incorporated herein fully by reference). ESCA was performed at the National ESCA and Surface Analysis Center for Biomedical Problems (NESAC/BIO) and the analysis was performed at the Center. Film samples were analyzed by a Surface Science Instruments (SSI, Mountain View, Calif.) ESCA instrument equipped with an aluminum $K_{a1,2}$ X-ray source. Typical pressure in the sample chamber during spectral acquisition was $10^{-9}$ Torr. SSI data analysis software was used to calculate the surface elemental compositions of carbon (C1s) and oxygen (O1s) from the wide scan analysis and the peak areas. High resolution analysis by peak-fitting for determining the identity of chemical functional groups was also performed with the SSI software. A electron flood gun set at 5.0 eV was used to minimize surface charging. The binding energy scale was referenced by setting the —C—H-(hydrocarbon) peak maximum in the C1s spectrum to 285.0 eV.

3. Platelet Adhesion and Activation:

Platelet adhesion and activation measurement was performed as previously described (M. Amiji, *Permeability and Blood Compatibility Properties of Chitosan-Poly(ethylene oxide) Blend Membranes for Hemodialysis. Biomaterials* 16: 593–599 (1995), M. Amiji. *Surface Modification of Chitosan Membranes by Complexation-Interpenetration of Anionic Polysaccharides for Improved Blood Compatibility in Hemodialysis. J. Biomat. Sci., Polym. Edn.* 8: 281–298 (1996), both articles incorporated herein fully by reference). Briefly, a platelet observation chamber was assembled consisting of film-covered clean glass slide, two polyethylene spacers, and a glass coverslip. Human blood, obtained from healthy adult volunteers after informed consent, was collected in heparin-containing evacuated containers (Vacutainers®, Becton-Dickinson, Rutherford, N.J.). Heparinized blood was centrifuged at 10 ng for 10 minutes to obtain platelet-rich plasma (PRP).

Two-hundred $\mu$l of PRP was instilled into the platelet observation chamber. Platelets in PRP were allowed to adhere and activate on the polymer surfaces for 1 h at room temperature. Non-adherent platelets and plasma proteins were removed by washing the chamber with phosphate-buffered saline (PBS, pH 7.4). Adherent platelets were fixed with 2.0% (w/v) glutaraldehyde solution in PBS for 1 h. After washing with PBS, the platelets were stained with 0.1% (w/v) Coomassie Brilliant Blue (Bio-Rad, Hercules, Calif.) dye solution for 1.5 h. Stained platelets were observed using a Nikon Labophot® II (Melville, N.Y.) light microscope at 40× magnification. The image of adherent platelets was transferred to a Sony Trinitron® video display using a Hamamatsu CCD® camera (Hamamatsu-City, Japan). The Hamamatsu Argus-10® image processor was used to calculate the number of platelets per 25,000 $\mu m^2$ surface area in every field of observation. The data indicates average number of adherent platelets±S.D. from at least twelve fields of observation and two independent experiments.

The extent of platelet activation was determined qualitatively from the spreading behavior of adherent platelets as described above in Table 10.

4. Plasma Recalcification Time:

Plasma recalcification time measures the length of time required for fibrin clot formation in calcium-containing citrated plasma that is in contact with the surface of interest. It is a useful marker of the intrinsic coagulation reaction. Human blood was collected in evacuated containers (Vacutainers, Becton-Dickinson) in the presence of sodium citrate buffer as an anticoagulant. Citrated blood was centrifuged at 2,500 g for 20 minutes to obtain platelet-poor plasma. A round sections (20 mm in diameter) of the control and CMC-PEO films were cut with an aid of a sharp scalpel. The film sections were placed in 12-well tissue-culture polystyrene (TCP, Falcon®, Becton-Dickinson) microplates and hydrated with 2.0 ml of PBS for 10 minutes. Excess PBS was removed by suction.

Plasma recalcification time of citrated plasma in contact with control and CMC-PEO blend films was measured according to the procedure described by Brown (Brown, *Hematology: Principles and Procedures*. Sixth Edition. Lea and Febioger, Philadelphia, Pa. 1993, pp. 218, incorporated herein fully by reference). Briefly, 1.0 ml of citrated plasma was mixed with 0.5 ml of 0.05 M calcium chloride and incubated with hydrated film samples in a water-bath at 37° C. The samples were occasionally removed from the water-bath and gently stirred. The time required for fibrin clot formation was recorded. The data indicates average of the plasma recalcification time±S.D. from four independent experiments.

Results:

1. SEM Analysis:

FIGS. 14–20 are surface and cross-sectional SEM images of the 7 film samples (A to E) with the original magnification of 5,000× (surface) and 2,000× (cross-section).

Figure 14A:
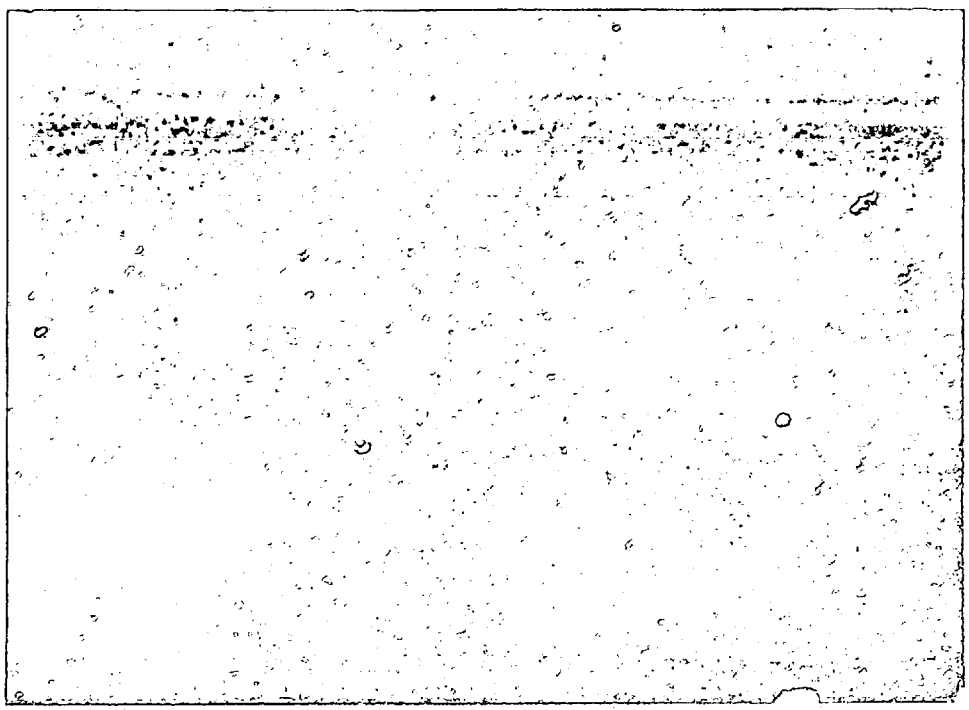
FIGS. 14a–14b show scanning electron microscope (SEM) photographs of the surface and cross-section of an irradiated 95% CMC/5% PEO, pH 5; 60% CMC/40% PEO, pH 3 bilayered membrane, respectively.
Figure 14B:
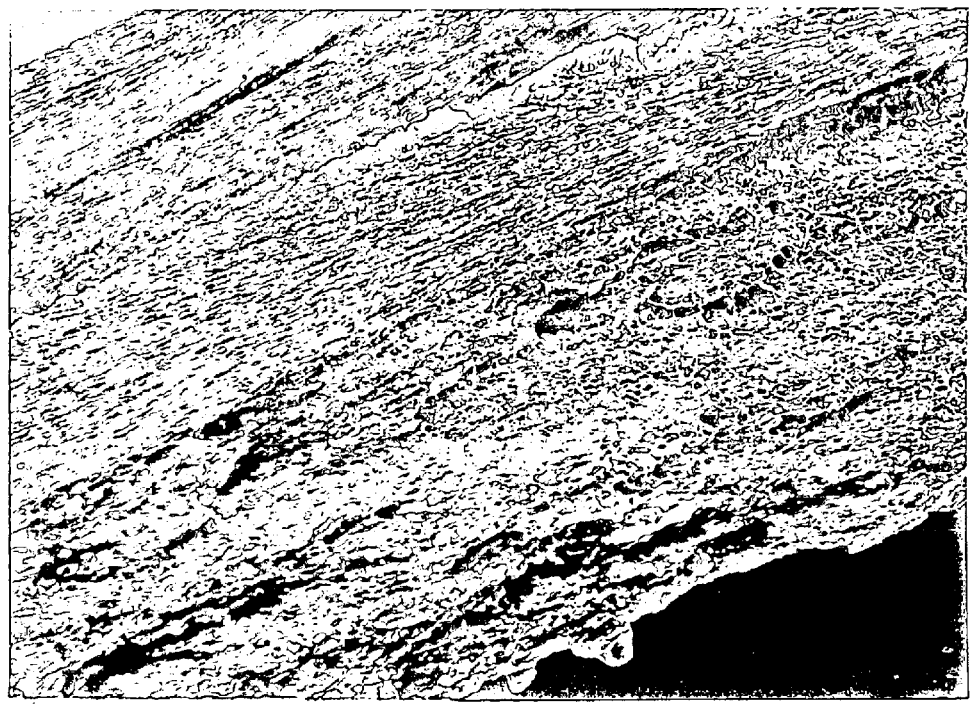

The image in FIG. 14a (film A, side 1; 95% CMC/5% PEO; irradiated) is of a bilayered membrane and shows a portion of the surface of side 1 having marked indentations. These indentations can be due to the incorporation of PEO, although we do not intend to limit our invention to this particular theory. Other theories might account for the observations. The cross-section image (FIG. 14b) shows clear boundaries between the two sides of the laminate film. The top side of the film, shown in the upper left corner of FIG. 14b (95% CMC/5% PEO), is relatively smooth compared to the other side, shown in the bottom right corner of FIG. 14b.

Figure 15A:
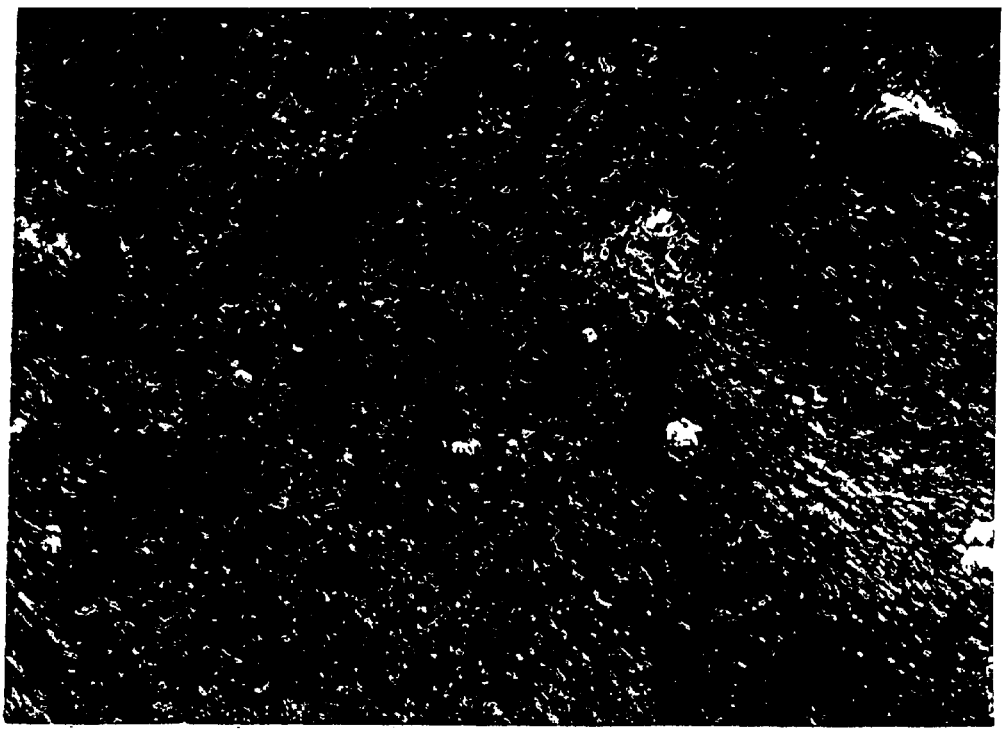
FIG. 15a–15b show SEM photographs of the surface and cross-section of an irradiated 60% CMC/40% PEO membrane, respectively.
Figure 15B:

The image in FIG. 15a (Film A, side 2; 60% CMC/40% PEO; irradiated) shows characteristic "bumps" which can be due to the high concentration of PEO on this side of the bilayered film. The cross-section image (FIG. 15b) shows side 2 in the upper portion of the photograph. The image shows a more "spongy" or porous structure at the top of the photograph, which can be due to the incorporation of PEO. In these films, the PEO chains are homogeneously mixed and the film components do not separate out into distinct phases.

Figure 16A:
FIGS. 16a–16b show SEM photographs of the surface and cross-section of a non-irradiated 95% CMC/5% PEO, pH 5; 60% CMC/40% PEO, pH 3 membrane as in FIGS. 14a–14b.
Figure 16B:
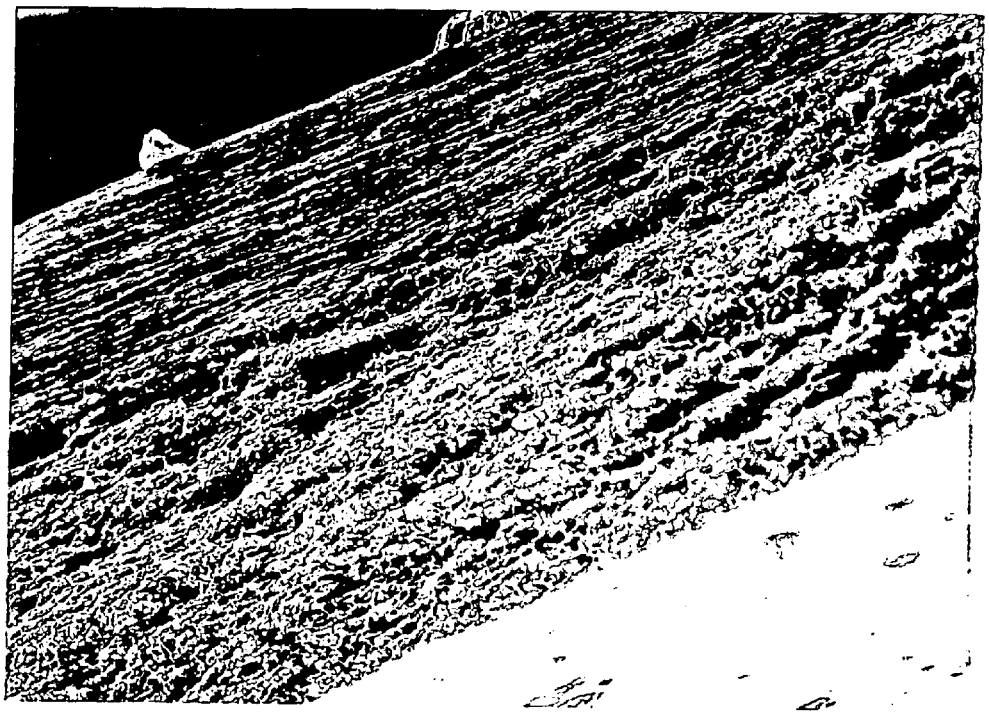

In contrast, the images in FIGS. 16 and 17 (samples B, sides 1 and 2, respectively) were of a film identical to film A, except that it was not irradiated. FIGS. 16a shows side 1 (95% CMC/5% PEO) and 16b shows a cross-section of the film, with the lower, right hand side of the photograph being side 1, and the upper portion being side 2 (60% CMC/40% PEO). There was no significant difference in the surface and cross-sectional morphologies of these films as compared to their radiated counterparts. All of the bilayered films showed distinct separation zones containing low (5%) and high (40%) PEO content.

Figure 17A:
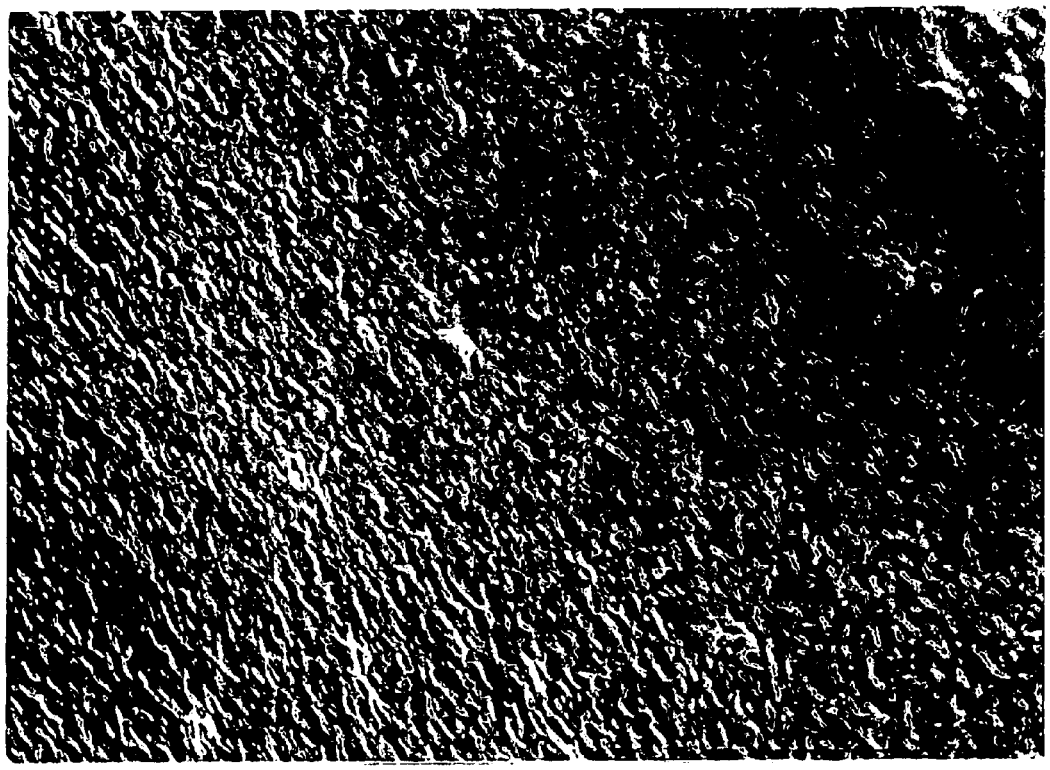
FIGS. 17a–17b show SEM photographs of the surface and cross-section of a non-irradiated 60% CMC/40% PEO membrane as in FIGS. 15a–15b.
Figure 17B:
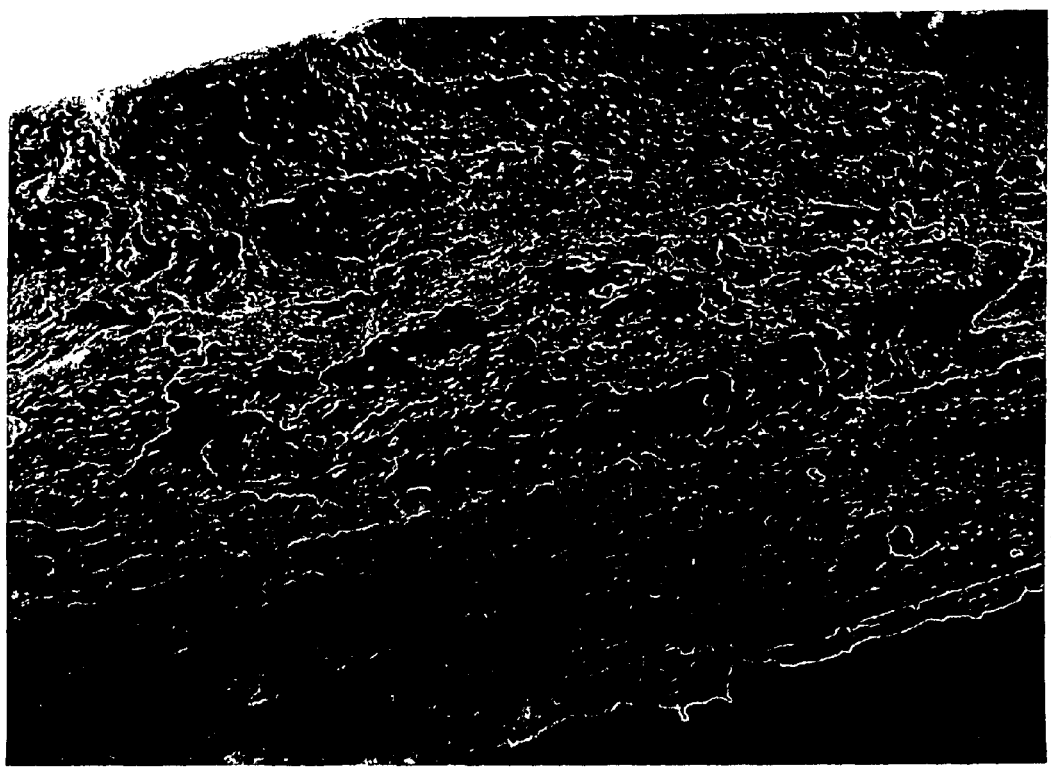

FIG. 17a shows sample B side 2 (60% CMC/40% PEO; not irradiated) in top view of the surface. FIG. 17b shows a cross-section of the film B. The lower right portion of the photograph is side 1 (95% CMC/5% PEO) and the upper left shows side 2 (60% CMC/40% PEO).

Figure 18A:
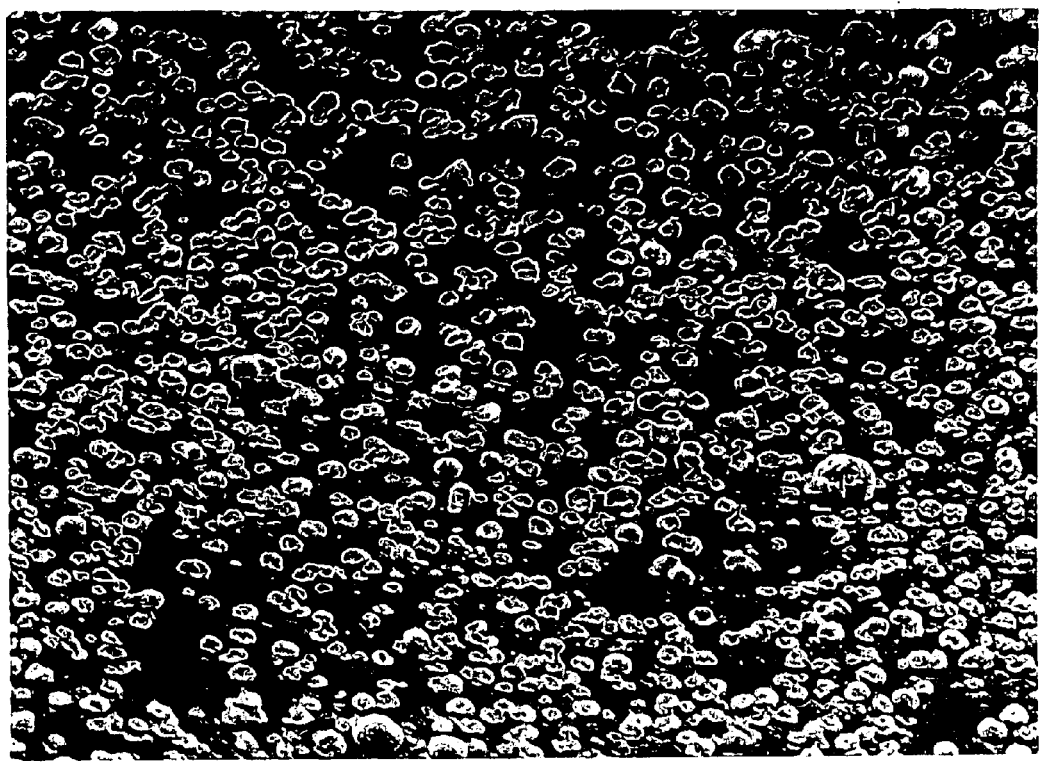
FIGS. 18a–18b show SEM photographs of the surface and cross-section of an irradiated monolayer 77.5% CMC/22.5% PEO membrane, respectively.
Figure 18B:
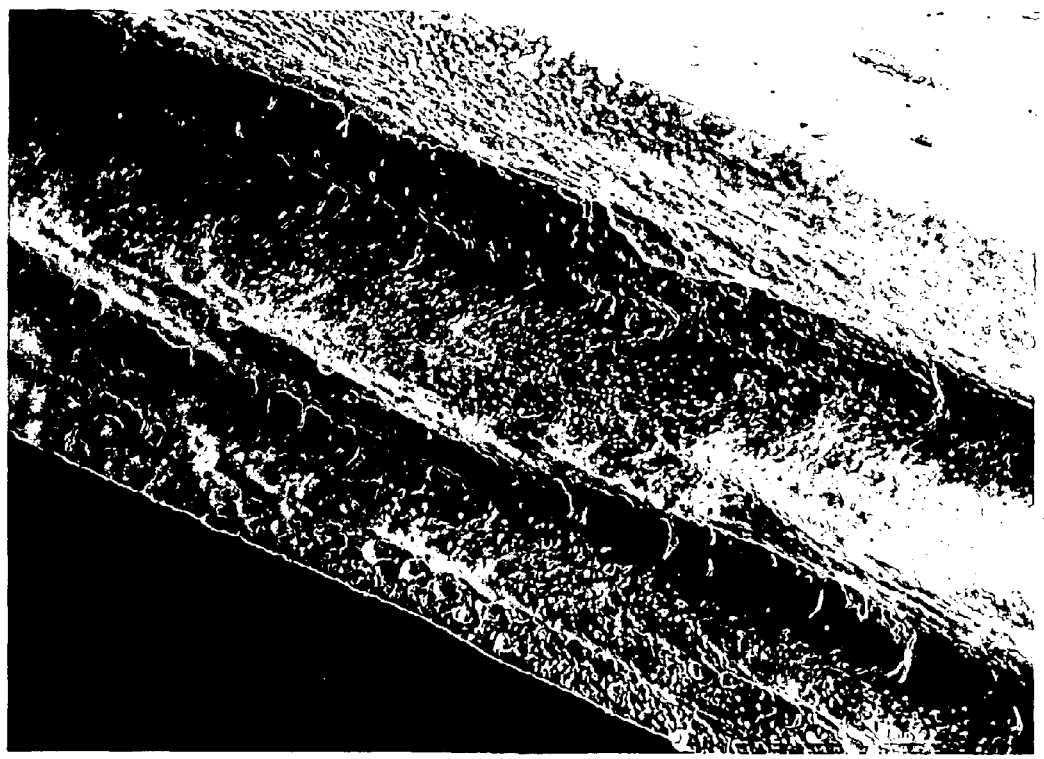

FIGS. 18 and 19 (films C and D, respectively) are images of films prepared by formulating CMC and PEO at a weight ratio of 77.5:22.5. Film C (FIG. 18) was radiated while sample D (FIG. 19) was not radiated. In FIG. 18a, the surface image showed "grains" which were distributed over the surface of the film. These "grains" could be due to leaching of some PEO to the surface. The cross-section image (FIG. 18b) showed a "spongy" or porous film.

Figure 19A:
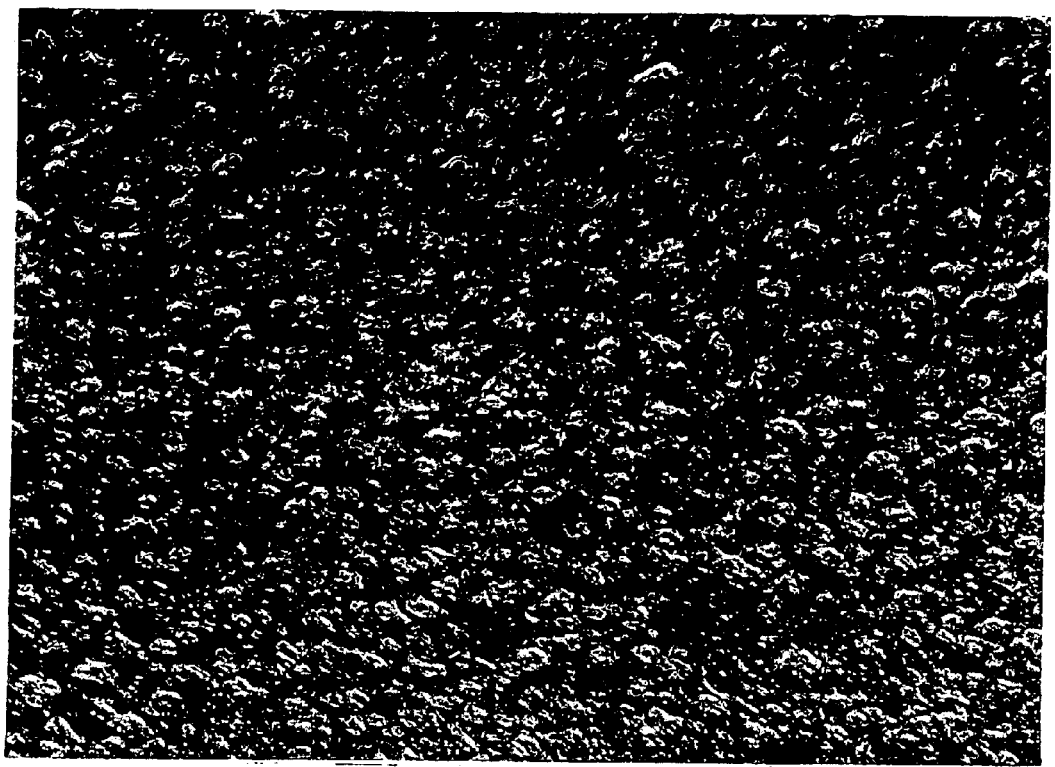
FIG. 19a–19b show SEM photographs of a non-irradiated membrane as in FIGS. 18a–18b.
Figure 19B:
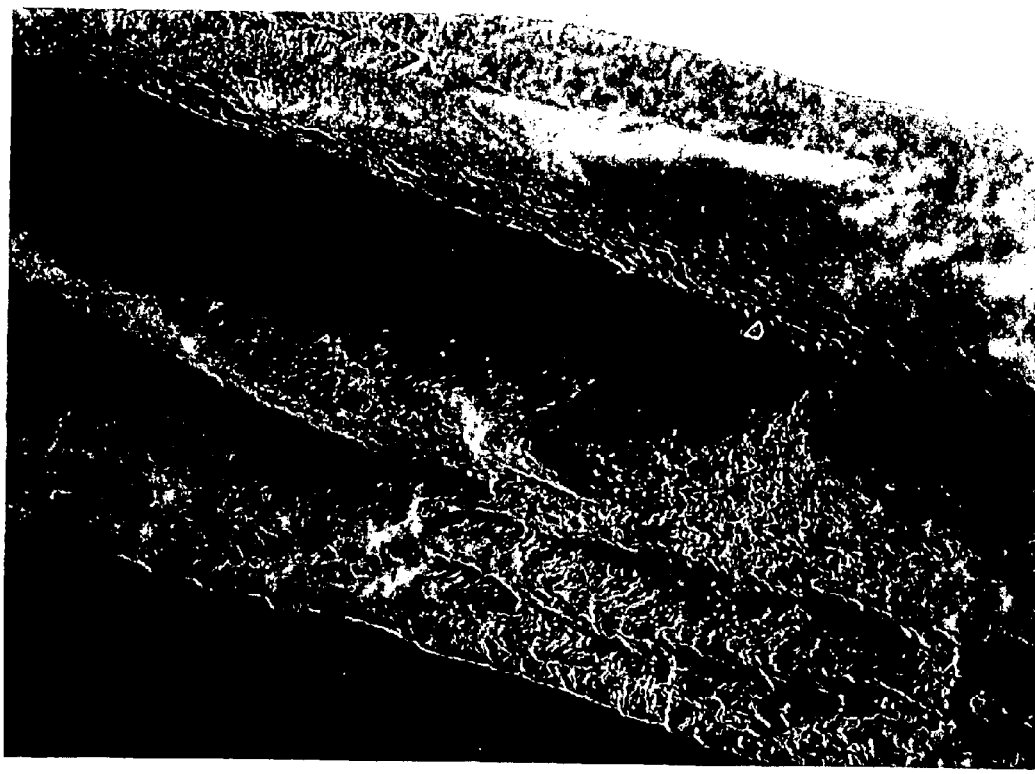

FIG. 19a also showed grains on the surface. The cross-section image in FIG. 19b shows a spongy film. As with the bilayered film A, gamma radiation did not have a significant effect of the morphology of the blended film C.

Figure 20A:
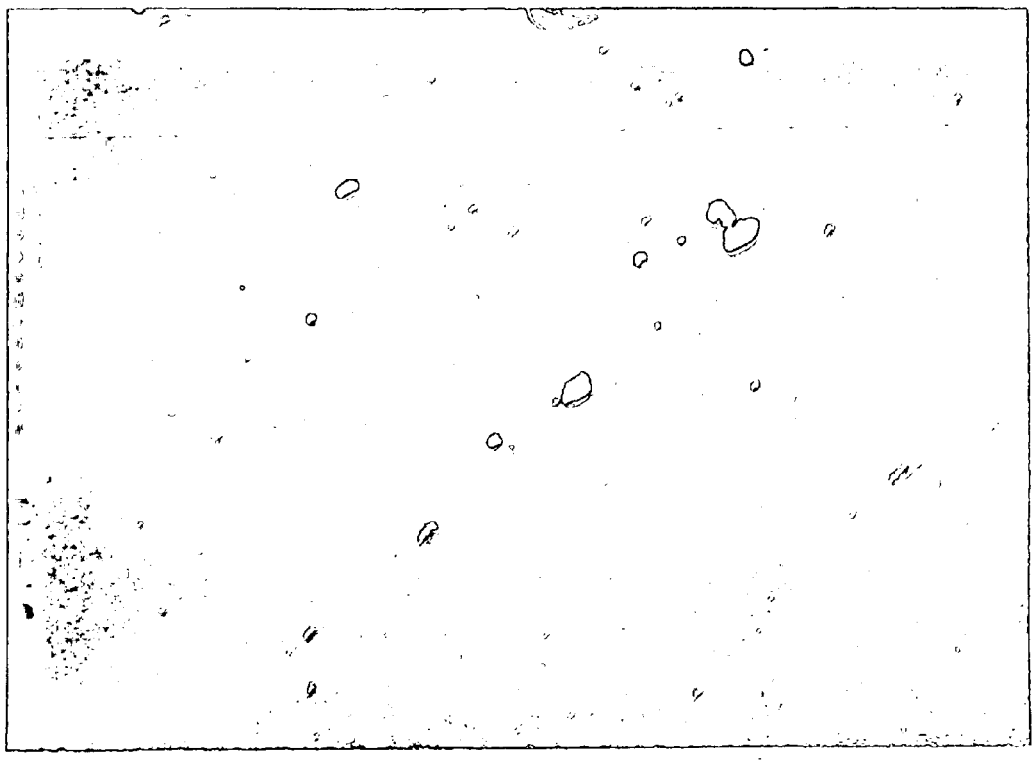
FIGS. 20a–20b show SEM photographs of the surface and cross-section of a 100% CMC membrane, respectively.
Figure 20B:
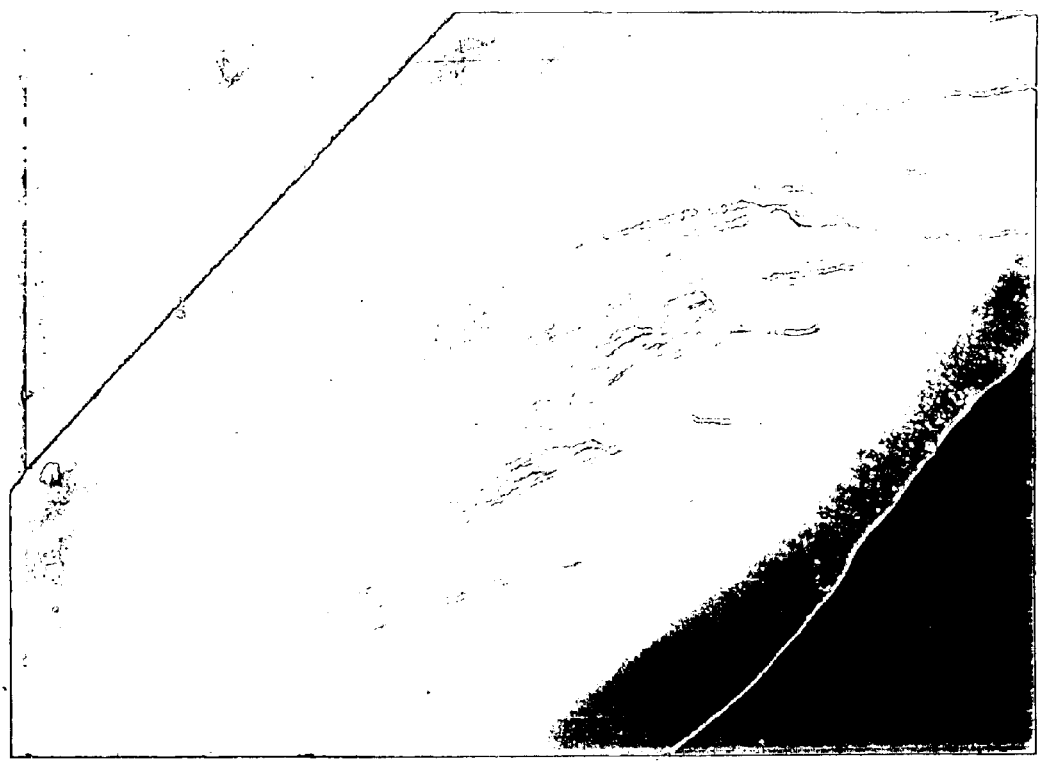

FIG. 20 (film E) is of a 100% CMC film that was gamma-irradiated. The surface (FIG. 20a) and cross-section (FIG. 20b) of this film were smooth. The smoothness of the surface and cross-section of film E could be due to the high crystallinity in the CMC film. Highly crystalline materials can form films with no porosity. However, other mechanisms may be responsible for the smoothness of this film.

2. Surface Chemical Analysis:

ESCA provides the surface elemental composition and identity of chemical functional groups at up to 100 Å-thick surface layer. The wide scan analysis maps out the elemental composition according to their respective binding energies in the spectrum. Carbon (C) for instance, can a binding energy of around 280–290 eV. High resolution analysis of the elemental spectrum can provide additional information on the functional groups associated with the element of interest. In C1s spectrum, the —C—H— (or hydrocarbon) functionality can be associated with the binding energy of 285.0 eV. The —C—O— (ether) functionality, on the other hand, can be associated with a binding energy of 286.4 eV (M. Amiji. *Synthesis of Anionic Poly(ethylene glycol) Derivative for Chitosan. Surface Modification in Blood-Contacting Applications. Carbohyd. Polym.* 32:193–199 (1997), incorporated herein fully by reference). Because the ethylene oxide residues of PEO have —C—O— functionality, any change in the high resolution spectra can indicate an increase in —C—O— composition due to the presence of PEO chains on the surface of the film. This could correspond to the increase in surface accessibility of PEO chains. Surface accessibility of PEO chains can be important for preventing plasma protein adsorption and platelet adhesion and activation. One theory to account for these observations is that the PEO prevents plasma protein adsorption through a steric repulsion mechanism (M. Amiji et al. *Surface Modification of Polymeric Biomaterials with Poly (ethylene oxide), Albumin, and Heparin for Reduced Thrombogenicity*. In S. L. Cooper, C. H. Bamford, and T. Tsuruta (eds.) *Polymer Biomaterials: In Solution, as Interfaces, and as Solids*. VSP, The Netherlands, 1995, pp 535–552; M. Amiji et al. *Surface Modification of Polymeric Biomaterials with Poly(ethylene oxide): A Steric Repulsion Approach*. In S. W. Shalaby, Y. Ikada, R. Langer, and J. Williams (eds.) *Polymers of Biological and Biomedical Significance*, ACS Symposium Series Publication, Volume 540. American Chemical Society, Washington, D.C. 1994, pp 135–146, incorporated herein fully by reference). However, it is possible that other theories may account for the anti-thrombogenic effects of the membranes of this invention, and those other theories are also considered to be part of this invention.

The results of surface analysis of control and CMC-PEO films described above in FIGS. 14–20 are presented in Table 21.

TABLE 21

Surface Elemental Composition of CMC and CMC/PEO Films[a]

| Sample | Percent Elemental Composition | | | | | |
| --- | --- | --- | --- | --- | --- | --- |
| | C | O | N | Na | Cl | C:O Ratio |
| A side 1 | 59.3 | 27.8 | 7.0 | 4.4 | 1.6 | 2.1 |
| A side 2 | 64.6 | 33.3 | — | 1.3 | 0.7 | 1.94 |
| B side 1 | 56.6 | 17.0 | — | 12.9 | 13.5 | 3.33 |
| B side 2 | 66.3 | 32.5 | — | 0.9 | 0.4 | 2.04 |
| C | 65.7 | 33.5 | — | 0.8 | — | 1.96 |
| D | 61.4 | 17.5 | 0.9 | 10.1 | 10.1 | 3.51 |
| E | 69.3 | 17.4 | — | 7.7 | 7.7 | 3.98 |

[a]ESCA was performed at the National ESCA and Surface Analysis Center for Biomedical Problems (NESAC/BIO) at the University of Washington (Seattle, WA).

[a]ESCA was performed at the National ESCA and Surface Analysis Center for Biomedical Problems (NESAC/BIO) at the University of Washington (Seattle, Wash.).

Table 21 shows that Na and Cl were present in almost all of the films. In the non-radiated films B and D, the contribution from Na and Cl was significantly higher than in the radiated films A and C. The presence of N on some films can indicate contamination, in that nitrogen is normally not present in the films. Proteins and other nitrogen-containing impurities in the film can be a source of nitrogen. An increase in the 0 composition was noted on side 2 of films A and B and film C. This could be due to the high concentration of PEO in these samples (40%) as compared to side 1 of films A and B (only 5% PEO).

Film D (77.5% CMC/22.5% PEO; non-radiated) showed the presence of Na and Cl. The presence of Na and Cl can distort the percent contribution from other elements, especially C and O. Thus, the lack of a high 0 peak in film D is not likely due to a low amount of 0 in the film, but is likely an artifact of the presence of Cl in this sample.

The 100% CMC film (film E) had 69.3% C, 17.4% O, 7.7% Na and 5.6% Cl. The high percent of C and corresponding low percent of 0 in this spectrum means that the high amount of 0 in the other films can be due to the presence of PEO.

To determine the types of bonds present in the different films, high resolution C1s, O1s, and N1s spectral analyses were performed by peak-fitting the wide scan peaks (Table 22).

As shown in Table 22, for film A, side 1 (95% CMC/:5% PEO), 42% of carbon was bonded to hydrogen (—C—H) or other carbon atoms (—C—C—), 42% was bonded to oxygen (—C—O—), and 13% was double-bonded to oxygen (—C=O). The presence of ether carbon-bonded moieties (—C—O) at higher percent than that observed for the 100% CMC film (film E) indicated that ethylene oxide residues were on these surfaces. The carboxyl (—C=O—) peak at 13% can be due to the neutralized carboxylic acid groups of the CMC. The O1s peak of film A, side 1 resolved into two peaks associated with —O=C— and —O—C— functional groups.

The N1s spectra, due to the probable contamination of film A, side 1 by proteins, can be due to —N—H— functional groups. The presence of PEO on the surface of film A, side 2 (60:40, CMC-PEO) was supported by the presence of a C1s peak, which can be due to the ether carbon bonds (C—O). In addition, the O1s analysis also showed that there was a higher percentage of —O—C— bonds in side 2 as compared to side 1. Side 2 of films A and B had similar surface bonding profiles. There was no significant difference in the surface bond structure of radiated versus non-irradiated films.

The C1s and O1s spectra of films C and D monolayered films (77.5% CMC/22.5% PEO) were also associated with —C—O— or —O—C— bonds, indicating PEO chains on the surface of these films. The N1s spectra observed for film D was due to contamination by proteins, appearing as —N—H— functional groups. In the control 100% CMC film (film E), 70% of the C1s envelope was due to —C—H— groups, 21% was due to —C—O— groups, and 6% was due to —C=O— groups. Furthermore, the O1s peak resolved into two peaks, having 27% —O=C— and 73% —O—C—.

The results showed that there was PEO on the surface of these films. The PEO concentration on the surface increased with increasing PEO concentration in the composition of the film. Moreover, there was no significant difference in the surface elemental composition or types of functional groups due to radiation.

3. Platelet Adhesion and Activation:

Platelet adhesion and activation is an important indicator of blood-biomaterial interactions (Hoffman. *Blood-Biomaterial Interactions: An Overview*. In S. L. Copper and N. A Peppas (eds). *Biomaterials: Interfacial Phenomena and Applications. Volume* 199. American Chemical Society, Washington, D.C. 1982 pp 3–8, incorporated herein fully by reference). The initial number of adherent platelets and the

TABLE 22

Chemical Bond Analysis of ESCA of Control and CMC/PEO Films

| | Relative Peak Intensity (%) | | | | | |
| --- | --- | --- | --- | --- | --- | --- |
| | C1s | | | O1s | | N1s |
| Sample Film | —C—H (285 eV) | —C—O— (286.4 eV) | —C=O (288 eV) | —O=C— (531.5 eV) | —O—C— (533 eV) | —N—H (399.6 eV) |
| A, side 1 | 42 | 42 | 13 | 18 | 82 | 10 |
| A side 2 | — | 100 | — | — | 100 | — |
| B, side 1 | 65 | 26 | 6 | 18 | 82 | — |
| B, side 2 | — | 100 | — | — | 100 | — |
| C | — | 100 | — | — | 100 | — |
| D | — | 100 | — | — | 100 | 100 |
| E | 70 | 21 | 6 | 27 | 73 | — | extent of platelet activation on biomaterial surface correlates with the potential long-term blood-compatibility profile (Baier et al. *Human Platelet Spreading on Substrata of Known Surface Chemistry. J. Biomed. Mater. Res.* 19: 1157–1167 (1985), incorporated herein fully by reference). When in contact with polymeric surfaces, platelets initially retain their discoid shape present in the resting state and the spread area is typically between $10^{-15}$ $\mu m^2$. Upon activation, platelets extend their pseudopods and initiate the release of granular contents. During the partial activation stage, the area of the spread platelet can increase to about 35 $\mu m^2$. When the platelets are fully-activated, they retract the pseudopods to form circular or "pancake" shape and the spread area increases to 45 or 50 $\mu m^2$ (Park et al. *Morphological Characterization of Surface-Induced Platelet Activation. Biomaterials* 11: 24–31 (1990), incorporated herein fully by reference). The spreading profiles of activated platelets were used to create five activation stages as described by Lin et al. (Lin et al. *Polyethylene Surface Sulfonation: Surface Characterization and Platelet Adhesion Studies. J. Coll. Interface. Sci.* 164: 99–106 (1994), incorporated herein fully by reference). Clean glass promotes platelet adhesion and activation (Park et al. *The Minimum Surface Fibrinogen Concentration Necessary for Platelet Activation on Dimethyldichlorosilane-Coated Glass. J. Biomed. Mater. Res.* 25: 407–420 (1991), incorporated herein fully by reference).

The extent of platelet adhesion was determined by counting the number of platelets per 25,000 $\mu m^2$ surface area. Surface-induced platelet activation was measured qualitatively from the spreading behavior of adherent platelets as shown in Table 23.

TABLE 23

Platelet Adherence and Activation by Control and CMC/PEO Films[a].

| Film | Number of Platelets/25,000 $\mu m^2$ | Extent of Activation |
|---|---|---|
| Glass | 157.3 ± 19.6[b] | 4.8 ± 0.3 |
| A, side 1 | 26.0 ± 5.4 | 2.2 ± 0.1 |
| A, side 2 | 6.2 ± 2.2 | 1.2 ± 0.4 |
| B, side 1 | 27.9 ± 7.3 | 2.4 ± 0.3 |
| B, side 2 | 6.0 ± 2.9 | 1.2 ± 0.1 |
| C | 3.5 ± 1.7 | 1.0 ± 0.0 |
| D | 3.4 ± 1.1 | 1.0 ± 0.0 |
| E | 62.8 ± 12.4 | 3.6 ± 0.4 |

As shown in Table 23, platelets adhered to the glass surface and became activated. Platelets did not adhere in as great a number to CMC/PEO membranes, however, and were not activated to the same degree as by glass. The degree of adherence and activation was inversely related to the PEO concentration. Thus, increasing the amount of PEO decreased both platelet adherence and platelet activation. Moreover, comparing films A and C (radiated) with films B and D (non-radiated) there was no effect of gamma radiation on platelet adhesion and activation.

From the platelet adhesion and activation studies, increased surface PEO correlated with reduced adherence and activation of platelets. Based on these observations, CMC-PEO membranes with high PEO content are relatively non-thrombogenic.

4. Plasma Recalcification Time:

Plasma recalcification time is a measure of the intrinsic coagulation mechanism (Renaud, The recalcification plasma clotting time. A valuable general clotting test in man and rats. *Can. J. Physiol. Pharmacol.* 47: 689–693 (1969), incorporated herein fully by reference). Since the time required for contact activation of plasma varies with the type of surface, the plasma recalcification time is used as an indicator of blood compatibility of biomaterials (Rhodes et al., Plasma recalcification as a measure of the contact phase activation and heparinization efficacy after contact with biomaterials. *Biomaterials* 15: 35–37 (1994), incorporated herein fully by reference). Plasma recalcification time was determined using the methods of Renaud and Rhodes et al., cited above. Tissue Culture Polystyrene (TCP) surfaces are created by treating polystyrene microplates with oxygen plasma to convert the hydrophobic surface into a hydrophilic one. The results of this study are presented in Table 24.

TABLE 24

Recalcification Time for Plasma in Contact with Control and CMC-PEO Films[a]

| Film | Plasma Recalcification Time (minutes) |
|---|---|
| Control TCP[b] | 6.3 + 0.2[c] |
| A, side 1 | 13.9 ± 0.6 |
| A, side 2 | 17.8 ± 0.5 |
| B, side 1 | 13.5 ± 0.9 |
| B, side 2 | 17.8 ± 0.6 |
| C | 15.3 + 0.8 |
| D | 15.1 ± 0.5 |
| E | 5.6 ± 0.3 |

[a]The time required for fibrin clot formation with calcium-containing citrated human plasma was measured in minutes.
[b]Tissue-culture polystyrene (TCP) 12-well microplate was used as a control.
[c]Mean ± S.D. (n = 4).

The contact activation time on TCP was about 6.3 minutes, and on 100% CMC (film E) was about 5.6 minutes. This is similar to the contact activation time previously found for clean glass surfaces. In contrast, the plasma recalcification times on PEO-containing films (samples A–D) were significantly higher than the control TCP or CMC surfaces. The recalcification time correlated with the increased PEO content of the film, with increased PEO resulting in increased recalcification time. Therefore, contact activation of plasma was substantially reduced for membranes with increased amounts of PEO.

Conclusions:

Films containing increased amounts of PEO on their surfaces are anti-thrombogenic and can prevent formation of fibrin clots from forming on the surfaces of the films. The antithrombogenic effects are dependent on the amount of PEO. Thus, manufacturing films having increased PEO concentration can decrease thrombogenicity.

Example 27

Bioresorbability of CMC/PEO Membranes

The bioresorbability of CMC/PEO membranes is determined by making a surgical incisions in the rear legs of rats, and placing a portion of a CMC/PEO membrane into a muscular layer. Several membranes of different composition or degree of cross linking are inserted into each animal, after which the incisions are closed. A sufficient number of animals are to be used for each type of membrane to be evaluated. Daily thereafter, animals are sacrificed, the incisions re-opened and the remaining membranes are observed for the degree of intactness, and their locations. Membranes are removed, blotted to remover excess water, weighed while wet, re-dried, and re-weighed. The amounts of fluid absorbed, of solids remaining, and the appearance of the membranes are noted. Comparisons are made between the length of time in situ, tissue location, the membrane composition, pre-insertion conditioning, and the resorbability are made. The membranes of the instant invention are tailored to have a desired degree of bioresorbability.

Example 28

Manufacture of an Iron 30% Ion-Associated Gel

In one embodiment of an ionically cross-linked gel of this invention, to make a gel having 2% w/v solids ratio and 95% CMC/5% PEO, we measured 9.5 g of dry, powdered CMC (ds=0.82) and mixed it with 0.5 g dry powdered PEO (MW=8,000 d). We then prepared a beaker with 500 ml of deionized water and 3.2 ml of a 25.2% w/v solution of $FeCl_2 \cdot 6H_2O$. The dry powdered CMC/PEO mixture was then added slowly to the beaker containing the iron chloride/water solution while the solution was stirred at high speed. Once the dry components were mixed into the solution, the stirring speed was reduced and the gel was mixed for 30–50 minutes, by which time until homogeneity was achieved.

The osmolality was then adjusted to a physiologically acceptable value of about 300 mmol/kg by adding about 13 ml of a 30% w/v solution of NaCl and further mixing the gel. After another 15 minutes of mixing, the pH of the gel was adjusted to 7.0 by adding 1.7 N $NH_4OH$. The gel was then sterilized in an autoclave for 15 minutes at 250° C.

Example 29

Manufacture of an Aluminum 30% Ion-Associated Gel

To make a gel cross-linked with aluminum ($Al^+$), we carried the identical procedure as described above for Example 28, except that instead of adding an iron-containing solution, we added 3.2 ml of a stock 22.5% w/v solution of $AlCl_3 \cdot 6H_2O$. As with the iron cross-linked gel, the pH of the final gel was adjusted to 7.0 using 1.7 N $NH_4OH$. The gel was then sterilized in an autoclave for 15 minutes at 250° C.

Example 30

Manufacture of a Calcium 30% Ion-Associated Gel

To make a gel cross-linked with calcium ($Ca^{2+}$), we carried the identical procedure as described above for Examples 28 and 29, except that instead of adding an iron- or aluminum-containing solution, we added 3.2 ml of a stock 20.6% w/v solution of $CaCl_2 \cdot 2H_2O$. The calcium ion-associated gels did not require any pH adjustment after their manufacture. The gel was then sterilized in an autoclave for 15 minutes at 250° C.

Example 31

Viscosity of CMC/PEO Ion-Associated Gels

After their manufacture, gels were equilibrated at 25° C. in a water bath. Measurement of gel viscosity were made using standard methods. We determined the viscosity of CMC (7HF, 700 kd)/PEO solutions at 25° C. using a viscometer (Brookfield Digital Viscometer; Model DV-II), using guidelines published in the brochure *Cellulose Gum*, Hercules, Inc., Wilmington, Del., page 28 (1986), incorporated herein fully by reference. Briefly, the composition of the solution to be tested is selected, and by referring to Table XI on page 29 of *Cellulose Gum*, the spindle number and spindle revolution speed is selected. Viscosity measurements made on non-autoclaved gels were made within 2 hr after stirring the solution. Viscosity measurements made on autoclaved gels are made after equilibration to 25° C. After placing the spindle in contact with the solution, and permitting the spindle to rotate for 3 minutes, the viscosity measurement is read directly in centipoise.

Figure 21:
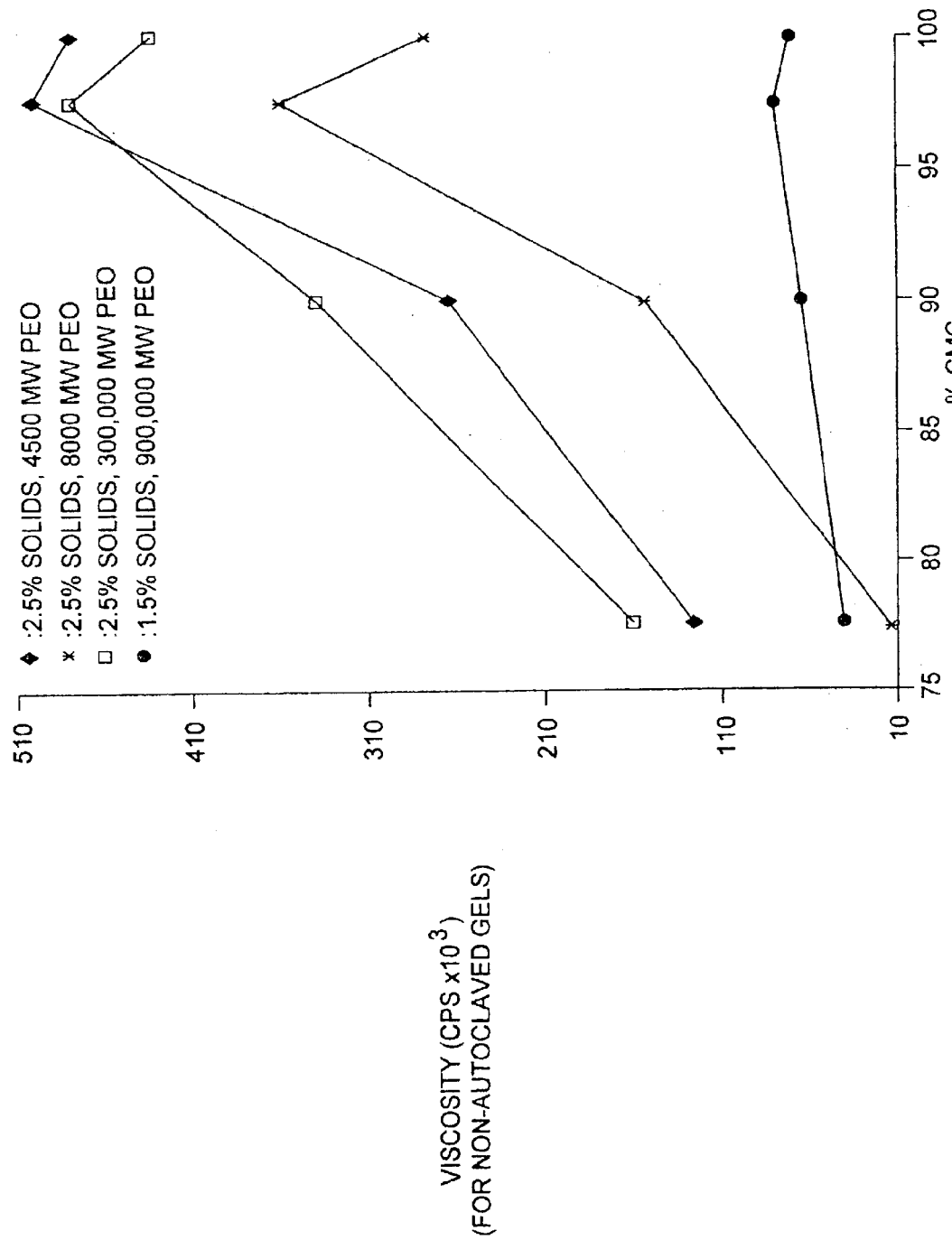
FIG. 21 depicts the relationships between CMC/PEO ratio, molecular weight of PEO and total solids composition on the viscosity of ionically cross-linked gels according to one embodiment of this invention.

FIG. 21 is a graph depicting the relationships between CMC/PEO ratio, molecular weight of the PEO, and viscosity for non-autoclaved, 35% $Fe^{3+}$ ion-associated gels. The top three curves represent data obtained for gels having 2.5% total solids content but made with PEOs having different molecular weights as indicated. The bottom curve represents data obtained for gels having 1.5% total solids content.

The viscosities of the gels ranged from about 10,000 centipoise (cps) to about 510,000 cps. Increasing the percentage of CMC increased the viscosity for each type of gel formulation studied, up to a CMC percentage of about 97. For gels having 2.5% solids content, the effects of cross-linking on viscosities were larger than the effects observed for the gels having 1.5% solids content. However, we unexpectedly observed that increasing the CMC content to 100% resulted in a decease in viscosity for all types of gels studied. The maximum viscosity achieved for each type of gel occurred at relatively low PEO weight content, i.e. CMC of about 97% (by weight; or 88% by unit mole ratio). However, as the PEO was eliminated from the gel composition, the viscosity unexpectedly decreased. Thus, by adding PEO to the gel mixture, we found that the viscosity of the gel increased to values above those predicted based on the prior art for either CMC with ions or PEO with ions alone.

Figure 22:
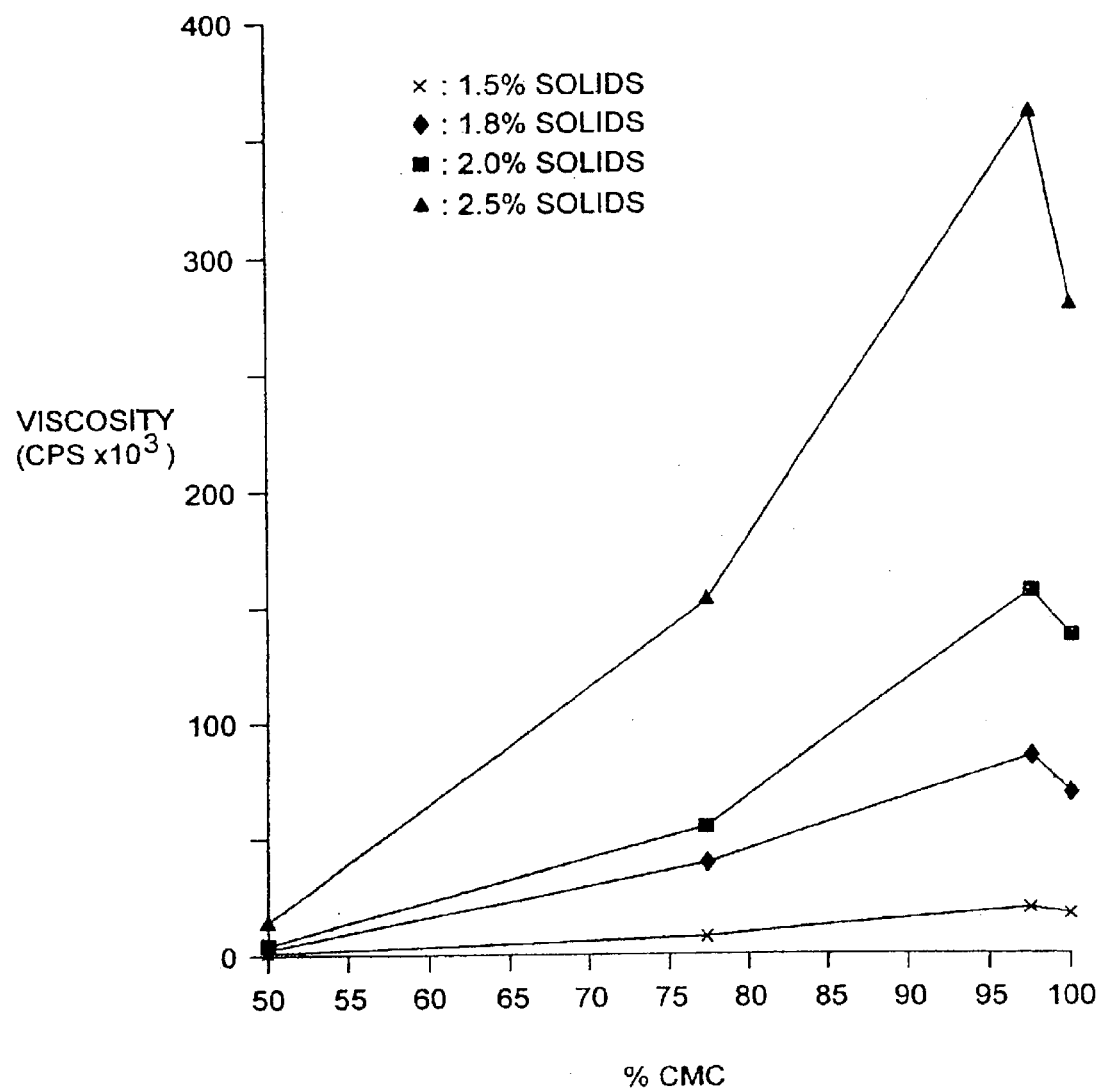
FIG. 22 depicts the relationships between CMC/PEO ratio and percent solids composition and the viscosity of ionically cross-linked gels according embodiments of this invention.

FIG. 22 depicts a graph of the relationship between the % CMC expressed as a weight percentage of the total solids content in a series of non-autoclaved 35% $Fe^{3+}$ ion-associated gels having different total solids contents, and the viscosity of the gel. The viscosities ranged from less than about 2000 cps to over 350,000 cps. As with FIG. 21, increasing the percent CMC relative to the PEO in the gel increased the viscosity. In general for all compositions of gels studied, increasing the solids contents increased the viscosity. The increase in viscosity was the greatest for the gels having the highest percentage of CMC. However, as observed in FIG. 21, increasing the relative amount of CMC relative to PEO above about 97% CMC unexpectedly decreased the viscosity for gels of each solids composition. As with FIG. 21, a maximal viscosity for each gel composition was observed at a PEO concentration of 2.5% of the total solids contents.

FIG. 23 depicts a graph of the relationship between calculated % ion-association of autoclaved gels made with 2% total solids, 97% CMC having a degree of substitution of 0.82, and 3% 8 kd PEO, and the measured viscosity of the gels ion-associated by three ions, iron ($Fe^{3+}$), aluminum ($Al^{3+}$) or calcium ($Ca^{2+}$).

For each ion used, relatively broad regions of increased viscosity were observed. In the absence of cations, the measured baseline viscosity was about 1,800 cps. In the lower concentration ranges of ions (relatively low amounts of ion association), as the percent ionic association increased, the viscosity increased until a maximum value was reached. Increasing the percentage of ionic association above that point however, decreased measured viscosity. For $Al^{3+}$ (▲), the viscosity increased from about 1800 cps to about 55,000 cps for ionic association percentages in the ranges of below about 20% and above about 80%. Above about 20% ionic association, the viscosity increased to a maximum observed viscosity of about 180,000 cps observed at about 40%.

For $Fe^{3+}$ (■), the viscosity decreased at values of ionic association of between about 0 and about 20%, to values below about 500 cps. Increasing the amount of ionic association above about 20% increased viscosity to about 60,000 cps for gels having ionic association values in the range of about 35% to about 70%, with a maximum viscosity of about 90,000 cps observed at an association of about 43–45%. Increasing the ionic association further decreased viscosity to about 70,000 cps at an ionic association of about 70%. Further increasing the degree of ionic association decreased viscosity to about 700 at cps at 90% association.

For $Ca^{2+}$ (♦) the curve appeared shifted to lower percent ionic association values. A maximum viscosity of about 65,000 cps was observed at the lowest percent association (5%). Increasing the ionic association resulted in decreased viscosity, with a measured viscosity of about 2000 cps observed at ionic association percentages above about 20%.

Regardless of the ion type used, increasing the percent of ionic association increased the measured viscosity up to a certain value of ionic association. However, beyond the maximal values, further increases in ionic association did not further increase viscosity. Rather, the observed viscosity decreased as ion concentration was increased beyond the maximal value. One theory that could account for these observations is that at relatively low ionic concentrations, ionic cross-linking between polymer chains increases as the ion concentration increases. The formation of intra-chain associations reaches a maximum at a certain ion concentration, and at this ion concentration, the viscosity is the highest. However, by increasing the ion concentration to values above that required to produce the highest viscosity can decrease viscosity by promoting intra-chain interactions instead of inter-chain interactions. Intrachain interactions can result in the formation of hairpin loops and other configurations of the reactive groups on the polymer with other groups on the same chain. By forming associations between different portions of the same chain instead of forming intra-chain associations, the higher ion concentrations can keep the individual chains from interacting with nearby polymer chains and can result in decreased viscosity of the gel, compared to the viscosity obtained at an ionic concentration that promotes increased intra-chain interactions The decreased viscosity with increased ionic association is therefore similar to a "salting-out" effect that can be observed for other polymers in solutions containing ions. However, other theories can account for the observations, and the invention is not intended to be limited to any particular theory.

Figure 24:
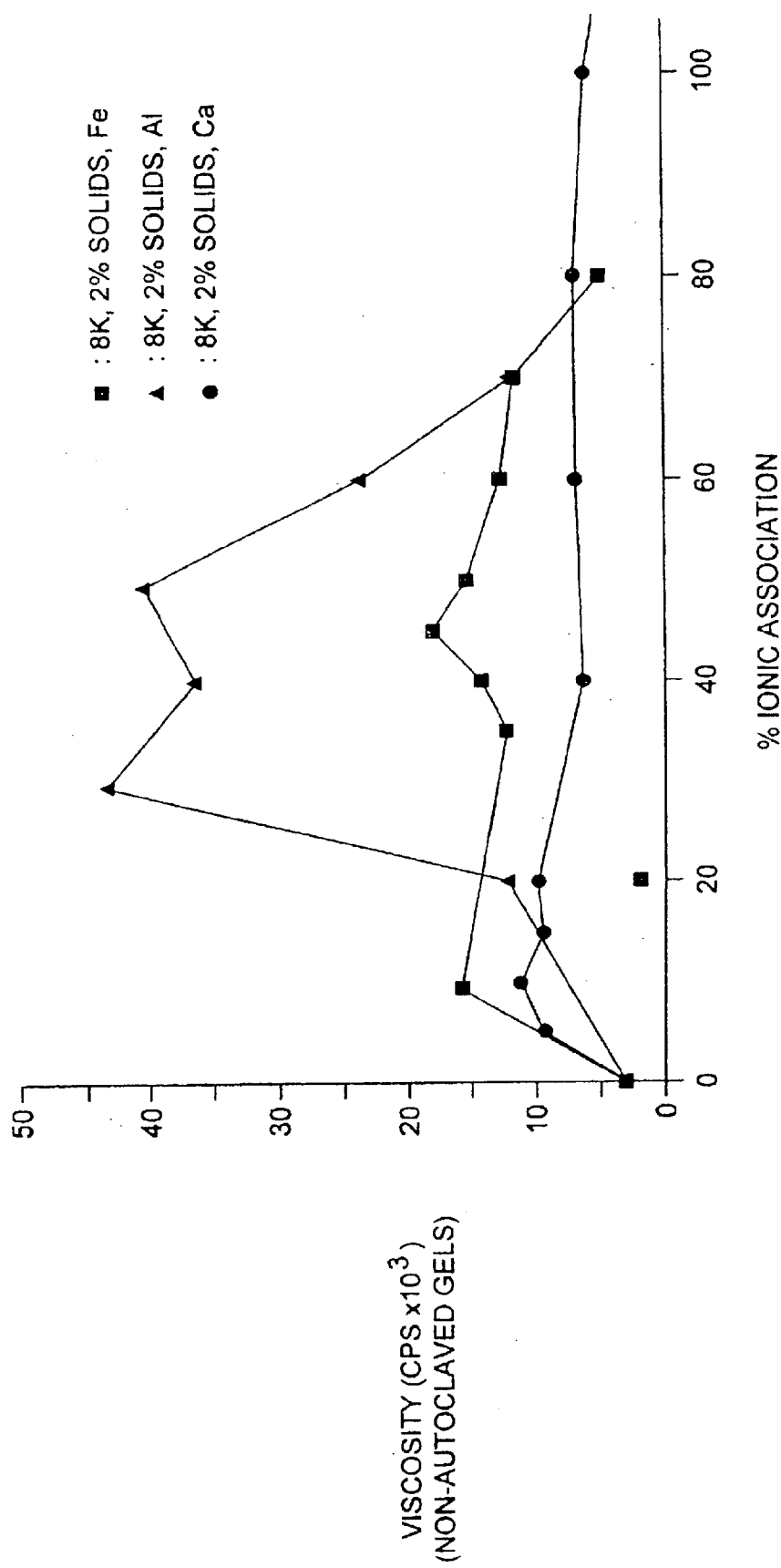
FIG. 24 depicts the relationship between the percent ionic association of CMC/PEO gels, the ionic composition and the viscosity of non-autoclaved gels of embodiments of this invention.

FIG. 24 depicts a graph of the relationship between calculated % ionic association of ionically cross-linked non-autoclaved gels having 2% total solid and, 8 kd PEO and the measured viscosity of the gel for three ions, iron ($Fe^{3+}$), aluminum ($Al^{3+}$) and calcium ($Ca^{2+}$). The non-autoclaved gels generally had higher measured viscosities at each percent ionic association than the autoclaved gels as shown in FIG. 23. Additionally, as with the autoclaved gels depicted in FIG. 23, there were maxima of viscosity at certain percentages of ionic association. In the absence of ionic association, the baseline viscosity of the gels was about 40,000 cps.

For $Al^{3+}$ (▲), the maximum in viscosity appeared as a broad peak of above about 350,000 cps in the range of ionic association of about 30% to about 50%. For $Fe^{3+}$ (■), the viscosity was greater than about 100,000 cps in the range of ionic association percentages from about 10% to about 70%, with peak viscosities of between about 150,000 cps and about 175,000 cps observed at about 10% and about 43–45% ionic association, respectively. For $Ca^{2+}$ (♦), there was an indistinct region of high viscosity at ionic associations in the range of about 10% to about 20%. However, the viscosity was increased above baseline levels for all degrees of ionic association.

Example 32

Manufacture of Ion-Associated Sponges

To manufacture ion-associated sponges using gels of this invention, a gel is manufactured according to methods described above in Examples 28–30. The gel is then poured into a dish made of a thermally resistant material, such as by way of example, polypropylene. The gel is then placed in a freeze-drying apparatus, and is freeze-dried according to methods known in the art.

Freeze dried sponges comprising ion-associated PA and PO can swell upon exposure to aqueous solutions. As described in U.S. Pat. No. 5,906,997, compositions comprising carboxypolysaccharides and polyethylene ethers can hydrate or swell when placed on a wet tissue, thereby adhering to that tissue. The degree of hydration is related to the degree of bioadhesion, and to the degree of antiadhesion effectiveness. Similar relationships between ionically cross-linked, dried sponges and antiadhesion properties.

Freeze-dried sponges can be used as a means to prevent adhesion formation in different parts of the body, such as in spine, orthopedic and abdominal surgeries. In addition, sponges can be useful for hemostasis.

Example 33

Manufacture of Ion-Associated Microspheres

Microspheres of ionically cross-linked gels can be made by extruding gel compositions comprising polymers directly into solutions containing multivalent cross-linking ions. The diameters of the microspheres can be determined by the droplet size of the gel during extrusion. For example, Kondo A. *In Liquid Coating Process (Orifice Process)* In: *Microcapsule Processing and Technology* Van Valkenburg, J. W. Ed., Marcel Dekker, NY, pp 59–69 (1979), incorporated herein fully be reference, describes different methods for forming droplets of gels. Using smaller orifices, the size of the microspheres can be smaller. Additionally, microspheres can be freeze-dried for use. Freeze dried microspheres comprising ionically cross-linked PA and PO can swell upon exposure to aqueous solutions. As described in U.S. Pat. No. 5,906,997, compositions comprising carboxypolysaccharides and polyethylene ethers can hydrate or swell when placed on a wet tissue, thereby adhering to that tissue. The degree of hydration is related to the degree of bioadhesion, and to the degree of antiadhesion effectiveness. Similar relationships between ion-associated, dried microspheres and antiadhesion properties.

Microspheres can be used for drug delivery into locations in which direct injection of gels is impractical. By way of example, inhalation of an aerosol of microspheres can provide a convenient means for delivering PA/PO compositions into the airways. Further, in situations in which it is desirable to deliver a highly viscous gel composition through a fine needle, a suspension of microspheres can be used. A suspension of microspheres can have a viscosity less than that of an equilibrated solution of the same overall composition. This can be because the microspheres can be separated from one another and therefore can have mobility in the suspension. In contrast, a uniform solution of cross-linked gel having the same overall composition can have ionic cross-linking throughout the solution, thereby conferring a higher viscosity upon the solution than is present in the suspension of relatively isolated microspheres.

By using a suspension of microspheres, one can deliver the relatively less viscous suspension through a fine needle or cannula to the desired location without requiring the high pressures needed to force a viscous solution through the same sized needle or cannula. Additionally, suspensions of microspheres or gels can be sprayed onto surfaces to provide even deposition.

Example 34

Manufacture of Ion-Associated Membranes

In other embodiments of this invention, ion-associated gels as described above can be formed into membranes prior to use. In general, dried membranes can have longer residence times in situ than gels that haven't been dried. Methods for manufacturing membranes from casting solutions or gels is described in U.S. Pat. No. 5,906,997, herein incorporated fully by reference. To form membranes of this invention, any of the compositions described herein can be poured onto a flat surface and dried, either at atmospheric pressure (about 760 Torr) or reduced pressure.

Once manufactured, membranes can be used as an adhesion preventative barrier, or can be conditioned prior to use. Membranes made according to this invention can be desirable in situations in which the residence time of the composition at the site is desired to be long.

In yet other embodiments of this invention, a polyacid/polyalkylene oxide membrane can be manufactured according to methods as described in U.S. Pat. No. 5,906,997 and then conditioned by immersing the membrane in a solution comprising a cation or a polycation. By selecting the type of cation or polycation, the concentration of the cation, the time of immersion and other conditions, the cation can penetrate into the surface of the membrane, can associate with charged groups of the polymers in the membrane, and thereby can increase the degree of bonding between the polymers in the membrane. Thus, a membrane surface comprising an ion-associated polymer can be formed. Once so formed, a membrane having a surface conditioning can have increased residence time in the body and therefore can exert antiadhesion effects for periods of time longer than membranes that had not been so treated.

Example 35

Effects of Gamma-Radiation on CPS/PE Membrane Components

To study the effects of sterilization on membranes and solutions of materials used to make membranes and gels of this invention, we carried out a series of studies on the effects of sterilization on the molecular weight profiles.

Methods:

1. Chromatographic Analyses:

Molecular weight profiles were obtained in aqueous conditions for the components of the CPS/PE complexes by size exclusion chromatography using a multi-angle light scattering ("SEC-MALS") method. The chromatography apparatus consisted of three columns in series. They were a column containing Ultrahydrogel 2000, Ultrahydrogel 1000 and Ultrahydrogel 250, from Waters Corporation. The detection system consisted of a Dawn Wyatt Laboratories multi-angle light scattering detector and a Model 410 refractive index ("RI") detector (Waters, Inc.). Molecular weights and molecular weight distributions were determined using methods known in the art.

2. Sample Preparation:

Some samples of films or casting solutions were exposed to 2.5 MRad of γ-radiation as described above. Subsequent to γ-radiation, the γ-treated and untreated samples were prepared having a total solids concentration of 0.2% (weight/volume) in a mobile phase consisting of 100 mM sodium nitrate containing 0.02% sodium azide. Samples were prepared having a neutral pH. To analyze the molecular weight profile of an acidic film, the film was first neutralized by adding a base, after which the solution was titrated to neutrality using dilute acids. The neutral pH conditions were desirable, as the molecular weights of the components could be determined without being obscured by the change in apparent molecular size due hydrogen bonding between polymer components. Films were analyzed either without any sterilization, after sterilization at 2.5 MRad gamma irradiation, or after autoclaving at 250° F. for 20 minutes. In some cases, duplicate samples were prepared and analyzed.

A. Preparation of a Membrane for Analysis:

Samples prepared that were made from membranes of 77% CMC/23% PEO with and without blue dye were made by first cutting 220 mg samples of film (#648-2) into small pieces. For each membrane, 110 ml of mobile phase and 40 µL of 5 N NaOH were added, and the solution was stirred with a Teflon™ bar at low speed. After 30 minutes, the pH was measured to be 9.5. 10 µl of 1 N HCl was added to lower the pH to 8.5, and a further 5 µl of 1 N HCl was added to lower the pH to 7.2. The sample solution was then poured into a 100 ml sample bottle and stored in the refrigerator. An aliquot of 5 ml was analyzed.

B. Preparation of a Casting Solution for Analysis:

A casting solution of 100% CMC (batch # 9805061) having a pH of 4.24 was prepared by making a 1.33% (weight/volume) solution by mixing 20.5 gm CMC, 114.8 gm diluent solution and 40 µl of 5 N NaOH in a beaker and stirring the solution with a mixer. The pH after 7 minutes was 5.34. 5 µl of 5N NaOH was added after 10 additional minutes and the pH increased to 5.46. 5 µl of 5 N NaOH was added after an additional 20 minutes, at which time the pH increased to 5.82. 10 minutes later, another aliquot of 5 N NaOH (10 µl) was added, and the pH increased to 9.48. This basic solution was acidified by adding 20 µl of 1 N HCl to result in a pH of 6.65 after a total of 51 minutes. A 5 ml sample was analyzed.

C. Preparation of Standards

Samples designated "standards" were composed of CMC, PEO, or mixtures of CMC and PEO, dissolved in the SEC mobile phase solution. The raw materials were irradiated in dry form to obtain "irradiated standards."

Figure 25A:
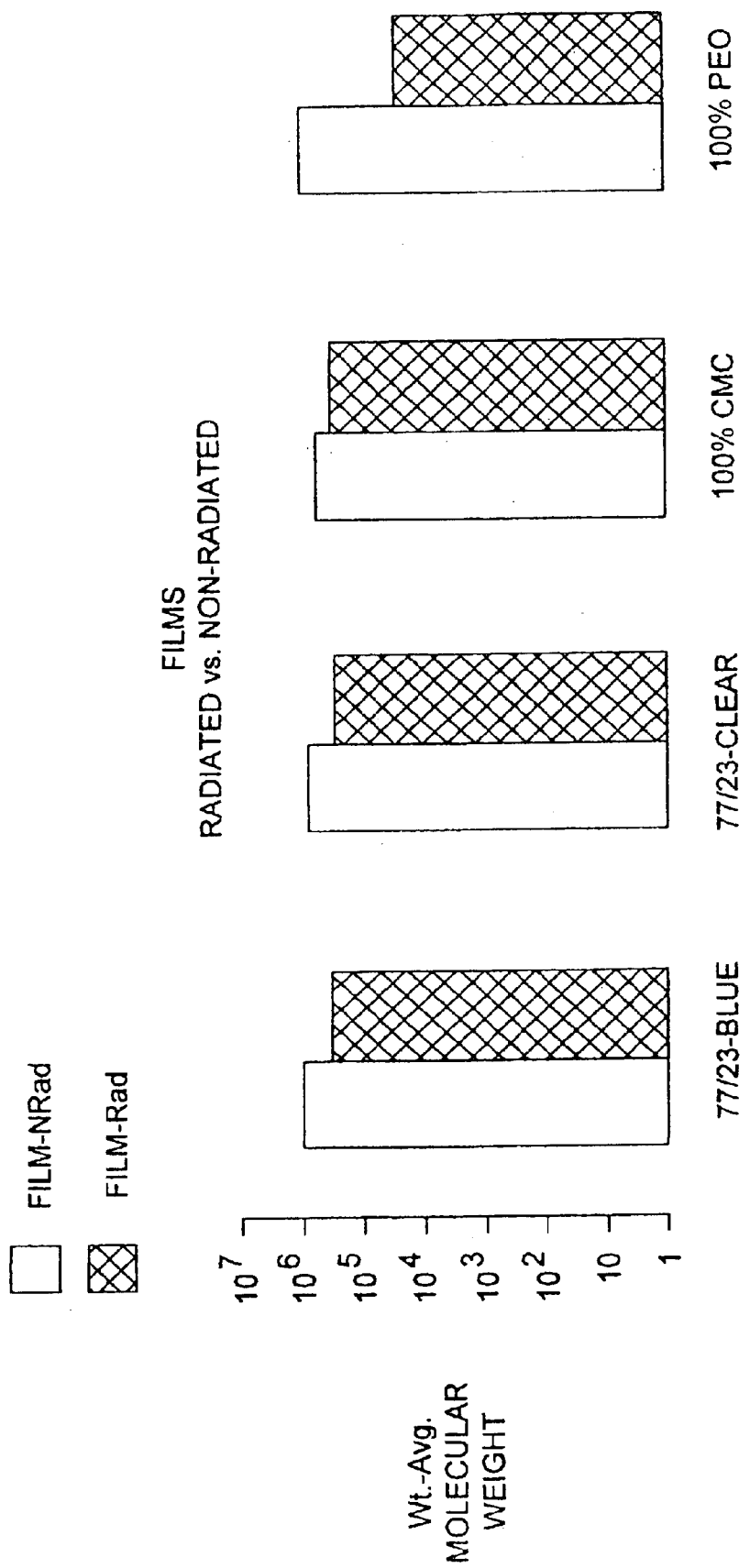
FIG. 25a–25c depict the effects of γ-irradiation on molecular weight of CMC/PEO components of this invention.
Figure 25B:
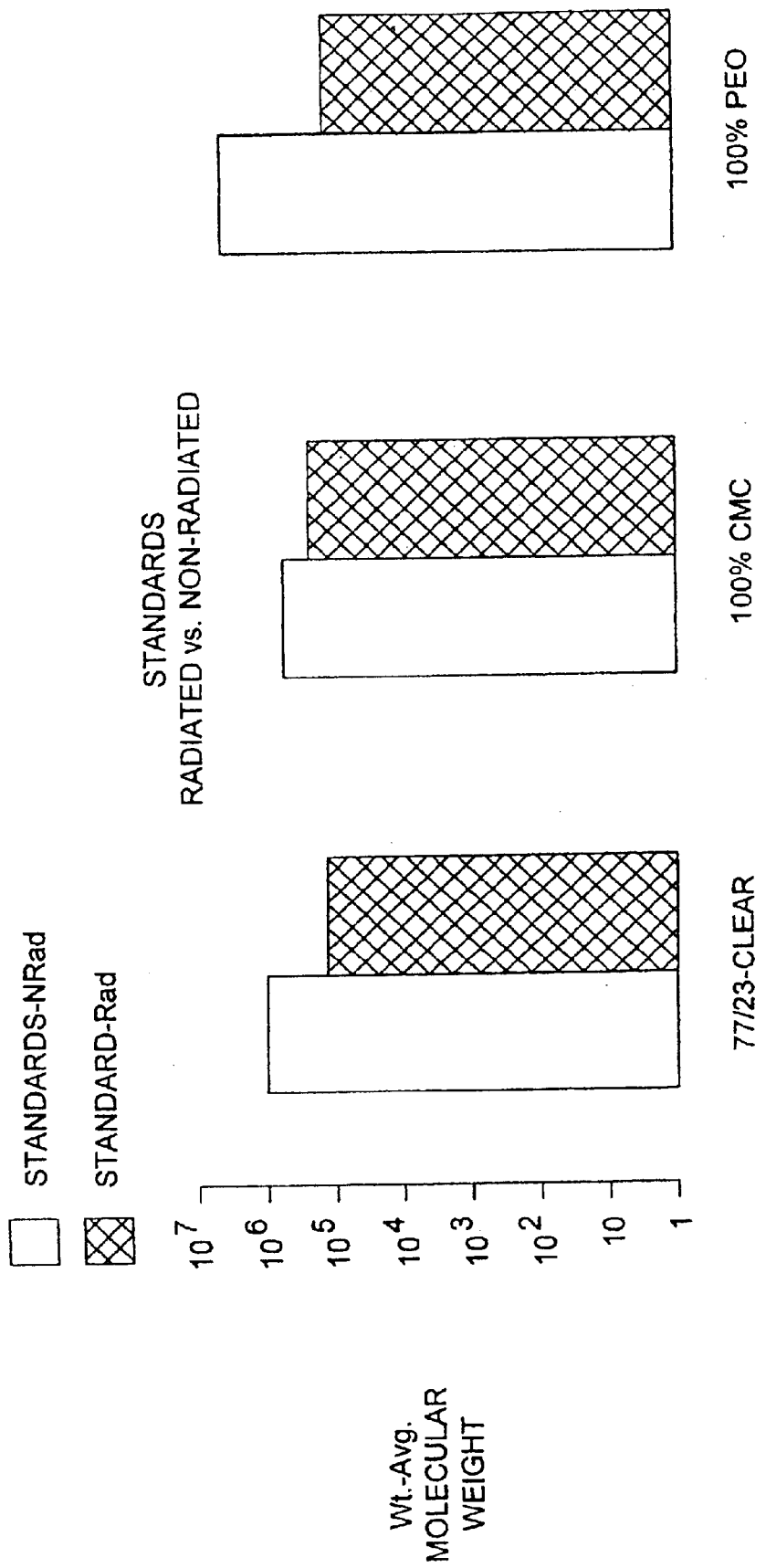
Figure 25C:
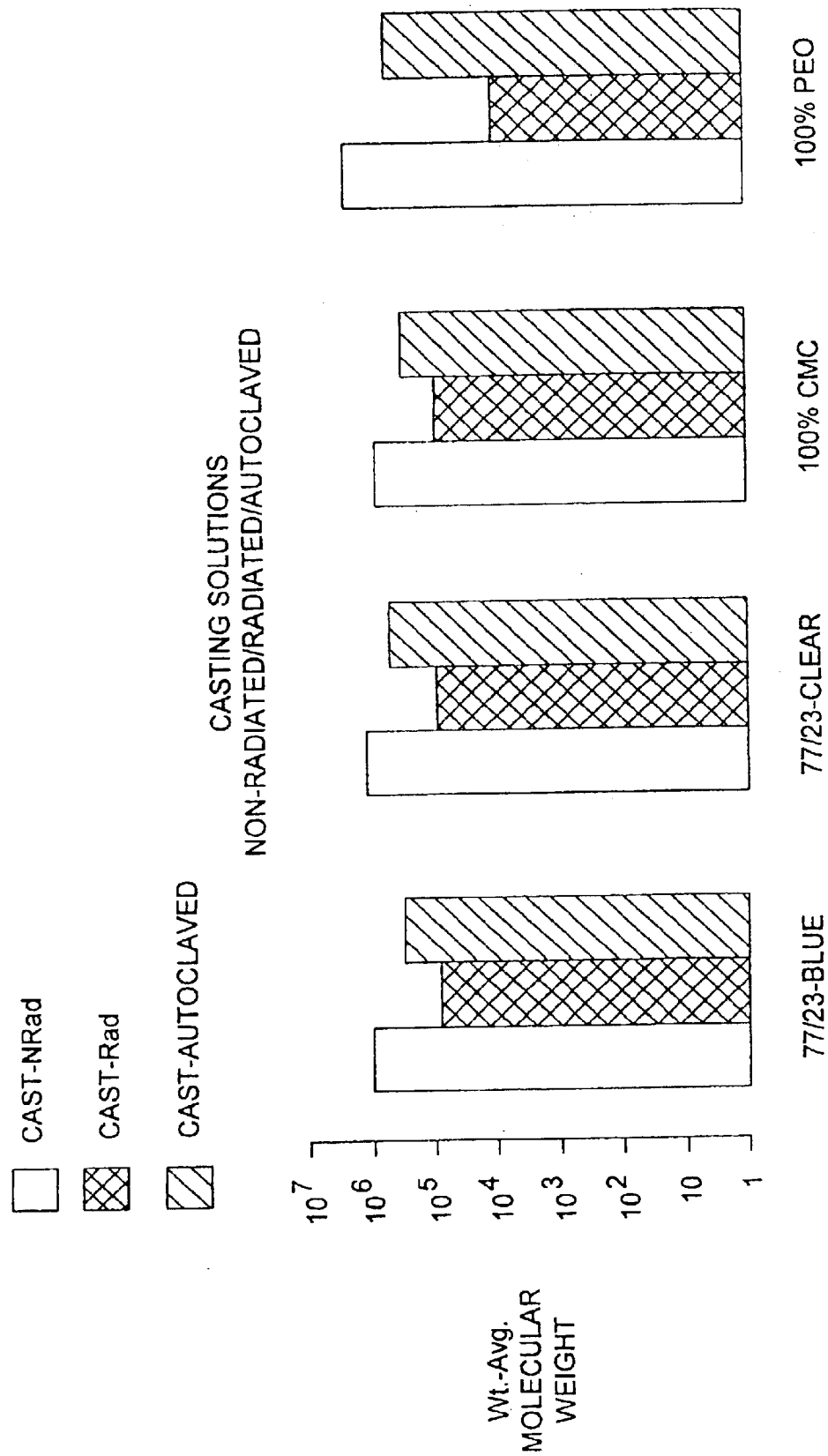

Results:

Results of the above studies are depicted in FIGS. 25a–25c.

FIG. 25a depicts the results for radiated and non-radiated films. Gamma irradiation decreased the average molecular weight of the components for the mixed CMC/PEO films, pure CMC films and pure PEO films. However, the effect was least for the 100% CMC film (columns second from right). The mixed films containing PEO exhibited decreases in molecular weight for both the dyed film (left columns) and the clear film without blue dye (columns second from left). The pure PEO film (right column) also exhibited a decrease in molecular weight, with the molecular weight decreasing from about 1000 kd to about 26 kd. Based on the above results, the PEO molecules had, on average, about 38 strand breaks.

FIG. 25b shows results of γ-irradiation on CMC and PEO standards. γ-irradiation decreased the average molecular weight of a 77% CMC/23% PEO mixture (left columns), as did the 100% PEO standard (right columns, now decreased to about 140 kd), whereas the 100% CMC composition (middle columns) showed only slightly greater than 50% reduction in average molecular weight.

FIG. 25c shows results of γ-irradiation and autoclaving on gel casting solutions. The blue-dyed casting solution containing 77% CMC/23% PEO (left columns) exhibited a decrease in average molecular weight when γ-irradiated, whereas the autoclaving caused a smaller decrease in molecular weight. Similarly, autoclaving of the clear 77% CMC/23% PEO solution (columns second from left), the 100% CMC solution (columns second from right) and the 100% PEO solution (right columns) caused smaller reductions in molecular weight than did gamma irradiation. The average molecular weight of the PEO casting solution after gamma-irradiation was about 12,000.

The above results indicate that gamma irradiation can decrease the average molecular weight of gel components, gels, and membranes. However the magnitude of the decrease indicates that there are on average, about 83 strand breaks per PEO polymer unit. Gas chromatography confirmed that none of the components were completely de-polymerized into monomer units.

Example 36

Manufacture of Compositions Using a Slurry of CPS and PE I

In alternative embodiments of this invention, the CPS and PE can be mixed together with a non-solvent liquid to form a slurry prior to their dissolution in the aqueous medium. The liquid to be used in making the slurry should desirably not dissolve the components to a significant degree. Suitable liquids include alcohols, and in certain embodiments, isopropanol.

To manufacture membranes using this procedure, we placed 8.25 1 (1) of sterile water in a stainless steel vessel into which 10 ml of FD&C Blue #2 Dye was placed, and mixed the solution slowly for 5 minutes.

We then weighed 75.25 g CMC and 24.75 gm of PEO powders, for a total of 100 gm and mixed the components together with a spatula, in a 600 ml beaker. We then added 300 ml of isopropyl alcohol to the powdered CMC and PEO while mixing to wet the powders, and form the slurry.

We then increased the speed of mixing the water/Dye solution until a vortex in the solution was achieved. We then slowly added the isopropanol/CMC/PEO slurry to the water/Dye solution while continuously mixing. As the slurry was mixed, it became thicker, and the speed of the vortex mixer was adjusted to maintain a speed of about 50–150 rpm, alternatively about 100 rpm. As the solution became thicker, we adjusted the speed of the mixer to maintain the desired rpm, and maintained the rpm for an additional 1.5–2.0 hrs. After 2 hours of mixing, the solution appeared to be homogeneous.

We then added 10 ml concentrated HCl to the mixture and stirred for an additional 30–60 minutes. The pH was adjusted to be in the range of 4.1–4.3.

Example 37

Manufacture of Compositions Using a Slurry of CPS and PE II

In a variation of the method described in Example 36, we weighed 85.25 gm of CMC and 24.75 gm PEO powders for a total of 10 gm and mixed the dry components together with a spatula. We carried out the same procedure as described for Example 36 except that after adding the CMC/PEO/isopropanol slurry to the water/Dye solution, we mixed the components for 10 minutes at high speed, and then reduced the speed to 130–150 rpm for an additional 2 to 4 hours. After about 2 hours, the solution appeared to be nearly homogeneous.

Example 38

Filtration or CMC/PEO Casting Solutions Before Drying Films

In certain cases, it can be desirable to increase the homogeneity of the casting solution by removing any under-dissolved components prior to drying the casting solution into a membrane.

Methods:

To accomplish this, we used either a 30 µm pore-sized or a 50 µm pore-sized filter (Millipore Corp,) and forced casting solutions made according to Examples 36 and 37 through the filter using pressurized nitrogen (5–10 pounds per square inch "psi"). As materials trapped on the filter slowed the flow, the pressure was increased to about 20 psi.

We then evaluated the effects of filtration on the particle size distribution and viscosity of the casting solution, and the % hydration and bioadhesiveness of membranes made from unfiltered and filtered solutions.

Results:

Table 25 shows the results of the analysis of particle size.

TABLE 25

Particle Size Analysis of Filtered Components

| Particle Size | Distribution of Particle Sizes for Unfiltered Solutions | Distribution of Particle Sizes for Filtered Solutions |
| --- | --- | --- |
| 5–10 µm | 85.85% | 94.91% |
| 10–25 µm | 11.01% | 4.95% |
| 25–50 µm | 2.82% | 0.05% |
| 50–100 µm | 0.22% | 0.07% |
| over 100 µm | 0.1% | 0.1% |

The viscosities of the above casting solutions were measured at 1.0 rpm with spindle #3, and were found to be 14,800 cps for the unfiltered solution, 14,300 cps for the solution filtered with a 30 µm filter, and was 15,600 cps for the solution filtered with the 50 µm filter.

Membranes made from unfiltered solutions and solutions filtered with either the 30 µm or 50 µm filters showed little difference in hydration. A membrane made from unfiltered solution hydrated by 870%, a membrane made from a 30 µm filtrate hydrated by 780%, and a membrane made from a 50 µm filtrate hydrated by 788%.

TABLE 26

Effects of Gamma-Irradiation on Bioadhesion* for Membranes Made From Filtered and Unfiltered Solutions

| Film Treatment | Not Irradiated (average, n = 5) | Radiated (average, n = 5) |
|---|---|---|
| Unfiltered | 84.6 | 98.6 |
| 30 µm Filter | 99.2 | 89.8 |
| 50 µm Filter | 74.4 | Not done |

*Bioadhesion was measured as the force in grams necessary to remove the film from the substrate.

In contrast, Interceed™ did not adhere, and Seprafilm II™ required 69 gms of force to detach the film from the substrate.

Example 39

Hydration and Mass Loss of Glycerol-Containing Films

In certain other embodiments of this invention, we made films containing glycerol. Glycerol is a plasticizer, and when used in membrane preparations, plasticizers can increase the flexibility of the membrane. Increasing flexibility can make insertion and positioning of the membrane easier and more accurate.

In a study to determine the hydration and solubility in PBS characteristics of glycerol-containing CMC/PEO films, we manufactured a series of 77% CMC/23% PEO films according to previous methods, except for the incorporation of increasing amounts of glycerol. For films having glycerol, the total solids composition remained the same, so that as the glycerol or content increased, the CMC/PEO content decreased accordingly. Table 30 shows the results of this study.

TABLE 27

Effects of Glycerol on Hydration and Solubility of CMC/PEO Films

| Film Type | pH | % Hydration | % Mass Loss |
|---|---|---|---|
| 0% Glycerol, NS* | 6.47 | 2860 | 76.1 |
| 2% Glycerol, NS* | 6.72 | 3057 | Not measured |
| 10 Glycerol, NS* | 6.89 | 1734 | 76.7 |
| 20% Glycerol, NS* | 7.00 | 641 | Not measured |
| 30% Glycerol, NS* | 6.38 | 238 | 54.3 |
| 0% Glycerol, S** | 6.53 | 1479 | 53.4 |
| 2% Glycerol, S** | 6.55 | 1494 | Not measured |
| 5 Glycerol, S** | 6.46 | 1529 | Not measured |
| 10 Glycerol, S** | 6.66 | 867 | 52.8 |
| 20 Glycerol, S** | 6.83 | 595 | Not measured |
| 30 Glycerol, S** | 6.32 | 156 | 49.7 |

*NS: Not Sterilized
**S: Sterilized

The date presented in Table 27 showed in general, that increasing the percentage of glycerol in the films decreased the hydratability of the film. This effect may have been due to the decreased percentage of CMC and PEO in the films having more glycerol. The trend was consistent for both the non-sterilized and the sterilized films.

Regardless of the mechanism responsible, glycerol containing films of this invention can have advantages. First, they are pliable and flexible, making them easy to manipulate. For example, glycerol containing films can be more easily rolled up and inserted into a surgical site using a device suitable for the films of this invention. Such a Filmsert™ device is described in co-pending patent application Ser. No. 09/280,101, filed Oct. 24, 1998. The description of this device and its use in delivering the films of this invention to a surgical or wound site is incorporated herein fully by reference.

Types of Surgery

Many types of surgical procedures can benefit from the use of the membranes or gels of the present invention. The gels of the present invention are designed (but not limited) to be used as adjuncts to prevent postoperative adhesions, a common cause of short and long term surgical complications. The type of surgeries where the gels may prove useful are specifically in the spine, nerve, tendon, cardiovascular, pelvic, abdominal, orthopedic, otorhinolaryngological and ocular fields. The gels can act as an interposed temporary barrier between tissues which are likely to adhere to one another after surgical trauma.

Depending on the exact formulation (PA/PO weight ratio, degree of substitution, degree of polymerization, % total solids, degree und type of ion association etc.), the gels according to the invention may vary in consistency from flowable, liquid-like polymer solutions to rigid gels. Thus, the gels can be tailored to the aforementioned surgeries and needs by selecting specific mechanical/physical properties which are pertinent to those applications, e.g. cohesiveness, viscosity, coating and tissue adherence ability, softness/coarseness, stiffness, rigidity, and the steric exclusion of certain cell types and proteins., The following are exemplary, and are not intended to be limiting.

Example 40

Spinal Surgery

In embodiments of this invention that can be used for applications to spinal surgery, it can be desirable to use a mixed gel/membrane preparation to exert the desired anti-adhesion and other effects. For example, in procedures involving surgery to the spinal cord and surrounding intravertebral sites, it can be desirable to place a gel composition directly on the nerves within a vertebral space, and then to apply a membrane preparation over the gel to help keep the gel in place during wound healing and recovery.

Methods:

A. Animals:

We studied 5 adult New Zealand White rabbits in each of three groups. Animals were anesthetized with ketamine/xylazine and shaved and prepared in a sterile fashion. Penicillin (150,000 U) were injected subcutaneously as a prophylactic antibiotic, and the anticholinergic agent glycopyrolate was used intravenously. An indwelling intravenous catheter was inserted into the saphenous vein and 0.9% saline solution was infused to maintain an open vein and to maintain adequate hydration. Each animal was placed on a warmed operating table and were supported to enable ease of their abdominal breathing pattern. Oxygen saturation, respiratory rates and electrocardiograms were monitored during anesthesia. Isoflurane gas and oxygen was used as the anesthetic.

B. Surgical Preparation:

A dorsal incision was made at the L-4 to L-6 area. Two laminectomies were performed, with an untouched vertebra and soft tissues separating the two operated sites. This prevented leakage of blood and/or test materials from one site to the other. One site was used as a control. The fifth animal in each group was treated at both operated sites with the test material. Thus, there was a total of 6 treated sites and 4 control sites per group.

C. Post-Operative Care and Evaluation of Adhesions

After the laminectomies, the gel and/or membrane preparations were placed at the site of surgery and the surgical sites were closed using 3-0 Vicryl sutures, and the skin was closed using 4-0 silk sutures. Each animal was placed in a warm incubator to recover from the anesthesia. When awake, each animal was placed in a separate cage. Each animal was sacrificed 4 weeks after surgery, and the presence and severity of adhesions and the extent of recovery were measured using the scoring system described below. The person evaluating the efficacy of the antiadhesion materials was ignorant of which materials were used on which animal.

Adhesion Scoring System:
1. The locations for assessment of wound healing:
   (1) Site of incision;
   (2) Subcutaneous tissue;
   (3) Fascia;
   (4) Paraspinous muscle; and
   (5) Bone regrowth.
2. The locations for assessment of scar and adhesion formation:
   (1) Middle scar: just beneath the layer of muscle and above the laminectomy site. At the margins of the laminectomy site and attached to the dorsal aspect of the remaining laminar bone, but not extending into the bone defect,
   (2) Deep scar: within the laminectomy defect and extending into the space previously occupied by the ligamentum flavum and epidural fat; and
   (3) Dural adhesions: connective tissue attachments between bone or deep scar and the dura within the spinal canal.
3. Healing Grade Scale:
   0 Complete healing
   1 Minimal non-healed tissue
   2 Moderate non-healed tissue
   3 Extensive non-healed tissue
4. Scar/Adhesion Grade Scale:
   0 None
   1 Minimal or thin
   2 Moderate
   3 Thick Each animal was graded on the five aspects of wound healing, and the three aspects of scar formation. Each animal received a total healing score and a total scar score. Rank order analysis and analysis of variance of the ranks were calculated for each treatment and respective control, and for the differences between treatment and control. The lower the score, and the lower the difference, the better the adhesion prevention.

After gross evaluation of the adhesions, one spine from an animal from each of the test gels were dissected free and placed into 5% formalin for histological analysis.

D. Antiadhesion Gel Preparations

We studied three different gel preparations of this invention, each having 97.5% 0.82 ds. CMC, 2.5% PEO, with a 60% ionic association with $Ca^+$ ions, one commercially available antiadhesion gel, Adcon-L™ (a dextran sulfate-containing preparation from Gliatech, Inc.), and one membrane preparation of this invention (77.5% CMC/22.5% PEO, pH=42).

Gel A: was made using 1,000 kd PEO and 2.5% total solids content. The viscosity of this gel was 158,000 cps and the osmolality was 320 mOsm/kg.

Gel B: was made as Gel A above, except that the total solids content was 3%, the osmolality was 312 mOsm/kg, and the viscosity was 314,000 cps.

Gel C: was made as Gels A and B above, except that the PEO was 4.4 Md, the total solids content was 3% the osmolality was 326 mOsm/kg, and the viscosity was 306,000 cps.

E. Results

The results of the study are presented below in Table 28.

TABLE 28

Anti-Adhesion Effects of Gels and Gels Plus Membranes in Spinal Surgery

| Gel Preparation | Control | Treated | Difference |
| --- | --- | --- | --- |
| Gel A | 21.3 ± 7.05 | 30.4 ± 7.2 | −17.75 ± 3.65 |
| Gel A + Membrane | 35.8 ± 9.3 | 32.3 ± 7.75 | 12.6 ± 4.65 |
| Gel B | 29.4 ± 4.35 | 13.9 ± 5.8 | 11.4 ± 2.65 |
| Gel C | 33.3 ± 4.9 | 14.8 ± 7.2 | 9.2 ± 2.8 |
| Adcon-L ™ | 26.5 ± 6.35 | 9 ± 0 | 10.3 ± 5.6 |

Data is expressed as mean score ± standard deviation.

Thus, gels of this invention can reduce the number and severity of adhesions. Thus, the use of gels and membranes of this invention can improve the anti-adhesion effects compared to the effects of gels alone.

Example 41

Ocular Surgery

Ocular uses include surgery for glaucoma filtering. Successful glaucoma filtering surgery is characterized by the passage of aqueous humor from the anterior chamber through a surgically created fistula to the subconjunctival space, which results in the formation of a filtering bleb. Bleb failure most often results from fibroblast proliferation and subconjunctival fibrosis. To prevent this fibrosis, a membrane of the present invention can be placed post-operatively in the subconjunctiva in the bleb space and a membrane also placed in the fistula.

Additionally, the compositions of this invention can prevent the formation of adhesions and scarring after cataract, refractive, glaucoma, strabismus, lacrimal, and retinal procedures, and can inhibit intra-ocular bleeding. The fluid and gel compositions of this invention can also act as a lubricant for insertion and/or removal of intra-stromal rings or ring segment implants. The gels and fluids of this invention can also act as protective agents to inhibit drying and trauma during eye surgery.

Example 42

Musculoskeletal Surgery

Repair of tendon flexors can be enhanced by using membranes of the present invention, In tendon repair, collagen secreted by fibroblasts unites the ends of tendons. Adhesion formation usually binds the tendon to other tissue structures, obliterating the normal space between the tendon and tendon sheath, thereby interfering with the gliding function necessary for smooth movement. To prevent adhesions from forming between the tendon and the sheath, a membrane of the present invention is wrapped around the reattached sutured tendon ends and/or a hydrogel form of the present invention is injected within the sheath.

Example 43

Abdominal Surgery

Post-surgical adhesions are reported to form in up to 93% of previously operated laparotomy patients. A laparotomy is required to gain access to the abdomen for large and small intestine procedures, stomach, esophageal, and duodenal procedures, cholecystectomy, hernia repair and operations on the female reproductive systems. In 1992, the Center for Health Statistics reported 344,000 operations in the United States for lysis of peritoneal adhesions. Peritoneal adhesions become pathologic when they anatomically distort abdominal viscera producing various morbidities ranging from intestinal obstruction and volvulus to infertility. Unfortunately, adhesion reformation and recurrence of intestinal obstruction following surgical division of adhesions is fairly common.

To prevent do novo adhesion formation or adhesion reformation, membranes and/or gels of the present invention are placed directly over or wrapped around the surgical site separating this site from the omentum. When closing, membranes of the present invention are placed under the midline incision between the fascia and peritoneum. In laparoscopic procedures, a hydrogel form of the present invention is used to coat the surgical site and trocar entry areas.

The previous examples showing in vivo efficacy at preventing post-surgical adhesions and the reformation of adhesions in experimental animals provide an expectation that similar uses of the films of this invention will also ameliorate the adverse effects of post-surgical adhesions in people.

The compositions of this invention can inhibit formation of de novo adhesions and/or scars at a surgical site or a distant site, can inhibit bleeding and/or formation of blood clots, can promote wound healing, and can act as a seal around re-anastomoses of organs. By inhibiting adhesions, the compositions of this invention can thereby facilitate re-operations of the abdomen.

Example 44

Anti Adhesion Effects II

The purpose of these studies was test the efficacy of cross-linked CMC/PEO polymers in the reduction of adhesion formation in a rabbit uterine horn model of adhesion formation.

Methods:

Animals: Thirty seven female New Zealand White rabbits, 2.4–2.7 kg, were purchased from Irish Farms (Norco, Calif.) and quarantined in the USC vivaria for at least 2 days prior to use. The rabbits were selected randomly for seven groups prior to initiation of surgery. The rabbits were housed on a 12 hour:12 hour light-:dark cycle with food and water available ad libitum.

Materials: The ion-associated ("IA") CMC/PEO polymers used are described below in Table 29. For comparison, a sample of Intergel™ (a trademark of the Ethicon Division of Johnson & Johnson, Inc.), was used. The sutures used to close the incisions in the muscle and the skin were 3-0 coated Dexon II suture (Davis and Geck, Manati, PR).

Double Uterine Horn Model: Rabbits were anesthetized with a mixture of 55 mg/kg ketamine hydrochloride and 5 mg/kg Rompum intramuscularly. Following preparation for sterile surgery, a midline laparotomy was performed. The uterine horns were exteriorized and traumatized by abrasion of the serosal surface with gauze until punctate bleeding developed. Ischemia of both uterine horns was induced by removal of the collateral blood supply. The remaining blood supply to the uterine horns was the ascending branches of the utero-vaginal arterial supply of the myometrium. At the end of surgery, 15 ml of Gels 1–5 described below, Intergel™, or no treatment (control) was administered at the site of injury with a sterile gloved hand. After 7 days, the rabbits were terminated and the percentage of the area of the horns adherent to various organs was determined. In addition, the tenacity of the adhesions was scored using the following system:

Adhesion Scoring System:

0=No Adhesions

1=mild, easily dissectable adhesions

2=moderate adhesions; non-dissectable, does not tear the organ

3=dense adhesions; non-dissectable, tears organ when removed

In addition, an overall score which takes into account all of the above data was given to each rabbit. The following scoring system was used:

0 No adhesions 0.5+ Light, filmy adhesions involving only one organ, typically only 1 or 2 small adhesions.

1.0+ Light, filmy adhesions, not extensive although slightly more extensive than 0.5.

1.5+ Adhesions slightly tougher and more extensive than the 1 rating.

2.0+ Tougher adhesions, a little more extensive, uterine horns usually have adhesions to both bowel and bladder.

2.5+ Same as 2, except the adhesions are usually not filmy at any site and are more extensive.

3.0+ Tougher adhesions that in 2, more extensive, both horns are attached to the bowel and bladder, some movement of the uterus possible.

3.5+ Same as 3, but adhesions slightly more extensive and tougher.

4.0+ Severe adhesions, both horns attached to the bowel and bladder, unable to move the uterus without tearing the adhesions.

The rabbits were scored by two independent observers that were blinded to the prior treatment of the animal. If there was disagreement as to the score to be assigned to an individual animal, the higher score was given.

Statistical Analysis: The overall scores were analyzed by rank order analysis and analysis of variance of the ranks for each treatment and respective control, and for the differences between treatment and control. The lower the score, and the lower the difference, the better the adhesion prevention.

Results:

The effect of administration of these polymers on the incidence of adhesion formation can be found in Table 29.

TABLE 29

Effects of Ionically Cross-Linked Gels on Adhesion Formation

| Treatment | # Sites Adhesion-Free/ # Sites Total | Overall Adhesion Score |
|---|---|---|
| None | 0/40 | 36.0 ± 0.6 |
| Gel 1: 100 kd PEO; 0.82 d.s.; 10% IA | 17/40 | 18.7 ± 3.7 |
| Gel 2: 100 kd PEO; 0.82 d.s.; 60% IA | 14/40 | 19.9 ± 3.2 |
| Gel 3: 8 kd PEO; 0.82 d.s.; 60% IA | 20/40 | 8.4 ± 1.9 |
| Gel 4: 100 kd PEO; 1.19 d.s; 10% IA | 11/40 | 21.9 ± 3.7 |
| Gel 5: 100 kd PEO; 1.19 d.s.; 60% IA | 13/40 | 19.9 ± 3.3 |
| Intergel ™ | 22/56 | 12.0 ± 2.1 |

Data is expressed as the mean rank ± standard deviation; n = 5–7 animals in each group.

Compared to untreated animals, all of the gel preparations of this invention decreased the frequency and overall score of adhesions, according to a Mann-Whitney U test. The greatest antiadhesion effects were obtained using gels having lower molecular weight PEO (8 kd; Gel 3). However, even the gels having the highest molecular weight of PEO (100 kd; Gels 1–2, and 4–5) were effective. Administration of these gels was not associated with the presence of an inflammatory response.

Example 45

Gynecological Surgery: Myomectomy via Laparotomy or Laparoscopy

In surgical excision of a uterine fibroid, the uterus is exposed and incised to remove the fibroid. The uterus is closed with absorbable sutures. Posterior uterine incisions are associated with more and a higher degree of adnexal adhesions than that with fundal or anterior uterine incisions. For posterior incisions, apply compositions of the present invention over the posterior uterine incision and beneath the anterior abdominal wall incision in order to prevent adhesion formation between the uterus and surrounding tissues. Anterior incisions more commonly result in adhesion formation between the bladder and anterior wall of the uterus. Membranes and/or gels of the present invention are placed over the anterior incision and between the uterus and bladder.

Example 46

Thoracic Surgery

Several types of thoracic surgical procedures can benefit from the compositions of this invention. The compositions can inhibit formation of adhesions and scars around the heart, lungs, trachea and esophagus, thereby facilitating re-operations. The compositions can inhibit bleeding, promote wound healing, can act as a seal around arterial punctures, plugs and around reanastomoses of blood vessels and organs. Membranes can also be used as a temporary pericardium. Moreover, the compositions of this invention can also lubricate surgical instruments, including but not limited to endoscopic and intravascular instruments, catheters, stents and devices.

Reoperative cardiac surgical procedures are becoming more commonplace and result in the need to reduce or prevent postoperative mediastinal and pericardial adhesions. A median sternotomy precedes a midline pericardiatomy. The pericardium is suspended, so that the heart and pericardial space are widely exposed. Dissection is performed. To create the bypass, distal anastomoses are constructed using internal mammary arteries, radial arteries, gastroepiploic arteries or saphenous vein grafts. In order to prevent adhesion formation, membranes of the present invention are wrapped around the anastomoses and placed between the pericardium and sternum before closing.

Example 47

Urological Procedures

Gels and fluids of this invention can be used in various urological procedures that involve introduction of instruments and devices, such as catheters, into the urethra, bladder and ureters, thereby inhibiting the trauma that those tissues can be exposed to during the procedure. Injection of fluid and/or gels into the urinary tract can facilitate the expulsion of stones or calculi by acting as a lubricant. Fluids and/or gels can also improve visualization of structures during surgical procedures, and can inhibit bleeding and formation of blood clots.

Example 48

Plastic Surgery

In plastic surgery, the compositions of this invention can be used to coat the outside of various types of implants, including penile implants or breast implants thereby inhibiting the formation of scars, adhesions, and can inhibit capsular contracture resulting from implantation of a prosthesis. The compositions of this invention can also be used as a filler material for breast implants or for testicular implants and artificial sphincters.

Example 49

Orthopedic and Joint Procedures

The compositions of this invention can be used to inhibit the formation of adhesions and scars following joint replacement surgery, joint revision and tendon surgery. Gels and fluids of this invention can be used as synovial fluid replacement for joints, and thereby can decrease the pain, inflammation and swelling of joint structures associated with osteoarthritis. Gels and fluids of this invention can also be used as tendon and ligament lubricants, thereby decreasing the incidence of inflammation of tendons, ligaments and sheaths. The compositions can act as a resorbable tissue growth scaffold or construct to replace missing or worn tissues with regrown ones.

Example 50

Treatment of Joint Inflammation

In other embodiments, the symptoms of joint inflammation can be reduced by delivering a gel composition directly into the joint. Delivery can be carried out either using an arthroscope to visualize the area to have the gel deposited, or through a needle into the joint. In certain situations, it can be desirable to inject microspheres instead of a homogeneous gel.

Example 51

Ear, Nose and Throat Procedures

The compositions of this invention are used to inhibit adhesions and scarring following procedures to the nose, nares, sinuses, middle ear and inner ear.

Example 52

Drug Delivery

The compositions of this invention are used for local administration of drugs, growth factors, enzymes, proteins, pharmacological agents, genes, gene segments, vitamins, and naturopathic substances. The compositions are used in dosage forms intended for oral ingestion, inhalation, transdermal application, rectal or vaginal application, and ocular administration. The compositions of this invention can be combined with surface coating, deposition, impregnation, encapsulation, or in single or multiple layered embodiments.

The types of drugs are antibacterial agents, antiinflammatory agents, antiparasitics, antivirals, anesthetics, antifungals, analgesics, diagnostics, antidepressants, decongestants, antiarthritics, antiasthmatics, anticoagulants, anticonvulsants, antidiabetics, antihypertensives, antiadhesion agents, anticancer agents, gene replacement or modification agents, and tissue replacement drugs.

Other features, aspects and objects of the invention can be obtained from a review of the figures and the claims. All citations herein are incorporated by reference in their entirety.

It is to be understood that other embodiments of the invention can be developed and fall within the spirit and scope of the invention and claims.

We claim:

1. An ionically crosslinked gel comprising:
   a polyacid (PA);
   a polyalkylene oxide (PO); and
   a water soluble multivalent cation.

2. The gel of claim 1, wherein said polyacid is selected from the group consisting of a carboxypolysaccharide, polyacrylic acid, polyamino acid, polylactic acid, polyglycolic acid, polymethacrylic acid, polyterephthalic acid, polyhydroxybutyric acid, polyphosphoric acid, polystyrenesulfonic acid, and copolymers of said polyacids.

3. The gel of claim 1, wherein the polyacid is a carboxypolysaccharide selected from the group consisting of carboxymethyl cellulose (CMC), carboxyethyl cellulose, chitin carboxymethyl chitin, hyaluronic acid, alginate, propylene glycol alginate, pectin, carboxymethyl dextran, carboxymethyl chitosan, heparin, heparin sulfate, chondroitin sulfate and polyuronic acids including polymannuronic acid, polyglucuronic acid and polyguluronic acid.

4. The gel of claim 1, wherein the polyacid is carboxymethylcellulose.

5. The gel of claim 1, wherein the polyacid is carboxymethylcellulose having a molecular weight in the range of about 10 kd to about 10,000 kd and a degree of substitution in the range of greater than about 0 to about 3.

6. The gel of claim 1, wherein said polyalkylene oxide is selected from the group consisting of polypropylene oxide, polyethylene glycol, polyethylene oxide, and PEO/PPO block copolymers.

7. The gel of claim 1 wherein said polyalkylene oxide is polyethylene oxide or polyethylene glycol having a molecular weight in the range of about 200 d to about 8000 kd.

8. The gel of claim 1, wherein said polyalkylene oxide is polyethylene glycol having a molecular weight in the range of about 200 d to about 5 kd.

9. The gel of claim 1, wherein said PA is in the range of about 10% to about 99% by weight of the total solids content.

10. The gel of claim 1, wherein the PA is in the range of about 50% by weight to about 99% by weight, of the total solids content.

11. The gel of claim 1, wherein the PA is in the range of about 90% by weight to about 99% by weight of the total solids content.

12. The gel of claim 1, wherein the PO is in the range of about 1% by weight to about 90% by weight, of the total solids content.

13. The gel of claim 1, wherein the PO is in the range of about 1% by weight to about 10% by weight, of the total solids content.

14. The gel of claim 1, wherein the PO is about 2.5% by weight, of the total solids content.

15. The gel of claim 1, wherein the total solids content of the gel is in the range of about 1% to about 10%.

16. The gel of claim 1, wherein said cation is a trivalent cation.

17. The gel of claim 1, wherein said cation is selected from the group consisting of $Fe^{+3}$, $Al^{+3}$, and $Cr^{+3}$.

18. The gel of claim 1, wherein said cation is a divalent cation.

19. The gel of claim 1, wherein said cation is a divalent cation selected from the group consisting of $Ca^{+2}$, $Zn^{+2}$, $Mg^{+2}$ and $Mn^{+2}$.

20. The gel of claim 1, wherein said cation is accompanied by an inorganic anion.

21. The gel of claim 1, wherein said cation is accompanied by an inorganic anion selected from the group consisting of Cl, $PO_4^{2-}$, $HPO_3^-$; $CO_3^{2-}$; $HCO_3^-$; $SO_4^{2-}$ and borates.

22. The gel of claim 1, wherein said cation is accompanied by an organic anion.

23. The gel of claim 1, wherein said cation is accompanied by an organic anion selected from the group consisting of citrate, oxalate and acetate.

24. The gel of claim 1, wherein the pH of the gel is in the range of about 2.0 to about 7.5.

25. The gel of claim 1, wherein the pH of the gel is in the range of about 2.5 to about 6.0.

26. The gel of claim 1, further comprising a drug.

27. The gel of claim 1, further comprising a drug selected from the group consisting of antithrombogenic drugs, antiinflammatory drugs, hormones, chemotactic factors, analgesics, growth factors, cytokines, osteogenic factors and anesthetics.

28. The gel of claim 1, further comprising drug selected from the group consisting of heparin, tissue plasminogen activator, aspirin, ibuprofen, ketoprofen, proteins and peptides containing an RGD motif, and non-steroidal anti-inflammatory drugs.

29. The gel of claim 1 having a viscosity below about 500,000 centipoise.

30. The gel of claim 1, wherein the polyacid is about 90% by weight of the total solids content and the polyalkylene oxide is about 10% by weight of the total solids content.

31. The gel of claim 1, wherein the polyacid is about 97.5% by weight of the total solids content and the polyalkylene oxide is about 2.5% by weight of the total solids content.

32. The gel of claim 30, wherein said cation is $Ca^{2+}$ and said gel further comprises Cl.

33. The gel of claim 31, wherein said cation is $Ca^{2+}$ and said gel further comprises $Cl^-$.

34. The gel of claim 30, wherein the total solids content of said gel is about 4 gm/100 ml.

35. The gel of claim 31, wherein the total solids content of said gel is about 4 gm/100 Ml.

36. The gel of claim 30, wherein
   said polyacid is carboxymethylcellulose having an average molecular weight of about 700,000 Daltons; and a degree of substitution of between about 0.81 and about 0.83;

said polyalkylene oxide is polyethylene oxide having an average molecular weight of about 4,000 kDaltons; and said monoatomic cation is $Ca^{2+}$ in a concentration of from about 0.2 gm/100 ml to about 0.5 mg/100 ml.

37. The gel of claim 31, wherein said polyacid is carboxymethylcellulose having an average molecular weight of about 700,000 Daltons; and a degree of substitution of between about 0.81 and about 0.83;

said polyalkylene oxide is polyethylene oxide having an average molecular weight of about 4,000 kDaltons; and said monoatomic cation is $Ca^{2+}$ in a concentration of from about 0.2 gm/100 ml to about 0.5 mg/100 ml.

38. The gel of claim 36, wherein the total solids content of said gel is about 4 gm/100 ml.

39. The gel of claim 37, wherein the total solids content of said gel is about 4 mg/100 ml.

40. The gel of claim 1, wherein sufficient cations are present to provide said gel with a viscosity of about 200,000 centipoise to about 300,000 centipoise as measured at a rotation rate of ½ rpm.

41. The gel of claim 37, wherein sufficient calcium is present to provide said gel with a viscosity of about 200,000 centipoise to about 300,000 centipoise as measured at a rotation rate of ½ rpm.

42. An ionically cross-linked gel comprising:

a polyacid (PA);

a polyalkylene oxide (PO); and a monoatomic water soluble multivalent cation selected from the group consisting of $Ca^{+2}$, $Mg^{2+}$, $Mn^{2+}$, $Co^{2+}$, $Al^{3+}$ and $Fe^{3+}$.

* * * * *